US010335026B2

(12) United States Patent
Inao et al.

(10) Patent No.: US 10,335,026 B2
(45) Date of Patent: Jul. 2, 2019

(54) IMAGE PROCESSING APPARATUS THAT GENERATES A TOMOGRAPHIC IMAGE USING AN ESTIMATION VALUE OF PIXEL VALUES, AND RELATED OPTICAL COHERENCE TOMOGRAPHY APPARATUS, IMAGE PROCESSING METHOD, AND COMPUTER-READABLE STORAGE MEDIUM

(71) Applicant: CANON KABUSHIKI KAISHA, Tokyo (JP)

(72) Inventors: Yasuhisa Inao, Tokyo (JP); Shinya Tanaka, Tokyo (JP); Yohei Saito, Kawasaki (JP); Hayato Shioda, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/860,760

(22) Filed: Jan. 3, 2018

(65) Prior Publication Data
US 2018/0192870 A1    Jul. 12, 2018

(30) Foreign Application Priority Data

Jan. 11, 2017 (JP) ................................ 2017-002878
Feb. 28, 2017 (JP) ................................ 2017-035923
(Continued)

(51) Int. Cl.
*A61B 3/14* (2006.01)
*A61B 3/10* (2006.01)
(Continued)

(52) U.S. Cl.
CPC ........... *A61B 3/102* (2013.01); *A61B 3/0025* (2013.01); *G06T 5/50* (2013.01); *A61B 3/117* (2013.01);
(Continued)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS

| | | | | |
|---|---|---|---|---|
| 9,232,887 B2* | 1/2016 | Goto | ..................... | G01B 9/0203 |
| 2007/0269135 A1* | 11/2007 | Ono | ...................... | G06T 3/0087 |
| | | | | 382/276 |
| 2011/0043649 A1* | 2/2011 | Nakada | ..................... | G06T 3/40 |
| | | | | 348/218.1 |

OTHER PUBLICATIONS

Chan, Aaron C., et al. "Maximum a posteriori estimator for high-contrast image composition of optical coherence tomography", Optics Letter, vol. 41, No. 2, pp. 321-324, Optical Society of America, Jan. 15, 2016.

* cited by examiner

*Primary Examiner* — Mohammed A Hasan
(74) *Attorney, Agent, or Firm* — Venable LLP

(57) ABSTRACT

An image processing apparatus includes a processor that acquires a plurality of sets of tomographic signals acquired by an image sensor, and generates a representative value in each pixel position of the tomographic image, using the plurality of sets of tomographic signals, and generates the tomographic image with the representative value in each pixel position as a pixel value by determining a target region in which contrast is reduced in the tomographic image, using at least one set of tomographic signals, out of the plurality of sets of tomographic signals, and estimating an estimation value, in each pixel position of the target region, by performing statistical processing on a plurality of tomographic signals corresponding to the pixel position, out of the plurality of sets of tomographic signals. The tomographic image is generated with the estimation value as the representative value in the target region.

28 Claims, 35 Drawing Sheets

(30) Foreign Application Priority Data

Feb. 28, 2017 (JP) ................................ 2017-035925
Nov. 6, 2017 (JP) ................................ 2017-213801

(51) Int. Cl.
*A61B 3/00* (2006.01)
*G06T 5/50* (2006.01)
*A61B 3/117* (2006.01)
*A61B 3/12* (2006.01)

(52) U.S. Cl.
CPC ... *A61B 3/1225* (2013.01); *G06T 2207/10101* (2013.01); *G06T 2207/20076* (2013.01); *G06T 2207/20172* (2013.01)

(58) Field of Classification Search
USPC ........................................................ 351/206
See application file for complete search history.

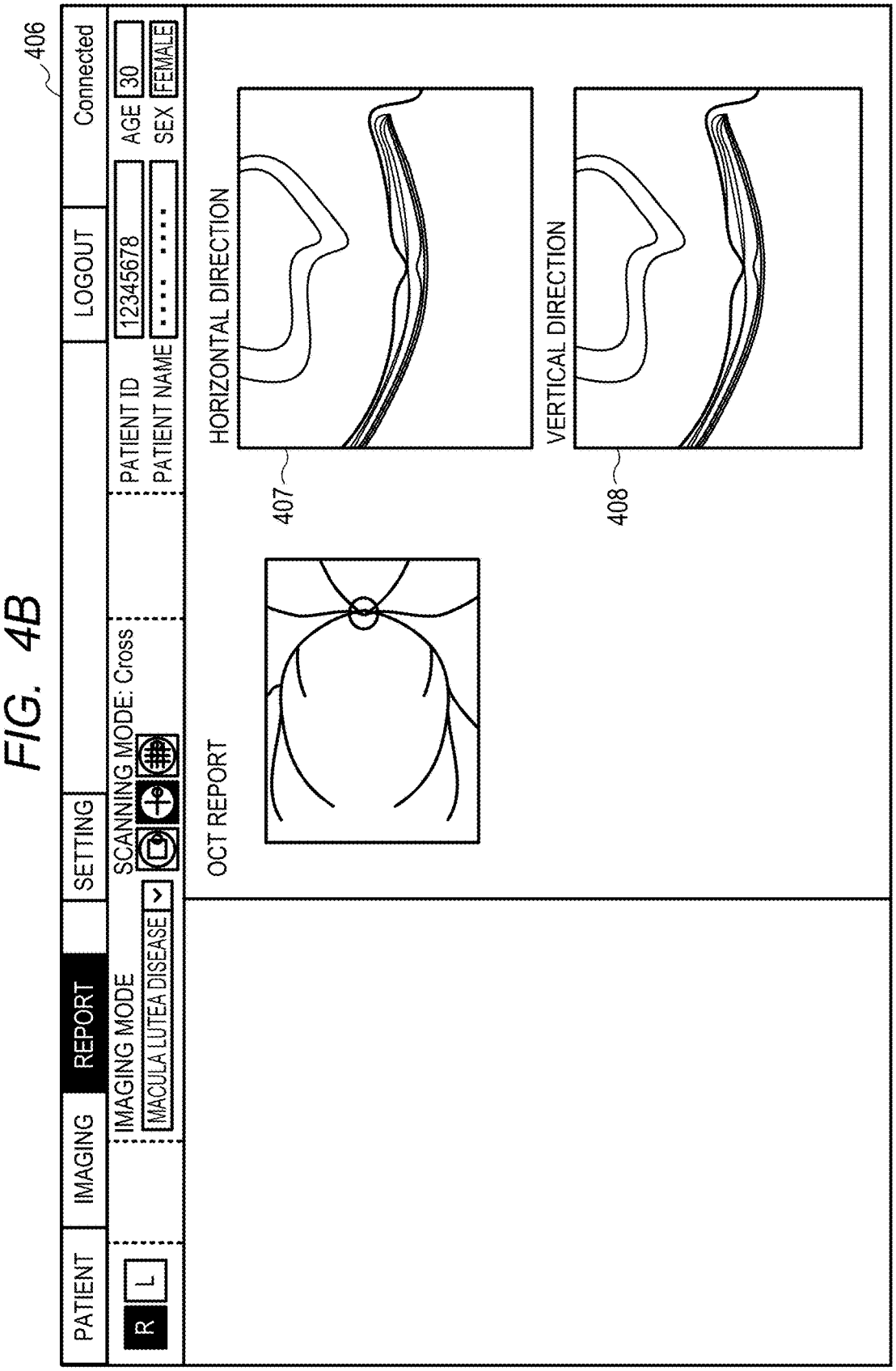

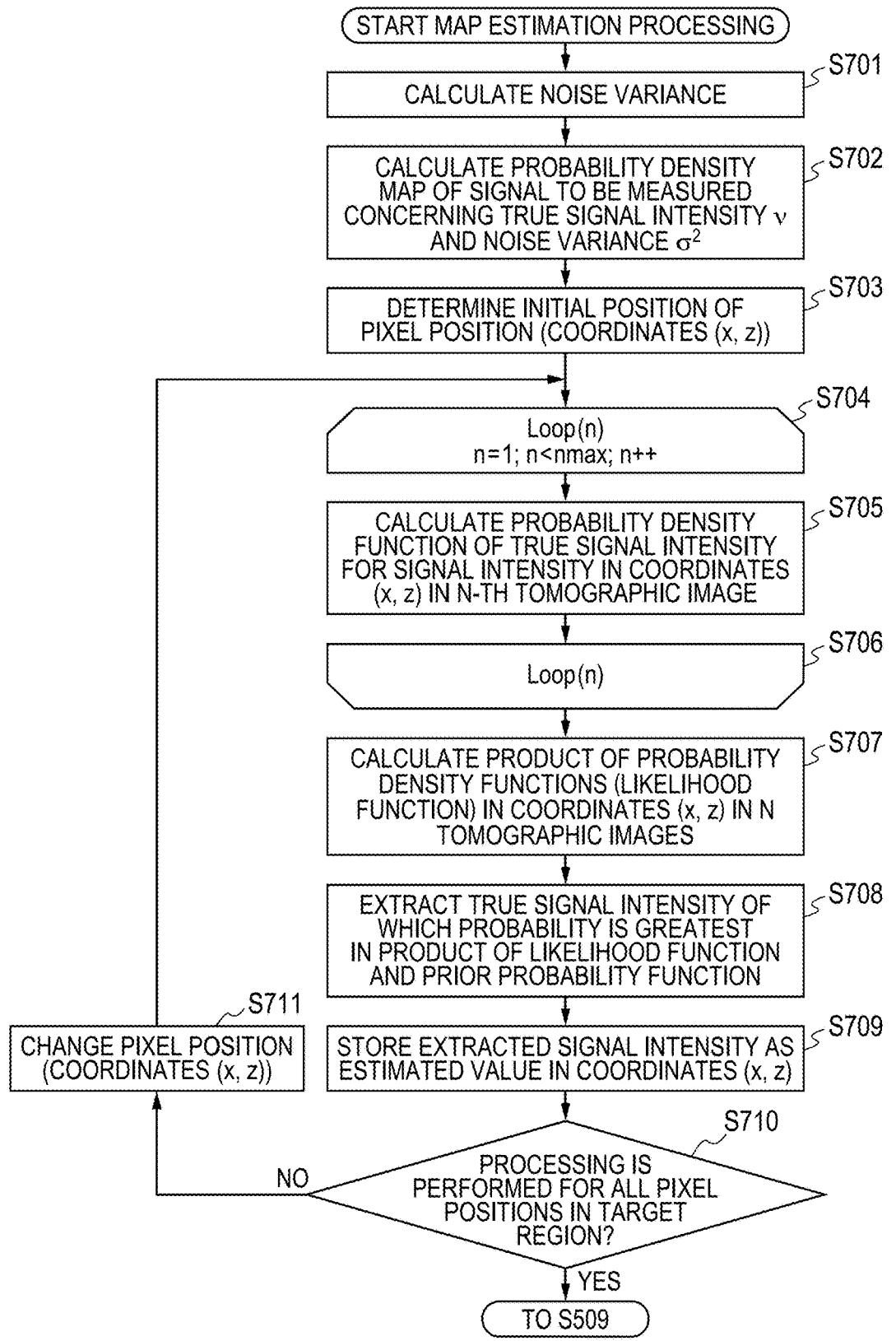

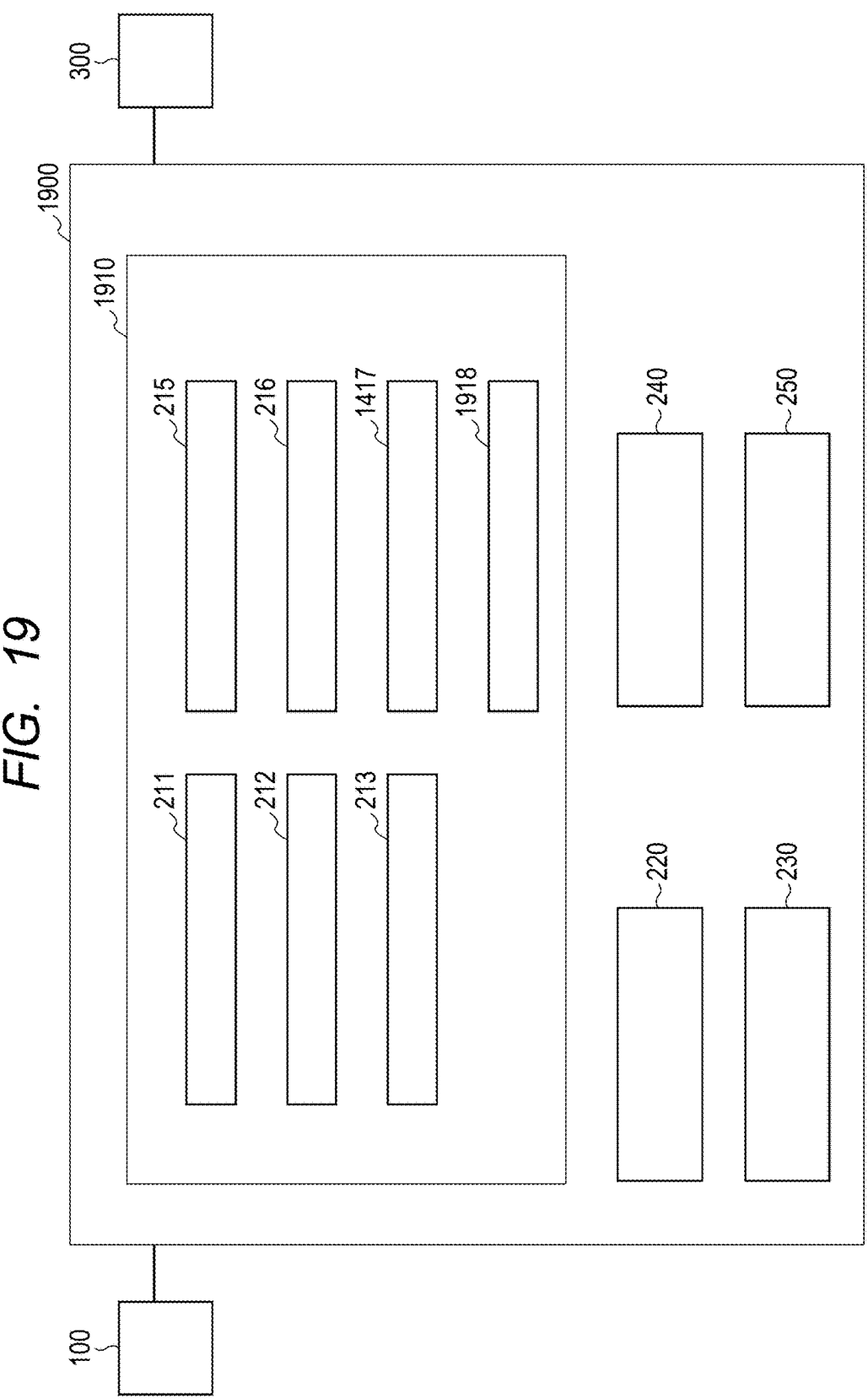

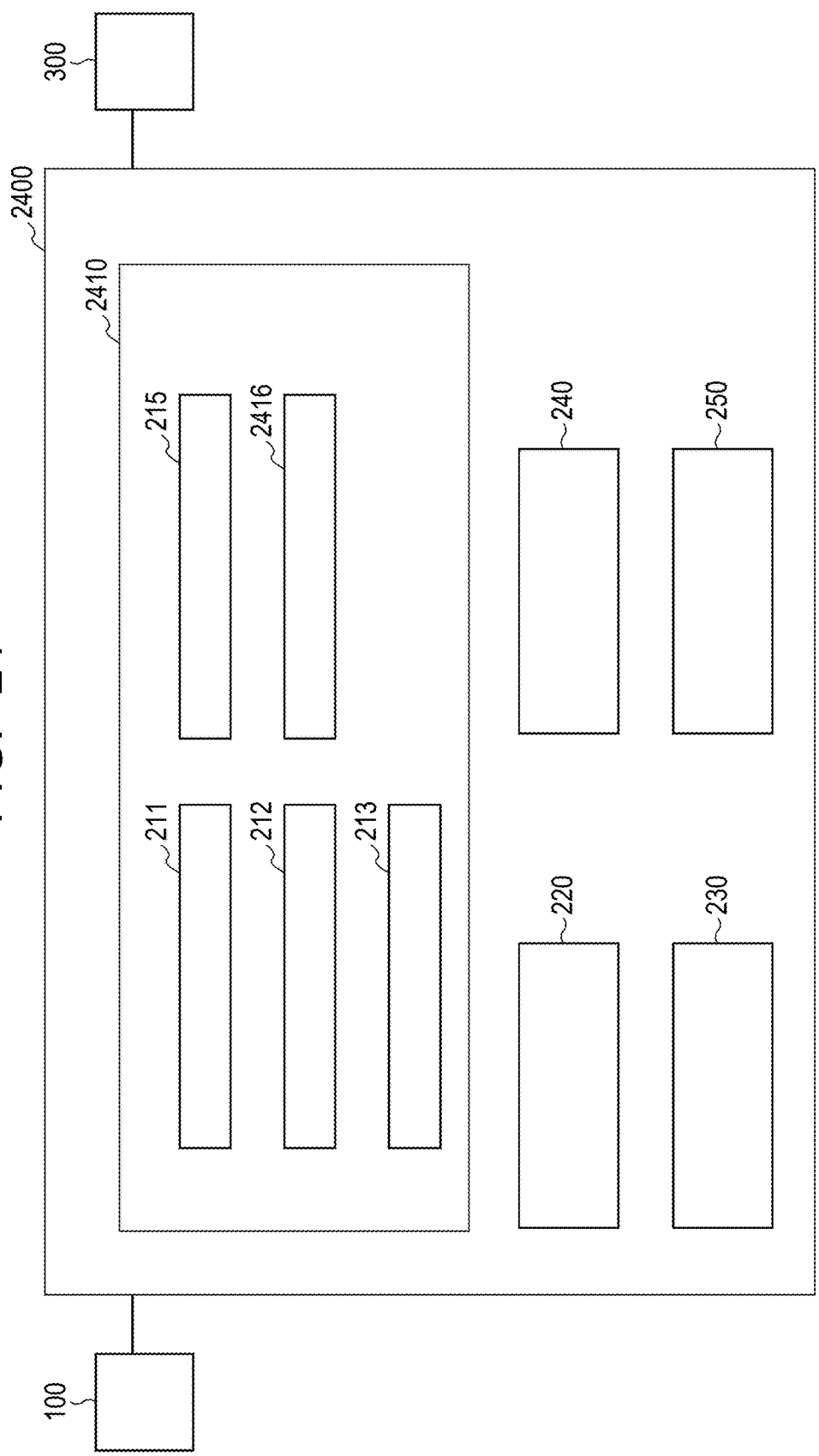

FIG. 28A

|   | 1 |   |
|---|---|---|
| 1 | 2 | 1 |
|   | 1 |   |

FIG. 28B

| 1 | 2 | 1 |
|---|---|---|
| 2 | 3 | 2 |
| 1 | 2 | 1 |

FIG. 28C

| 1 | 2 | 3 | 2 | 1 |
|---|---|---|---|---|
| 2 | 3 | 4 | 3 | 2 |
| 3 | 4 | 5 | 4 | 3 |
| 2 | 3 | 4 | 3 | 2 |
| 1 | 2 | 3 | 2 | 1 |

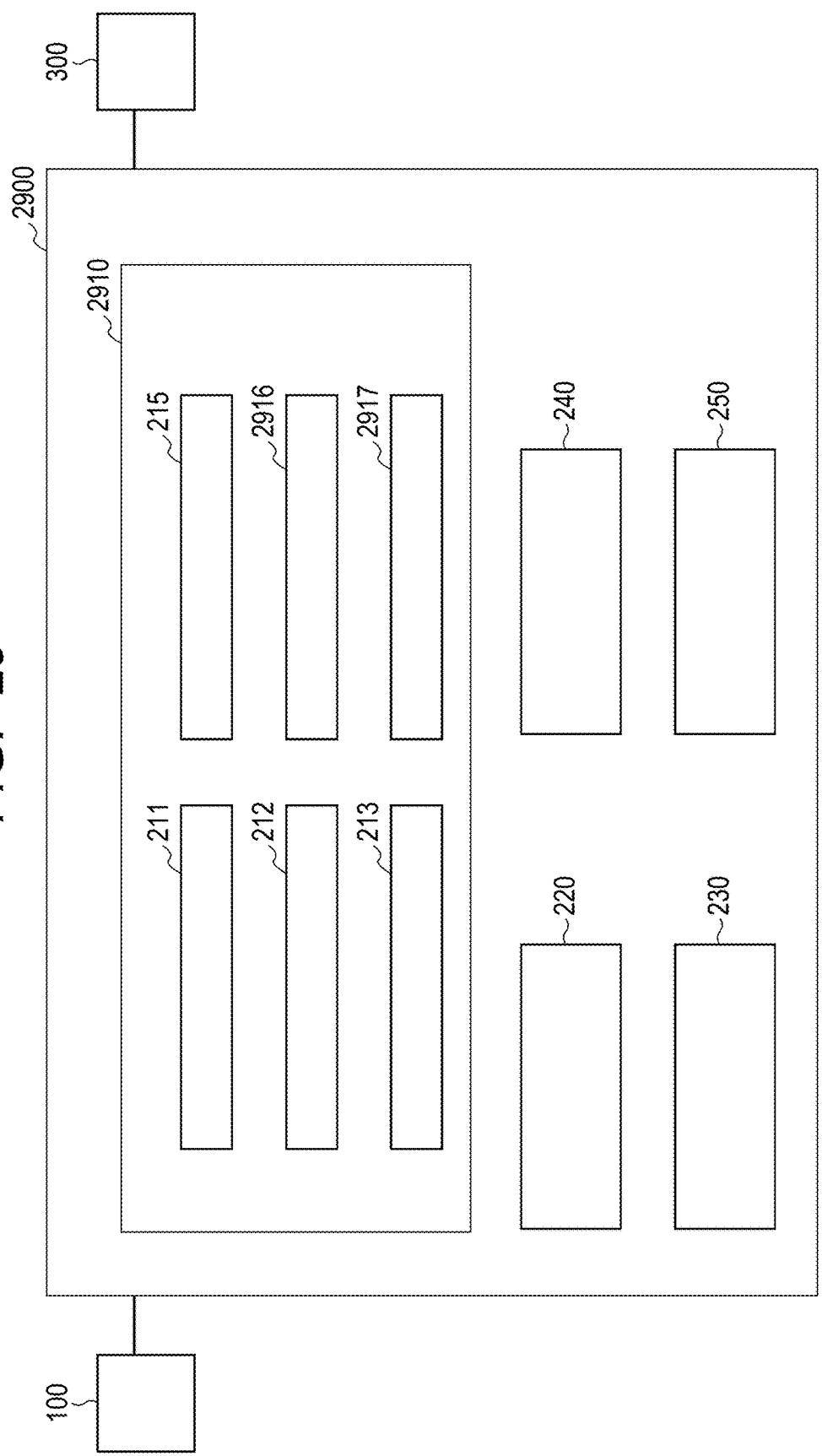

IMAGE PROCESSING APPARATUS THAT GENERATES A TOMOGRAPHIC IMAGE USING AN ESTIMATION VALUE OF PIXEL VALUES, AND RELATED OPTICAL COHERENCE TOMOGRAPHY APPARATUS, IMAGE PROCESSING METHOD, AND COMPUTER-READABLE STORAGE MEDIUM

This application claims the benefit of Japanese Patent Application No. 2017-002878, filed Jan. 11, 2017, Japanese Patent Application No. 2017-035923, filed Feb. 28, 2017, Japanese Patent Application No. 2017-035925, filed Feb. 28, 2017, and Japanese Patent Application No. 2017-213801, filed Nov. 6, 2017, each of which is hereby incorporated by reference herein in its entirety.

BACKGROUND OF THE INVENTION

Field of the Invention

This disclosure relates to an image processing apparatus, an optical coherence tomography apparatus, an image processing method, and a computer-readable storage medium.

Description of the Related Art

In recent years, an apparatus using optical coherence tomography (Optical Coherence Tomography: OCT) (hereafter, referred to as an OCT apparatus) that can observe and measure sections of a fundus and an anterior eye portion noninvasively has been widely used in the ophthalmology field. The OCT apparatus irradiates a subject eye with low coherent light (measurement light), and obtains information concerning the section of the subject eye using interference light obtained by combining a return light from the subject eye and a reference light. The OCT apparatus can acquire a tomographic image by scanning a low coherent light on the fundus of a subject eye. OCT apparatuses are widely used in medical care, including research and clinical use.

OCT is broadly divided into two types, namely, time domain OCT and Fourier domain OCT. Further, Fourier domain OCT includes spectral domain OCT (SD-OCT) and swept source OCT (SS-OCT). In Fourier domain OCT, information on the section of a subject can be acquired using a light source having a wide wavelength band, separating an interference light into spectral components to acquire a signal, and applying Fourier conversion, or the like, to the acquired signal. In SD-OCT, light is separated into spectral components spatially by a spectroscope. In contrast with this, in SS-OCT, light is temporally separated into spectral components using a light source that emits lights of different wavelengths temporally.

As for the tomographic images of an anterior eye portion and a fundus that are obtained in OCT, states of these tissues can be observed only with a single tomographic image. It has been difficult however, to observe and to measure a vitreous body that is a tissue with a small refractive index difference from which only a feeble signal can be obtained, a choroid membrane existing in a deep part of a fundus tissue, and the like, in detail with only a single tomographic image, because the acquired signals are buried in noise of the apparatus.

With regard to this problem, a method has been adopted conventionally that reduces noise of the single tomographic image, and generates a higher-definition tomographic image, by averaging a plurality of tomographic images that are acquired by imaging the same spot of a subject a plurality of times.

On the other hand, the latest research has revealed that the contrast of the tomographic image that is generated by averaging becomes low in a region in which the signal intensity is low in principle. According to "Maximum a posteriori estimator for high-contrast image composition of optical coherence tomography", by Chan et al., published in Vol. 41, No. 2, pp. 321 to 324, of *Optics Letters*, on Jan. 15, 2016 (hereafter, referred to as the Chan et al. publication), it is known that the signal intensity of OCT becomes a Rice distribution, so that, especially in the region in which the signal intensity is low, bias in the direction in which the value becomes large is applied to the signal intensity by averaging of the signal intensities. Consequently, in the tomographic image in which averaging is performed, imaging is performed based on the signal intensity greater than an actual signal intensity in the region in which the signal intensity is low, and contrast between the region with a high signal intensity and the region with a low signal intensity becomes low.

In the light of the fact that the contrast becomes low by averaging a tomographic image, the Chan et al. publication proposes the method for generating a tomographic image using Maximum a posteriori (MAP) estimation processing that is a kind of statistical processing. In the method, by MAP estimation, a high-contrast tomographic image is obtained by generating a tomographic image by estimating a value closer to an actual signal as a signal intensity, as compared with averaging of a tomographic image. According to the Chan et al. publication, a tomographic image that has a greater contrast in the choroid membrane in the deep part of a fundus, and that is more suitable to detailed observation and measurement, as compared with the conventional averaged tomographic image, is generated by the method. In the method described in the Chan et al. publication, with respect to all pixels of a tomographic image, a likelihood concerning the signal intensity of each pixel in a plurality of tomographic images in the same spot is calculated, and the signal intensity at which the product of the likelihoods becomes a maximum is estimated as a true signal intensity.

SUMMARY OF THE INVENTION

The disclosure provides an image processing apparatus, an optical coherence tomography apparatus, an image processing method, and a computer-readable storage medium that can generate a high-contrast tomographic image with the use of statistical processing.

According to one aspect, the present invention provides an image processing apparatus that processes a tomographic image generated using a plurality of sets of tomographic signals acquired by performing optical coherence tomographic imaging a plurality of times using a measurement light controlled to scan substantially a same spot of a subject, the image processing apparatus including an acquiring unit configured to acquire the plurality of sets of tomographic signals, and a generation unit configured to generate a representative value in each pixel position of the tomographic image using the plurality of sets of tomographic signals, and generates the tomographic image with the representative value in each pixel position as a pixel value, wherein the generation unit includes a region determination unit configured to determine a target region in which contrast is reduced in the tomographic image, using at least one set of tomographic signals out of the plurality of sets of tomographic signals, and an estimation unit configured to estimate an estimation value, in each pixel position of the target region, by performing statistical processing on a plurality of tomographic signals corresponding to the pixel position, out of the plurality of sets of tomographic signals, and wherein the generation unit generates the tomographic image with the estimation value as the representative value in the target region.

According to another aspect, the present invention provides an image processing apparatus that processes a tomographic image generated using tomographic signals acquired by subjecting a subject to optical coherence tomographic imaging, the image processing apparatus including an acquiring unit configured to acquire the tomographic signals, and a generation unit configured to generate the tomographic image using the tomographic signals, wherein the generation unit includes an estimation unit configured to estimate an estimation value by performing statistical processing on tomographic signals corresponding to a pixel position of the tomographic image out of the tomographic signals, and a filter unit configured to apply a noise removal filter to a tomographic image generated using the estimation value as a pixel value.

According to yet another aspect, the present invention provides an image processing apparatus that processes a tomographic image generated using tomographic signals acquired by subjecting a subject to optical coherence tomographic imaging, the image processing apparatus including an acquiring unit configured to acquire the tomographic signals, and a generation unit configured to generate the tomographic image using the tomographic signals, wherein the generation unit includes an estimation unit configured to estimate an estimation value by performing statistical processing on a tomographic signal corresponding to a pixel position of the tomographic image out of the tomographic signals, wherein the estimation unit estimates the estimation value by performing statistical processing on tomographic signals corresponding to a pixel position, the estimation value of which is estimated, and pixel positions around the pixel position out of the tomographic signals, and wherein the generation unit generates the tomographic image with the estimation value as a pixel value.

According to still another aspect, the present invention provides an image processing method that processes a tomographic image generated using tomographic signals acquired by subjecting a subject to optical coherence tomographic imaging, the method including acquiring the tomographic signals, and generating the tomographic image using the tomographic signals, wherein the generating the tomographic image includes determining a target region in which contrast is reduced in the tomographic image, using the tomographic signals, estimating an estimation value by performing statistical processing on tomographic signals of the target region out of the tomographic signals, and generating the tomographic image with the estimation value as a pixel value in the target region.

Further features of the present invention will become apparent from the following description of exemplary embodiments with reference to the attached drawings.

BRIEF DESCRIPTION OF THE DRAWINGS

FIG. 4B illustrates an example of the display screen of the display unit according to example 1.

FIG. 7 illustrates a flowchart of MAP estimation processing according to example 1.

FIG. 19 illustrates a schematic configuration of a control unit according to example 5.

FIG. 24 illustrates a schematic configuration of a control unit according to example 7.

FIG. 28A is a view for describing weighting according to a modified example of example 7.

FIG. 28B is a view for describing weighting according to the modified example of example 7.

FIG. 28C is a view for describing weighting according to the modified example of example 7.

FIG. 29 illustrates a schematic configuration of a control unit according to example 8.

DESCRIPTION OF THE EMBODIMENTS

Figure 1:
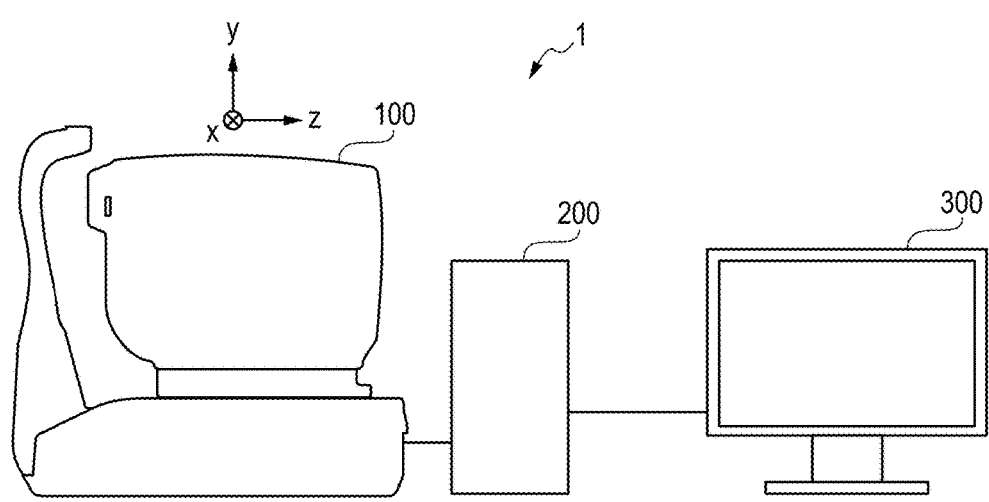
FIG. 1 illustrates a schematic configuration of an OCT apparatus according to example 1.

Preferred embodiments of the invention will now be described in detail in accordance with the accompanying drawings.

Note that dimensions, materials, shapes, relative positions of components, and the like, that are described in the of following embodiments and examples are arbitrary, and can be changed in accordance with configurations of apparatuses to which the invention is applied or various conditions. Further, in the drawings, the same reference signs are used among the drawings to illustrate the same or functionally similar elements.

Embodiment 1

In MAP estimation processing described in the Chan et al. publication, the estimation described above is performed with respect to all pixels of a tomographic image, so that an amount of calculation becomes very large, and much time is taken to calculate the result. Consequently, a physical burden is sometimes given to a subject, and imaging of a large number of subjects sometimes becomes difficult. Thus, embodiment 1 of the disclosure provides an optical coherence tomography apparatus that can generate a tomographic image with greater contrast than an averaged image in a shorter amount of time.

Hereafter, the present embodiment will be schematically described, before examples of the present embodiment are described. In the present embodiment, in order to generate a high-contrast tomographic image in a short time, the amount of calculation that takes a lot of time is decreased by limiting pixels for which MAP estimation is performed. A reason why a tomographic image with greater contrast than a conventional averaged tomographic image can be generated in a shorter amount of time as compared with the method described in the Chan et al. publication, will be described hereafter.

In a Rice distribution, in a case of signal intensity being low, a bias, in a direction in which a value becomes large, occurs to the signal intensity at a time of performing averaging due to asymmetry that is protruded to a positive direction of the signal intensity. Consequently, when a tomographic image is generated by averaging a plurality of tomographic images as described above, the tomographic image is generated based on a signal intensity that is greater than actual signal intensity in a region in which the signal intensity is low. To the region like this, in the method disclosed in the Chan et al. publication, a value that is closer to the actual signal intensity can be calculated by MAP estimation. The signal intensity mentioned here mainly refers to a luminance value that is a pixel value of a pixel, but can be a value of a signal corresponding to a pixel. Consequently, the signal intensity includes an intensity of a signal obtained after subjecting an interference signal to Fourier conversion, and an intensity of a signal obtained by applying some kind of signal processing to the signal after Fourier conversion.

Meanwhile, it has been conventionally known that when the value of an actual signal (signal intensity) is sufficiently large with respect to noise in a Rice distribution, the distribution is close to a Gaussian distribution. Consequently, it is understood that when the signal intensity is high, there is no difference between results of averaging of the OCT tomographic image and MAP estimation.

Here, in order to make the conventional averaged OCT tomographic image an image with greater contrast, the pixel value can be made a low value that is closer to the actual signal intensity, as compared with the pixel of the averaged image by performing MAP estimation with respect to a pixel with a low actual signal intensity. In contrast with this, concerning a pixel with a high signal intensity, there is no difference between the result of MAP estimation and the averaged result, so that MAP estimation does not have to be performed.

As described above, in a case of performing MAP estimation, the amount of calculation significantly increases, as compared with a case of performing averaging. Consequently, average processing is performed in the pixels with high signal intensities, and MAP estimation processing is performed for only a pixel with a low signal intensity, whereby a tomographic image with high contrast, which is equivalent to a case in which MAP estimation is performed with respect to all pixels of the tomographic image, can be generated in a shorter amount of time.

In the present embodiment, a basis of a reference of determination that divides processing contents to respective pixels into MAP estimation and averaging is a signal intensity in each of the pixels. For example, it is conceivable to calculate a histogram of the signal intensity using the averaged tomographic image, and to perform MAP estimation in the case of a signal intensity of a threshold value or less, with a lower 10 percentile of the histogram set as the threshold value. Further, as another method, a setting method of a threshold value using a shape of a histogram, and the like, are conceivable.

As still another method, a determination method using a segmentation function that discriminates a layer structure of a fundus tissue and is included in the conventional OCT is conceivable. For example, from a structure of an eye, as the region in which signal intensity is low, a vitreous body in which a signal intensity is low because a refraction index difference is small, a choroid membrane that a measurement light of the OCT hardly reaches because it is in a fundus deep part, or the like, are known as the regions in which the signal intensity is low. Consequently, a method that performs segmentation processing on a tomographic image, extracts regions, such as a vitreous body and a choroid membrane, performs MAP estimation processing for the extracted regions, and performs average processing with respect to other regions, and the like, is conceivable.

By performing the processing like this, a region in which the signal intensity is considered to be low can be determined. In the present embodiment, a high-contrast tomographic image can be generated in a short time by performing MAP estimation processing that requires a large amount of calculation to only the determined region.

Example 1

Hereafter, with reference to FIGS. 1 to 9, an optical coherence tomography apparatus (OCT apparatus) according to example 1 of the present embodiment will be described. FIG. 1 illustrates a schematic configuration of an OCT apparatus 1 according to the present example. In the OCT apparatus 1, an imaging optical system 100, a control unit 200 (an image processing apparatus), and a display unit 300 are provided.

The imaging optical system 100 irradiates a subject eye that is a subject with a measurement light, and generates an interference signal by detecting an interference light of a return light from the subject eye and a reference light. The control unit 200 is connected to the imaging optical system 100 and the display unit 300, and controls the imaging optical system 100 and the display unit 300. Further, the control unit 200 acquires the interference signal generated by the imaging optical system 100, and can generate a tomographic image of the subject eye. The display unit 300 can display various images, information on the subject eye, and the like, that are sent from the control unit 200.

Here, the control unit 200 may be configured using a general-purpose computer, or may be configured as a dedicated computer of the imaging optical system 100. The display unit 300 can be configured using an arbitrary display. Note that, in the present example, the control unit 200 and the display unit 300 are configured to be separate units from the imaging optical system 100, but all or parts of the control unit 200 and the display unit 300 may be integrally configured.

Configuration of Imaging Optical System

Figure 2:
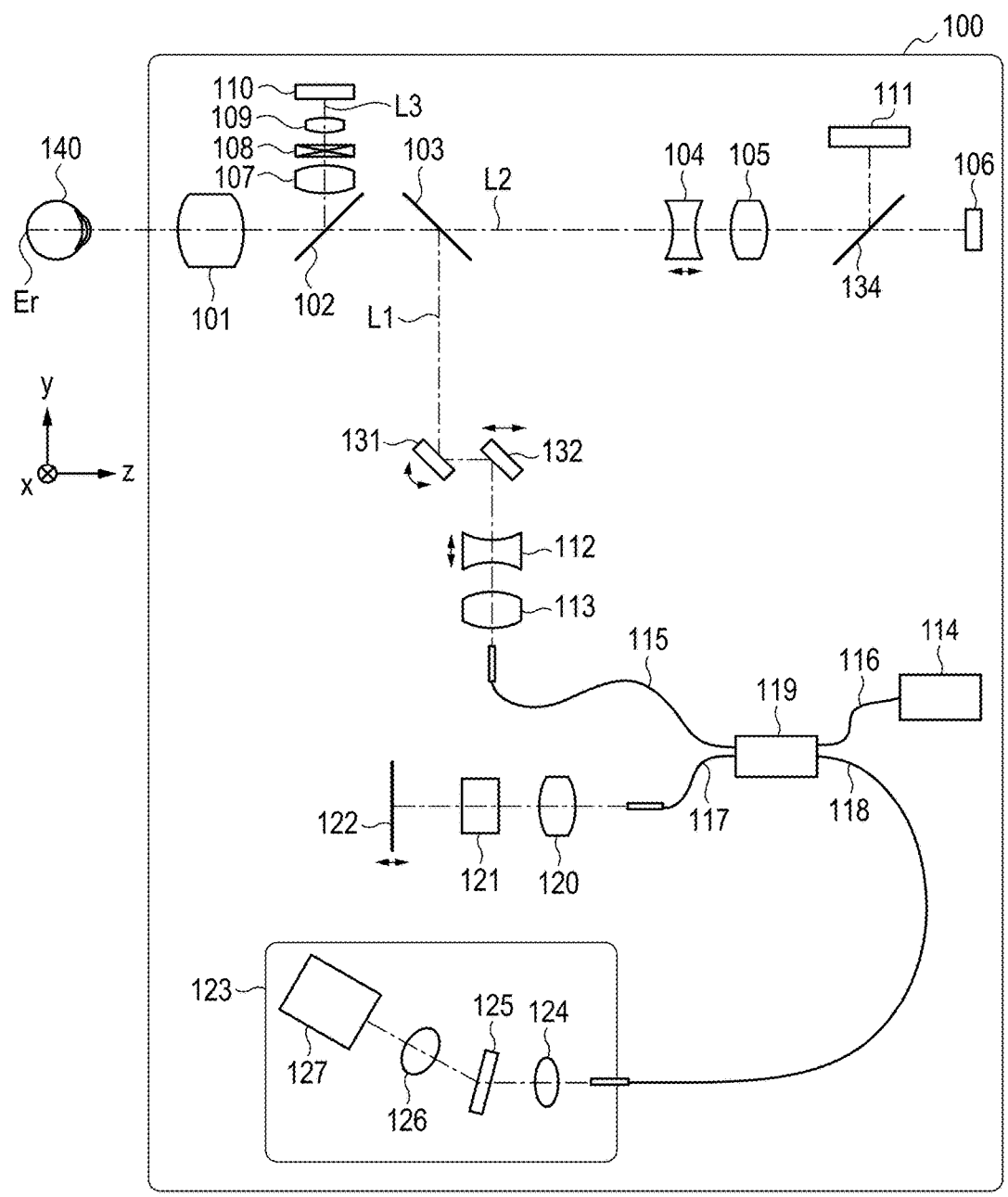
FIG. 2 illustrates a schematic configuration of an imaging optical system according to example 1.

Next, with reference to FIG. 2, a configuration of the imaging optical system 100 according to the present example will be described. FIG. 2 illustrates a schematic configuration of the imaging optical system 100.

In the imaging optical system 100, an objective lens 101 is placed to face a subject eye 140. A dichroic mirror 102 and a dichroic mirror 103 are provided on an optical axis of the objective lens 101. An optical path from the objective lens 101 is branched to an optical path L1 of an OCT optical system, an optical path L2 of an internal fixation lamp, and a fundus observation system, and an optical path L3 of an anterior eye part observation system, according to wavelength bands of lights that pass through the optical paths by the dichroic mirrors 102 and 103. In the present example, the optical path L1 of the OCT optical system and the optical path L2 of the internal fixation lamp and the fundus observation system are disposed in a transmission direction of the dichroic mirror 102, and the optical path L3 of the anterior eye part observation system is disposed in a reflection direction. Further, the optical path L2 of the internal fixation lamp and the fundus observation system is disposed in a transmission direction of the dichroic mirror 103, and the optical path L1 of the OCT optical system is disposed in a reflection direction. Dispositions of these optical paths are not, however, limited to the dispositions, and the respective optical paths may be disposed to be in opposite positions, respectively, in the transmission directions and the reflection directions of the dichroic mirrors 102 and 103.

On the optical path L2, lenses 104 and 105, a dichroic mirror 134, an internal fixation lamp 106, and a charge-coupled device (CCD) 111 for fundus observation are provided. Components that are disposed in the optical path of a fundus observation system configure a fundus observation optical system. The lens 104 is a focusing lens, and is driven in an optical axis direction, illustrated by an arrow in the drawing, by a motor, which is not illustrated, which is controlled by the control unit 200, for the purpose of focusing adjustment of a light passing through the optical path L2. The optical path L2 is branched into an optical path to the internal fixation lamp 106 and an optical path to the CCD 111 by the dichroic mirror 134. In the present example, the internal fixation lamp 106 is disposed in a transmission direction of the dichroic mirror 134, and the CCD 111 is disposed in a reflection direction. Note that the CCD 111 may be disposed in the transmission direction of the dichroic mirror 134, and the internal fixation lamp 106 may be provided in the reflection direction.

The CCD 111 has sensitivity to a wavelength of illuminating light for fundus observation not illustrated, specifically, to a vicinity of 780 nm. The internal fixation lamp 106 is used to urge fixation of a subject by generating a visible light.

A return light that is emitted from a light source for fundus observation and is reflected by the subject eye 140 passes through the objective lens 101, and the dichroic mirrors 102 and 103, and is incident on the optical path L2. The return light incident on the optical path L2 passes through the lenses 104 and 105, and, thereafter, is reflected by the dichroic mirror 134, and is guided to the CCD 111. The CCD 111 detects the incident return light from the subject eye 140, and generates a signal corresponding to the return light. The control unit 200 can obtain a front image of a fundus Er of the subject eye 140 based on a signal generated by the CCD 111.

A light that is emitted from the internal fixation lamp 106 passes through the dichroic mirror 134, the lenses 105 and 104, the dichroic mirrors 103 and 102, and the objective lens 101, and is incident on the subject eye 140. The internal fixation lamp 106 can provide a light in an arbitrary shape to an arbitrary position on the subject eye 140 as a fixation target, and can urge fixation of a subject.

Note that the configuration of the fundus observation optical system is not limited to the configuration described above, and may also have a configuration of Scanning Laser Ophthalmoscope (SL) that scans an illuminating light onto a subject eye, for example. In this case, a light in an arbitrary shape can be provided to an arbitrary position on the subject eye 140 as a fixation target by flashing the internal fixation lamp 106 in accordance with movement of a scanning unit of an SLO optical system, and fixation of a subject can be urged.

The optical path L3 of the anterior eye part observation system will be described next. On the optical path L3 of the anterior eye part observation system, lenses 107 and 109, a split prism 108 and a CCD 110 for anterior eye part observation that detects infrared light are provided. Note that these components disposed on the optical path L3 of the anterior eye part observation system configure an anterior eye part observation optical system (an imaging unit).

In the optical path L3, a light, for observing an anterior eye part, and which has a wavelength in a vicinity of 970 nm, is irradiated to an anterior eye part of the subject eye 140 from a light source, which is not illustrated. A reflection light from the anterior eye part of the subject eye 140 is incident on a split prism 108 via the objective lens 101, the dichroic mirror 102 and the lens 107. The split prism 108 is disposed in a position conjugated with a pupil of the subject eye 140. The light that is emitted from the split prism 108 is incident on the CCD 110 via the lens 109.

The CCD 110 detects a light having a wavelength in the vicinity of 970 nm, detects a reflection light from the anterior eye part, and generates a signal corresponding to the reflection light from the anterior eye part. The control unit 200 can generate an image of the anterior eye part of the subject eye 140 based on a signal generated by the CCD 110. At this time, the control unit 200 can detect a distance in a Z-direction (a depth direction) of the imaging optical system 100 to the subject eye 140 from a split image of the anterior eye part by detecting the reflection light that passes through the split prism 108 by the CCD 110.

The optical path L1 will be described next. The optical path L1 configures the optical path of the OCT optical system, as described above, and is used in acquisition of the interference signal for generating the tomographic image of the subject eye 140. On the optical path 1, an X scanner 131, a Y scanner 132, and lenses 112 and 113 are disposed.

The X scanner 131 and the Y scanner 132 configure a scanning unit that scans a measurement light on the fundus Er of the subject eye 140. The X scanner 131 and the Y scanner 132 are driven by a Galvano motor, which is not illustrated, that is controlled by the control unit 200. The X scanner 131 is used for scanning the measurement light in the X-direction, and the Y scanner 132 is used for scanning the measurement light in the Y-direction. Note that the X scanner 131 and the Y scanner 132 can be configured using arbitrary polarization mirrors, such as galvanometer mirrors. In the present example, a scanning unit is configured by the X scanner 131 and the Y scanner 132, but the configuration of the scanning unit is not limited to this configuration. The scanning unit may be configured by a polarization mirror that can polarize a light in a two-dimensional direction with a single mirror, such as a MEMS mirror.

The lens 112 is a focusing lens that is used for the purpose of focusing adjustment of a measurement light that is emitted from an optical fiber 115 of the OCT measurement optical system to the fundus Er of the subject eye 140. The lens 112 is driven in an optical axis direction of the measurement light illustrated by an arrow in the drawing by a motor, which is not illustrated, that is controlled by the control unit 200. The focusing adjustment causes a return light from the fundus Er to form an image in a spot shape on a tip end of the optical fiber 115 to be incident at the same time. Note that the optical fiber 115, the respective optical members disposed on the optical path L1, the dichroic mirrors 102 and 103, the objective lens 101, and the like, configure an OCT measurement optical system through which the measurement light propagates in the OCT optical system.

The optical fiber 115 is connected to an optical coupler 119. To the optical coupler 119, the optical fiber 115 of the OCT measurement optical system, an optical fiber 116 that is connected to a light source 114, an optical fiber 117 of an OCT reference optical system, and an optical fiber 118 that is connected to a spectroscope 123 are connected. The optical coupler 119 functions as a divider that divides light from the light source 114 into a measurement light and a reference light, and an interference unit that causes a return light of the measurement light from the subject eye 140 and the reference light to interfere with each other, and to generate an interference light.

The light source 114 is Super Luminescent Diode (SLD) that is a typical low coherent light source. In the present example, as the light source 114, a light source with a center wavelength of a light that is emitted of 855 nm, and a wavelength band width of approximately 100 nm is used. Note that the configuration of the light source 114 is not limited to this configuration, and an arbitrary light source can be used in accordance with a desired configuration.

The light emitted from the light source 114 is divided into the measurement light that propagates through the OCT measurement optical system including the optical fiber 115, and so on, via the optical coupler 119 through the optical fiber 116, and the reference light that propagates through the OCT reference optical system including the optical fiber 117, and so on. The measurement light is irradiated to the fundus Er of the subject eye 140 that is an object to be observed through the optical path L1 of the aforementioned OCT optical system, and reaches the optical coupler 119 through the same optical path as the return light, by reflection and scattering by a retina.

Meanwhile, the reference light reaches a reference mirror 122 to be reflected via the optical fiber 117, a lens 120, and a dispersion compensating glass 121 that is inserted to adjust dispersion of measurement light and the reference light. Subsequently, the reference light returns on the same optical path, and reaches the optical coupler 119. Here, the optical fiber 117, the lens 120, the dispersion compensating glass 121 and the reference mirror 122 configure the OCT reference optical system.

The return light of the measurement light from the subject eye 140 and the reference light are combined by the optical coupler 119 to be interference light. When an optical path length of the measurement light and an optical path length of the reference light are in a substantially equal state, the return light of the measurement light and the reference light interfere with each other and become an interference light. The reference mirror 122 is held to be adjustable in the optical axis direction of the reference light, illustrated by an arrow in the drawing, by a motor and a drive mechanism, which are not illustrated, that are controlled by the control unit 200, and can adjust the optical path length of the reference light to the optical path length of the measurement light that changes in accordance with a measured portion of the subject eye 140. The interference light is guided to the spectroscope 123 via the optical fiber 118.

In the spectroscope 123 (the light detection unit), lenses 124 and 126, a diffraction grating 125, and a line sensor 127 are provided. The interference light that is emitted from the optical fiber 118 becomes a substantially parallel light via the lens 124, and, thereafter, is divided by the diffraction grating 125, and is caused to form an image on the line sensor 127 by the lens 126. The line sensor 127 is shown as an example of a light receiving element that receives the interference light, generates an output signal corresponding to the interference light, and outputs the output signal. The control unit 200 can acquire information concerning a section of the fundus Er of the subject eye 140, based on the signal generated by the line sensor 127, and can generate a tomographic image of the fundus Er.

Configuration of Control Unit 200

Figure 3:
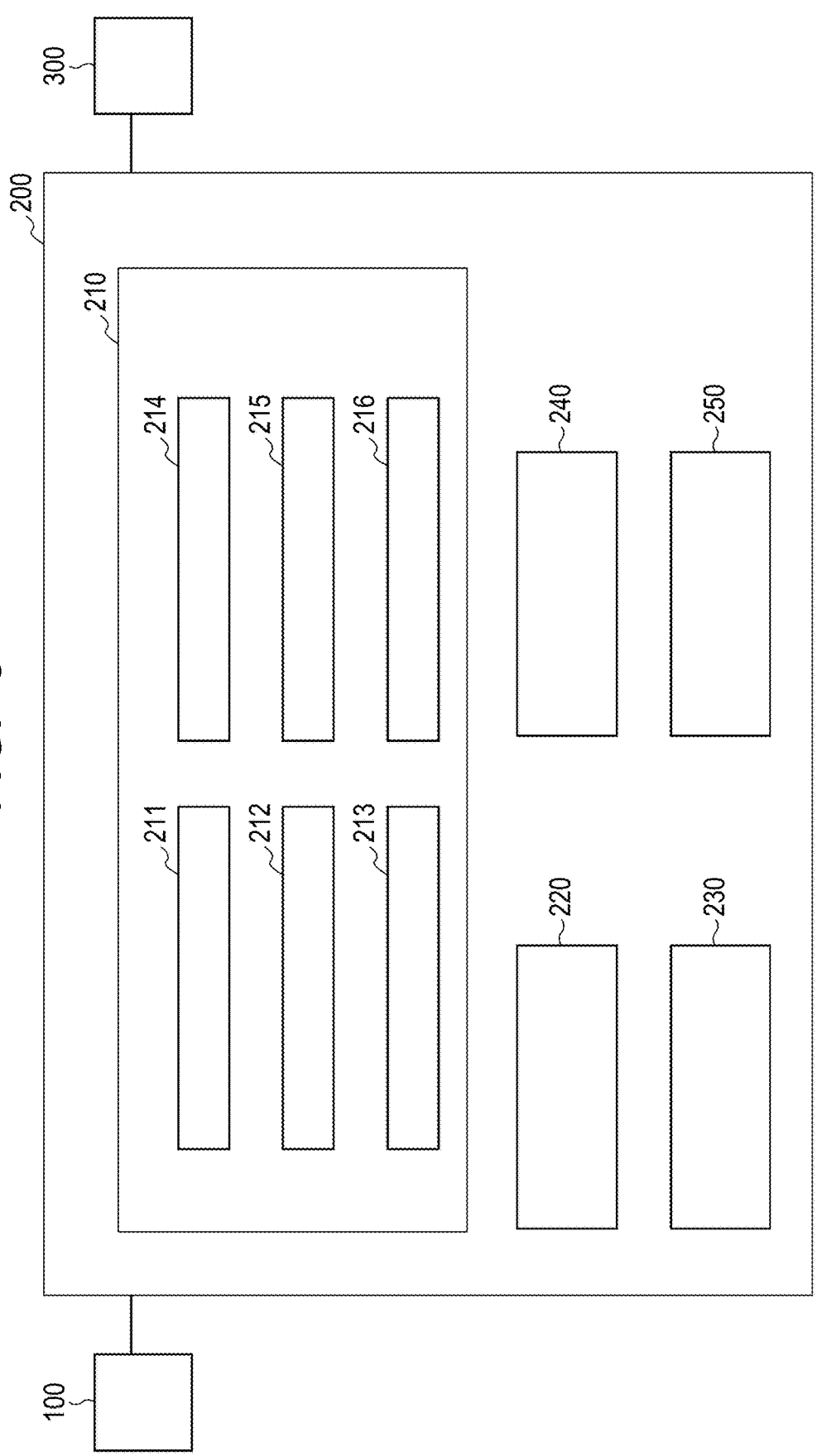
FIG. 3 illustrates a schematic configuration of a control unit according to example 1.

A configuration of the control unit 200 will be described with reference to FIG. 3. FIG. 3 is a block diagram illustrating a schematic configuration of the control unit 200. In the control unit 200, an image generation unit 210, an acquiring unit 220, a drive control unit 230, a storage unit 240, and a display control unit 250 are provided.

The acquiring unit 220 acquires various signals from the CCDs 110 and 111 and the line sensor 127 of the imaging optical system 100. Further, the acquiring unit 220 can also acquire a signal after Fourier conversion that is generated based on an interference signal, a signal obtained by applying some kind of signal processing to the signal after Fourier conversion, and the like, from a tomographic image generation unit 213.

In the image generation unit 210, an anterior eye image generation unit 211, a fundus image generation unit 212, the tomographic image generation unit 213, a region determination unit 214, a calculation unit 215, and an estimation unit 216 are provided.

The anterior eye image generation unit 211 generates an anterior eye image of the subject eye 140 based on a signal from the CCD 110 that is acquired by the acquiring unit 220. The fundus image generation unit 212 generates a fundus image of the subject eye 140 based on a signal from the CCD 111 that is acquired by the acquiring unit 220.

The tomographic image generation unit 213 generates a tomographic image of the subject eye 140 based on an interference signal from the line sensor 127 that is acquired by the acquiring unit 220. More specifically, the tomographic image generation unit 213 subjects the interference signal obtained from the line sensor 127 by the aforementioned series of processing to Fourier conversion, and converts the signal after the Fourier conversion into luminance or density information. Thereby, the tomographic image generation unit 213 acquires a tomographic image in a depth direction (a Z-direction) in a certain point in the fundus Er of the subject eye 140. A scan method like this is called A scan, and the tomographic image that is obtained is called an A scan image.

A plurality of A scan images can be acquired by repeatedly performing A scan like this while scanning the measurement light in a predetermined transverse direction of the fundus Er by the X scanner 131 and the Y scanner 132. For example, when the measurement light is scanned in the X direction by the X scanner 131, a tomographic image in an XZ plane is obtained, and, when, the measurement light is scanned in the Y-direction, a tomographic image in a YZ plane is obtained. A method of scanning the fundus Er of the subject eye 140 in the predetermined transverse direction like this is called B scan, and a tomographic image that is obtained is called a B scan image.

Further, the tomographic image generation unit 213 generates a tomographic image in which noise is reduced using a calculation value that is calculated by the calculation unit 215. Further, the tomographic image generation unit 213 generates a high-contrast tomographic image using a calculation value that is calculated by the calculation unit 215 and an estimation value that is estimated by the estimation unit 216.

The region determination unit 214 determines a target region in which a signal intensity is low (a region in which contrast is reduced) based on the tomographic image that is generated by the tomographic image generation unit 213. Note that the region determination unit 214 may determine the target region based on a signal after Fourier conversion that is acquired by the acquiring unit 220, or the like.

The calculation unit 215 calculates a calculation value in each pixel position, based on a plurality of tomographic images generated by the tomographic image generation unit 213. In the present example, the calculation unit 215 calculates an addition average value (an arithmetic mean value) of luminance values in the respective pixel positions of a plurality of tomographic images as a calculation value. The calculation value is not limited to the addition average value, and may be, for example, a median value, a mode value, a maximum value, or the like. The calculation unit 215 may calculate calculation values in the respective pixel positions based on signals after Fourier conversion that are acquired by the acquiring unit 220, or the like.

The estimation unit 216 performs MAP estimation processing on a plurality of tomographic images that are generated by the tomographic image generation unit 213, and estimates an estimation value of a true value of an interference signal. The estimation unit 216 may estimate an estimation value in each pixel position based on the signal after Fourier conversion that is acquired by the acquiring unit 220, or the like.

The drive control unit 230 controls drive of the respective components of the imaging optical system 100, such as the light source 114, the X scanner 131, and the Y scanner 132. The storage unit 240 stores various images generated by the image generation unit 210, information on a subject that is input, programs configuring the control unit 200, and the like. The display control unit 250 controls the display unit 300 and causes the display unit 300 to display various images, the information on the subject, and the like, that are stored in the storage unit 240.

The respective components of the control unit 200 can be configured by modules that are executed by a central processing unit (CPU) and a microprocessing unit (MPU) of the control unit 200. Further, the respective components of the control unit 200 may be configured by circuits, or the like, that realize specific functions such as an application specific integrated circuit (ASIC). The storage unit 240 can be configured using an arbitrary storage device and a storage medium, such as a memory, and an optical disk.

Image Process of Tomographic Image

Figure 4A:
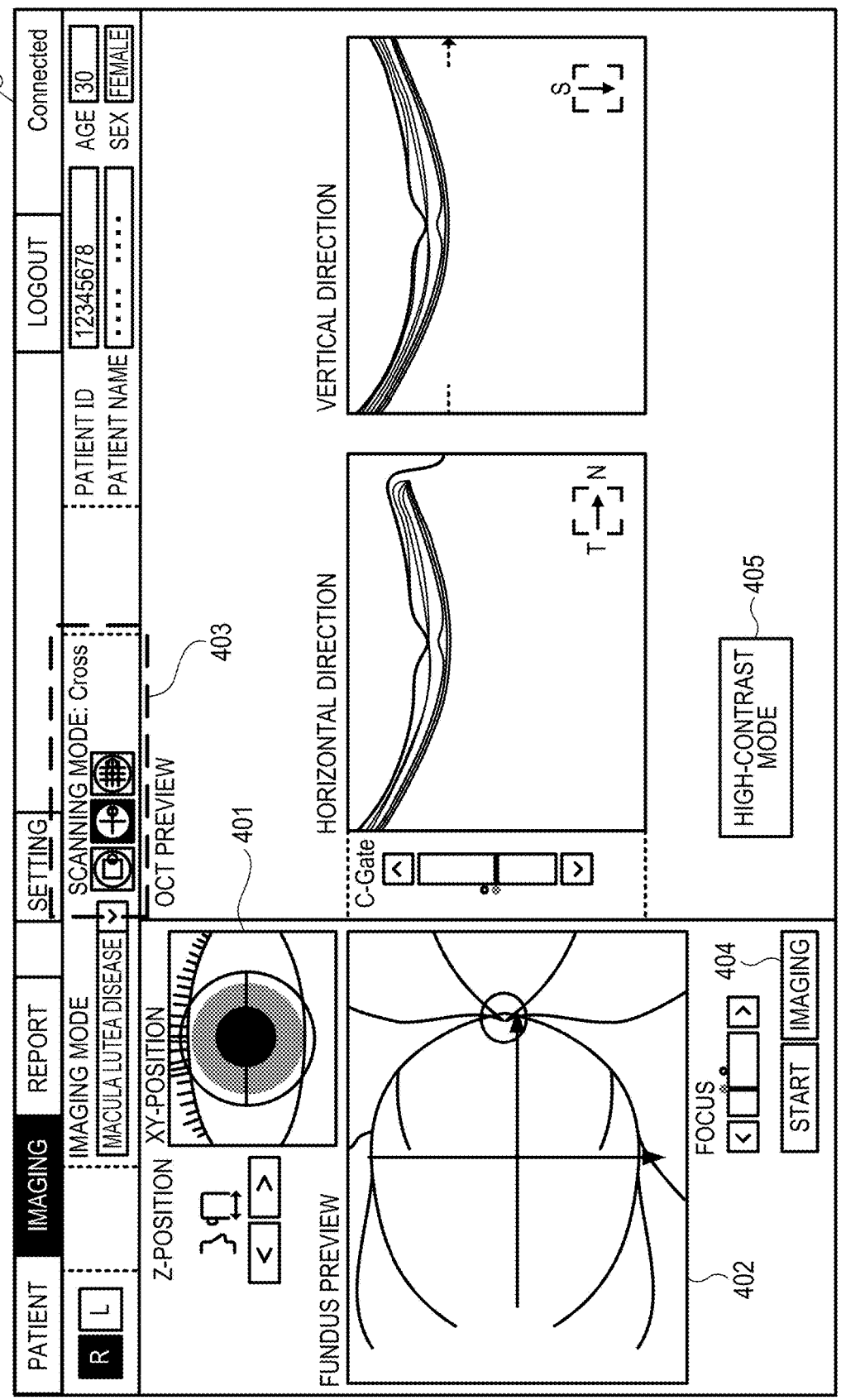
FIG. 4A illustrates an example of a display screen of a display unit according to example 1.

Hereafter, an imaging process of a tomographic image according to the present example will be described with reference to FIGS. 4A to 9. FIG. 4A illustrates an example of a preview screen 400 of a graphical user interface (GUI) for control/image display that is displayed by the display unit 300. FIG. 4B illustrates an example of a report screen 406 of the GUI for control/image display displayed by the display unit 300. The preview screen 400 illustrated in FIG. 4A is a screen that is displayed to perform instruction to start imaging, alignment adjustment of the imaging optical system 100, adjustment of a position of a site to be imaged, and the like. Meanwhile, the report screen 406 illustrated in FIG. 4B is a screen that displays high-resolution tomographic images 407 and 408 that are generated by imaging. In the present example, a function of generating a high-contrast tomographic image can be used by pressing a high-contrast mode button 405 on the preview screen 400 illustrated in FIG. 4A using input equipment, which is not illustrated, and turning on a high-contrast mode.

In the present example, after imaging preparation is made on the preview screen 400 illustrated in FIG. 4A, the fundus Er of a subject is imaged using the OCT apparatus 1. Specifically, a face of a subject is placed on a face receiving portion of the imaging optical system 100, and alignment of the imaging optical system 100 to the subject eye 140 is performed so that a measurement light enters a pupil of the subject eye 140. In the present example, an examiner moves the imaging optical system 100 in the X, Y, and Z-directions using a drive stage not illustrated while watching an anterior eye image 401 on the preview screen 400 and a fundus image 402 displayed in a fundus preview, and performs alignment of the imaging optical system 100. Alignment of the imaging optical system 100 to the subject eye 140 may be performed by analyzing the anterior eye image 401, and the like, and controlling drive of the imaging optical system 100 based on the analysis result, by the control unit 200.

Next, a scan mode for imaging substantially the same spot a plurality of times, which is displayed in a scan mode 403, is selected, and an imaging button 404 or an imaging button annexed to the imaging optical system 100 is pressed to start imaging.

Figure 5:
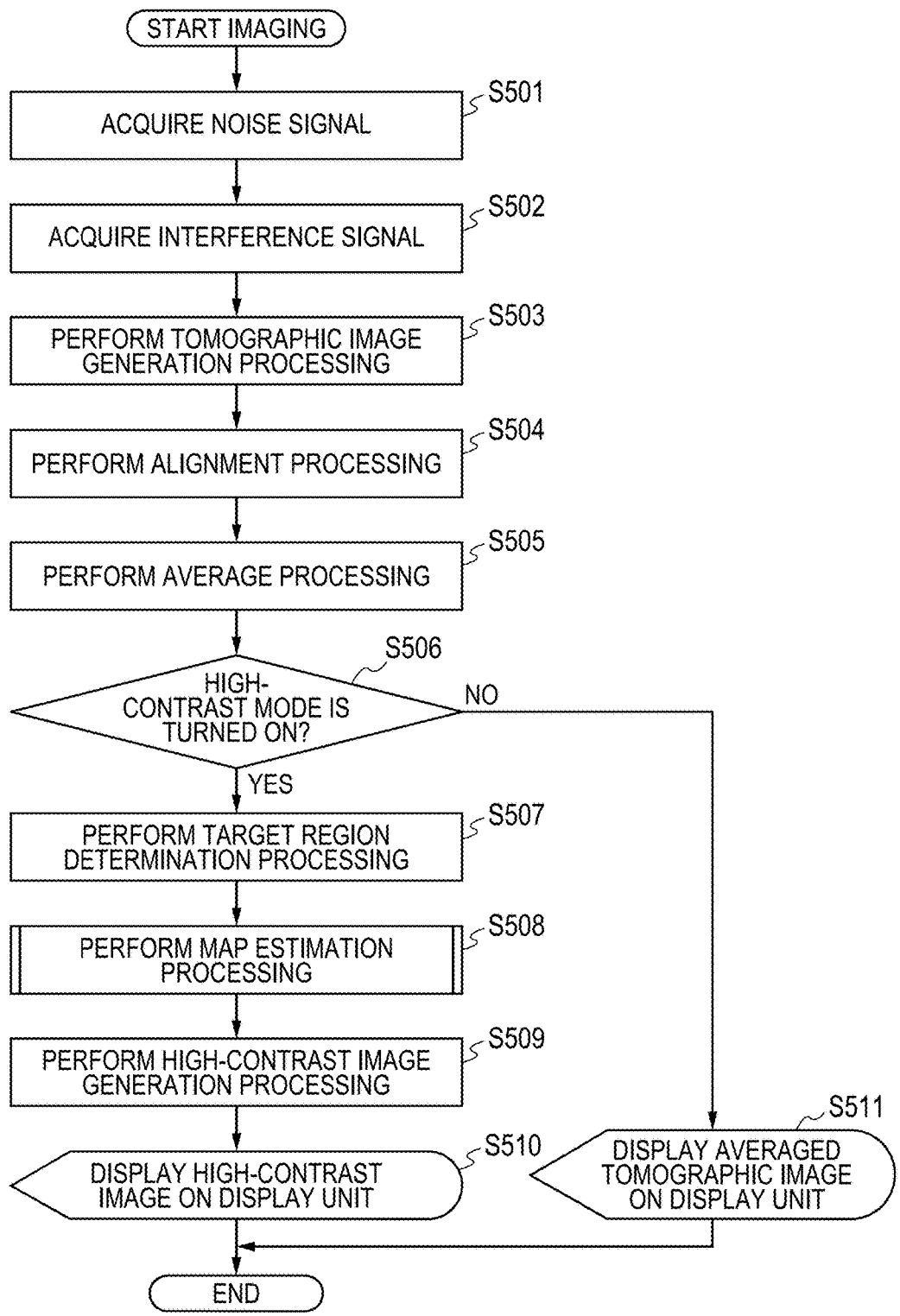
FIG. 5 illustrates a flowchart of a tomographic image imaging process according to example 1.

FIG. 5 illustrates a flowchart of an imaging process of a tomographic image according to the present example. When imaging is started, the process proceeds to step S501. In step S501, the tomographic image generation unit 213 acquires background data as a noise signal in the OCT optical system. The background data is acquired by acquiring a light signal of only the reference light by shielding the return light of the measurement light, for example. The tomographic image generation unit 213 may acquire noise information of the background data, and the like, that is measured in advance for each apparatus, and is stored in the storage unit 240.

In step S502, substantially a same spot (scanning line) of the fundus Er of the subject eye 140 is imaged N times by the imaging optical system 100. Specifically, the drive control unit 230 controls the respective components of the imaging optical system 100, and an optical coherence tomographic image of substantially the same spot of the subject eye 140 is picked up N times. Thereby, the acquiring unit 220 acquires N sets of interference signals, which are obtained by B scan of N times. In the present example, N=50 is set, and optical coherence tomographic image is imaged 50 times, but the number of imaging times is not limited to 50 times. The number of imaging times, which is N, may be an arbitrary number of two or more, so that a desired number of tomographic images for performing MAP estimation processing and addition average processing of tomographic images are obtained. Further, hereafter, a set of interference signals corresponding to B scan of one time will be referred to as one set of interference signals. Note that substantially the same spot includes not only completely the same spot, but also a spot slightly deviating from the same spot.

In step S503, the tomographic image generation unit 213 generates one tomographic image based on each set of interference signals acquired in the acquiring unit 220, and generates N tomographic images in total. The tomographic image generation unit 213 subjects a set of interference signals acquired in the acquiring unit 220 to Fourier conversion, and converts the signals after the Fourier conversion into luminance or density information to generate one tomographic image. Generation processing of a tomographic image may be performed by an arbitrary processing method that is already known.

Next, in step S504, the tomographic image generation unit 213 performs alignment using characteristics, and the like, in the tomographic images, such as fundus shapes, with respect to N tomographic images of the fundus Er at substantially the same spot that are acquired.

Specifically, the tomographic image generation unit 213 selects arbitrary one of the N tomographic images as a template. For example, the tomographic image generation unit 213 can select the tomographic image that is generated first as the tomographic image that is selected as the template. Further, the tomographic image generation unit 213 calculates correlations in all combinations with one another in the N tomographic images, obtains a sum of correlation coefficients for each frame, and may select the tomographic image in which the sum is maximum as the template.

Next, the tomographic image generation unit 213 collates each tomographic image with the template, and obtains a positional deviation amount (δX, δY, δθ) for each tomographic image. Here, δX represents a deviation amount in the X-direction, δY represents a deviation amount in the Y-direction, and δθ represents a deviation amount in a rotation direction. Specifically, the tomographic image generation unit 213 calculates Normalized Cross-Correlation (NCC) that is an index expressing similarity to each frame while changing a position and an angle of the template. The tomographic image generation unit 213 obtains a difference in position between the tomographic image that is collated and the template at the time of the calculated value of NCC becoming maximum, as the positional deviation amount. The index expressing similarity among images can be a barometer expressing similarity in the characteristics in the image of the frame that is collated and the template image, and various changes can be made to an arbitrary index indicating such a barometer.

The tomographic image generation unit 213 performs alignment of the tomographic images by applying positional correction to N−1 tomographic images other than the template in accordance with the obtained positional deviation amounts (δX, δY, δθ). There may be a case in which an image that is not aligned is acquired at the time of performing alignment of the images using a fundus shape, such as a case in which the eye of a subject moves greatly. In the case like this, processing of the image that is not aligned is properly stopped, and processing is advanced by decreasing the number of tomographic images for use in the following processing. As an alternative, the same number of tomographic images as the number of tomographic images the processing of which is stopped are additionally acquired, and alignment may be performed for the additional tomographic images. When coordinates of the pixels in the respective images are the same as a result of alignment of N tomographic images being carried out, the positions of the fundus Er displayed in the pixels also become the same position. After alignment of the tomographic images is ended, the process proceeds to step S505.

In step S505, the calculation unit 215 calculates calculation values of N pixel values for each pixel with respect to the N tomographic images that are aligned, and the tomographic image generation unit 213 generates a tomographic image that is averaged (an averaged tomographic image) using the calculation values that are calculated as representative values of the respective pixels. The storage unit 240 stores the averaged tomographic image that is generated. In the present example, the calculation unit 215 calculates calculation values by adding and averaging the luminance values of the pixel positions in the N tomographic images, corresponding to the respective pixel positions of the averaged tomographic image that is generated. Subsequently, the tomographic image generation unit 213 generates the averaged tomographic image using the calculated calculation values as luminance values (pixel values) in the respective pixel positions. As described above, the calculation value may be a median value, a mode value, a maximum value, or the like, without being limited to the one obtained by addition average (arithmetic mean value).

Figure 6A:
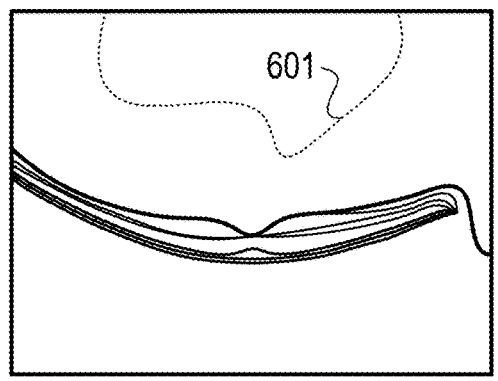
FIG. 6A is a view for describing the tomographic image imaging process according to example 1.
Figure 6B:
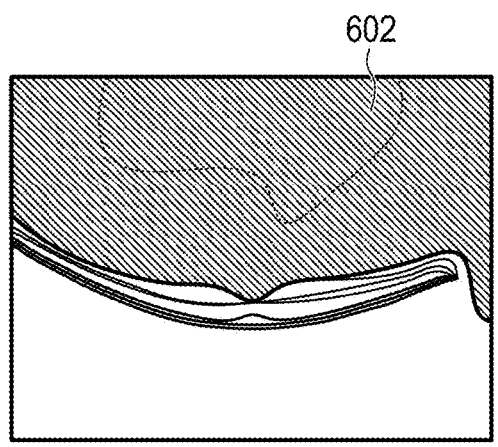
FIG. 6B is a view for describing the tomographic image imaging process according to example 1.

FIG. 6A illustrates an example of the averaged tomographic image that is generated. In the generated averaged tomographic image, a region in which the signal intensity is low is expressed in a state with low contrast as described above. Consequently, in the averaged tomographic image illustrated in FIG. 6A, a vitreous body 601 is displayed in a state with low contrast. When the averaged tomographic image is generated in step S505, the process proceeds to step S506.

In step S506, the tomographic image generation unit 213 determines whether or not the high-contrast mode is turned on. When the tomographic image generation unit 213 determines that the high-contrast mode is not turned on, the display control unit 250 causes the display unit 300 to display the averaged tomographic image that is stored in the storage unit 240 in step S505, in step S511 to end the imaging process. When the tomographic image generation unit 213 determines that the high-contrast mode is turned on in step S506, the process proceeds to step S507.

In step S507, the region determination unit 214 performs segmentation processing on the averaged tomographic image, and determines the vitreous body region that is the region in which the signal intensity is low, as a target region. Specifically, the region determination unit 214 generates images by applying a median filter and a Sobel filter respectively to the averaged tomographic image (hereafter, the respective images are also referred to as a median image and a Sobel image). Next, the region determination unit 214 generates profiles for each data corresponding to A scan from the median image and the Sobel image that are generated. The profiles that are generated are a profile of a luminance value in the median image, and a profile of a gradient in the Sobel image. Subsequently, the region determination unit 214 detects peaks in the profiles generated from the Sobel image. The region determination unit 214 extracts boundaries of respective regions of a retina layer by referring to the profile of the median image corresponding to before and after the peaks that are detected and between the peaks.

In the present example, the region determination unit 214 extracts an internal limiting membrane (ILM) by the segmentation processing. The region determination unit 214 determines that an opposite side (a pupil side) to the retina, of the ILM boundary is the vitreous body, and determines a region (a region 602 illustrated by oblique lines in FIG. 6B) at the pupil side from the ILM boundary as a vitreous body region that is known as the region in which the signal intensity is low. Thereby, the region determination unit 214 determines the vitreous body region as a target region for which MAP estimation is performed with respect to a pixel value.

The region determination unit 214 may perform segmentation processing on one of the N tomographic images, determine a region in which the signal intensity is low, and determine the region as the target region. Further, the segmentation processing may be performed using an arbitrary known method other than the method described above. Further, in the present example, the vitreous body region is determined as the target region, but an arbitrary region, such as a choroid membrane region, that is known as a region in which the signal intensity is low, may be determined as the target region. In this case, the region determination unit 214 determines a layer of the choroid membrane, or the like, by the segmentation processing, and determines the layer as the target region. Further, a plurality of regions, such as a vitreous body region and a choroid membrane region, may be determined as the target region.

Next, in step S508, the estimation unit 216 performs MAP estimation processing with respect to the determined target region, and estimates estimation values in respective pixel positions in the target region. Hereafter, the MAP estimation according to the present example will be described with reference to FIG. 7. FIG. 7 illustrates a flowchart of the MAP estimation processing according to the present example.

When the MAP estimation processing is started in step S701, the estimation unit 216 calculates noise variance $\sigma^2$ based on the noise signal acquired in step S501.

Next, in step S702, the estimation unit 216 uses the following expression 1 and the calculated noise variance $\sigma^2$ to calculate a probability density of a signal intensity a that is measured, to a true signal intensity $\sigma^2$, and generates a probability density map of the signal intensity a, which is measured, to the true signal intensity $\sigma^2$.

$$p(a_n | v, \sigma^2) = \frac{a_n}{\sigma^2} \exp\left(\frac{-(a_n^2 + v^2)}{2\sigma^2}\right) I_0\left(\frac{a_n v}{\sigma^2}\right) \quad \text{(expression 1)}$$

Here, expression 1 is a probability density function of a signal intensity that is measured, $a_n$ is a signal intensity in the pixel that is measured, v is a true signal intensity, $\sigma^2$ is variance of noise, and $I_o$ is a modified Bessel function of the first kind. Note that, in the present example, as the signal intensity that is measured, the pixel values (luminance values) of the pixels in a tomographic image are used. Here, n indicates an index of signal intensity of a processing target, and, in the case of the first signal intensity, n=1.

Figure 8:
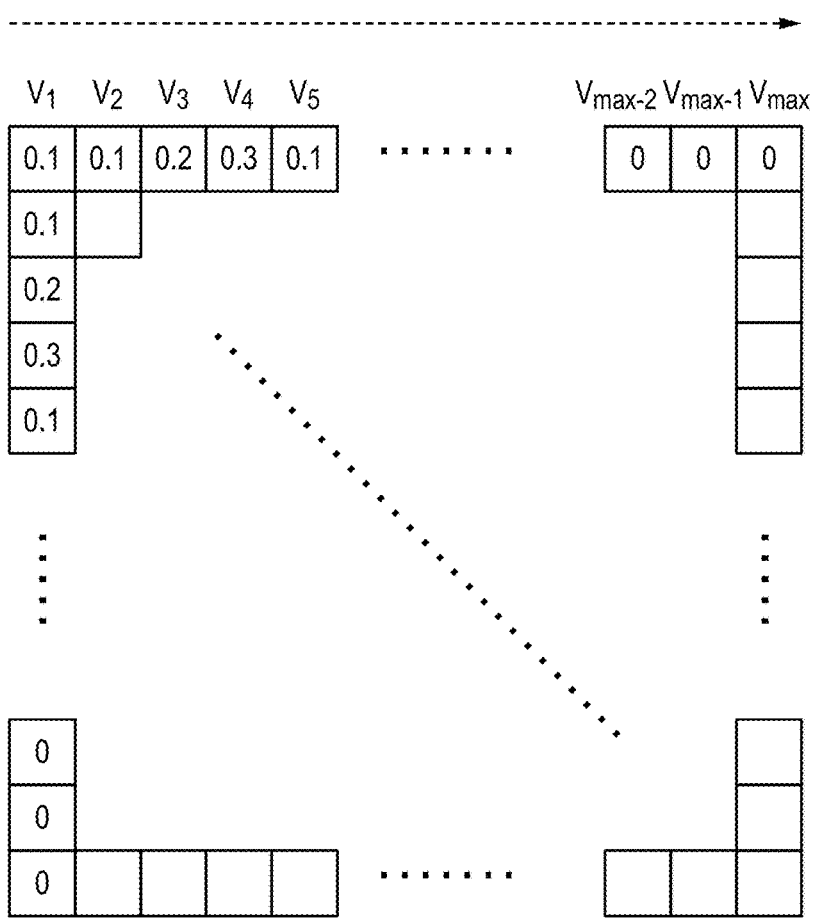
FIG. 8 illustrates an example of a probability density map.

FIG. 8 illustrates an example of a probability density map of a signal intensity A that is measured, with respect to the true signal intensity v. Here, the signal intensity A indicates a value of the signal intensity a, which is measured, and $A_1$, $A_2$, or the like, does not indicate a signal intensity corresponding to an index of the signal intensity of the measurement target, but indicates a signal intensity for each increment. That is, for example, $A_1$ and $A_2$ do not indicate the signal intensities of the first and the second measurement targets like $a_1$ and $a_2$, but $A_2$ indicates a value obtained by adding a value corresponding to the increment to $A_1$. Further, the increments of parameters of v and A in the probability density map (the increments of $v_1$ to $v_2$, etc., and the increments of $A_1$ to $A_2$, etc.) and ranges (a range of $v_1$ to $v_{max}$, and a range of $A_1$ to $A_{max}$) are set in advance so as to have a sufficient gradation and dynamic range with respect to a tomographic image that is acquired.

The estimation unit 216 substitutes v and A separated at each increment that is set, and the calculated noise variance $\sigma2$ into expression 1, and generates a probability density map of the signal intensities corresponding to v and A that are substituted. Here, the signal intensity A is substituted as $a_n$ into expression 1. In the present example, the estimation unit 216 obtains a probability density by successively changing the value of A with respect to the value of v, and generates the probability density map by disposing the probability densities in a direction of a solid arrow in the probability density map illustrated in FIG. 8. The estimation unit 216 may obtain the probability density by successively changing the value of v with respect to the value of A, and generate the probability density map by disposing the probability densities in a direction of a broken line arrow of the provability density map illustrated in FIG. 8.

Next, in step S703, the estimation unit 216 sets an initial position of a pixel position (coordinates (x, z)) at a time of starting MAP estimation. Here, the coordinates (x, z) show coordinates in a tomographic image that is high-contrast (a high-contrast tomographic image) to be generated, x represents a position in a B scan direction in the tomographic image, and z represents a position in a depth direction in the tomographic image. Note that the respective coordinates in the high-contrast tomographic image to be generated correspond to respective coordinates in the averaged tomographic image and the N tomographic images that are already aligned. As described above, the estimation unit 216 performs MAP estimation with respect to the pixels in the target region that is determined in the region determination unit 214, so that the initial position may be an arbitrary position as long as it is a position within the target region. For example, the estimation unit 216 sets coordinates with the values of x and z being the smallest in the target region, as the initial position.

Next, in step S704 to step S706, the estimation unit 216 extracts a probability density with the true signal intensity v as a parameter with respect to each of the signal intensities an in the coordinates (x, z) of the first to the Nth tomographic images, from the probability density map. Thereafter, the estimation unit 216 calculates a probability density function with the true signal intensity v as the parameter, from the extracted probability densities. Here, the probability density function with the true signal intensity v as the parameter corresponds to a line in the example of the probability density map illustrated in FIG. 8. For example, the probability density function with the true signal intensity v as the parameter refers to a function in which a probability=0.2 is derived with respect to a value $v_3$ of the signal intensity v, and a probability=0.3 is derived with respect to $v_4$, when the value of the signal intensity $a_n$ is $A_1$, in the example illustrated in FIG. 8. Note that nmax in the drawing corresponds to N.

In the present example, the estimation unit 216 extracts the probability density along the direction of the broken arrow of the probability density map illustrated in FIG. 8, with respect to the signal intensity an in the coordinates (x, z) of the nth tomographic image that is the processing target. When there are tomographic images for which stop of the processing is determined at the time of alignment, the estimation unit 216 extracts the probability densities with respect to the tomographic images in the number except for the number of tomographic images for which stop of the processing is determined. When the estimation unit 216 extracts the probability densities of the true signal intensity v with respect to the signal intensity $a_n$ in the coordinates (x, z) of the N tomographic images, and calculates the probability density function with the true signal intensity v as the parameter, the process proceeds to step S707.

In step S707, the estimation unit 216 calculates product of the probability density functions of the true signal intensity v, concerning N of the measured signal intensities from the signal intensities $a_1$ to $a_N$, and determines the calculated product as a likelihood function. Here, the product of the probability density functions will be described with reference to FIG. 8. For example, when the measured signal intensity a1 is the signal intensity A1, and a signal intensity $a_2$ is the signal intensity A3, the probabilities of the true signal intensity v to the signal intensities $a_1$ and $a_2$ being $v_1$ are respectively 0.1 and 0.2, when the probability density map is referred to. Consequently, in this case, the probability of the true signal intensity v being $v_1$ is obtained as 0.1×0.2 that is a product of these probabilities. Probabilities of the true signal intensity v being $v_2$, $v_3$, . . . , and $v_{max}$ are respectively obtained in the same way. What is obtained by multiplying the respective probabilities for the true signal intensity v in the probability density functions of the measured signal intensities $a_1$ to $a_N$ is referred to as the product of the probability density functions. Consequently, the product of the probability density functions includes respective products of probabilities that the true signal intensities v to the measured signal intensities $a_1$ to $a_N$ are $v_1$, $v_2$, . . . , and $v_{max}$.

In step S708, the true signal intensity v, with which the probability becomes maximum in a posterior probability function (a representative probability density function) that is a product of the likelihood function calculated by the estimation unit 216 and a prior probability, is determined.

Here, when a uniform prior probability of always acquiring a signal is considered as the prior probability, and the prior probability is set as 1, the likelihood function directly becomes the posterior probability function. The estimation unit 216 determines a parameter (the true signal intensity v) at which the probability becomes maximum in the posterior probability function.

More briefly, in the present example, the estimation unit 216 extracts a probability density for each true signal intensity v with respect to the measured signal intensities $a_1$ to $a_N$ in steps S704 to S706. Thereafter, in step S707, the estimation unit 216 calculates the product of the probability density functions, which is found by multiplying the probability densities for each true signal intensity v extracted with respect to the respective signal intensities. Subsequently, the estimation unit 216 determines the true signal intensity v at which the probability becomes maximum in the calculated product of the probability density functions. In this way, the determined true signal intensity v becomes an estimation value estimated by the estimation unit 216.

In step S709, the estimation unit 216 causes the storage unit 240 to store the true signal intensity v determined in step S708 as the estimation value of the coordinates (x, z).

Thereafter, in step S710, the estimation unit 216 determines whether or not the estimation unit 216 estimates the estimation values with respect to all the pixel positions in the target region. When the estimation unit 216 determines that the estimation unit 216 does not estimate the estimation values with respect to all the pixel positions in the target region, the process proceeds to step S711. In step S711, the estimation unit 216 moves the pixel position (coordinates (x, z)) for which the estimation value is estimated within the target region, and thereafter, returns the process to step S704.

In step S710, when the estimation unit 216 determines that the estimation unit 216 estimates the estimation values with respect to all the pixel positions in the target region, the process proceeds to step S509.

In step S509, the tomographic image generation unit 213 overwrites the estimation values estimated by the MAP estimation processing by the estimation unit 216 as the pixel values in the respective pixel positions of the target region in the averaged tomographic image. Thereby, the tomographic image generation unit 213 can generate a high-contrast tomographic image having the pixel values based on the estimation values by the MAP estimation in the region in which the signal intensity is low. The storage unit 240 stores the high-contrast tomographic image that is generated.

Figure 6C:
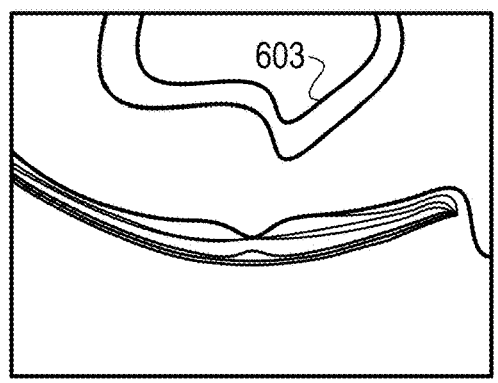
FIG. 6C is a view for describing the tomographic image imaging process according to example 1.

FIG. 6C illustrates an example of the high-contrast tomographic image that is generated. In the high contrast tomographic image illustrated in FIG. 6C, a vitreous body 603 is expressed in a high contrast state.

Figure 9:
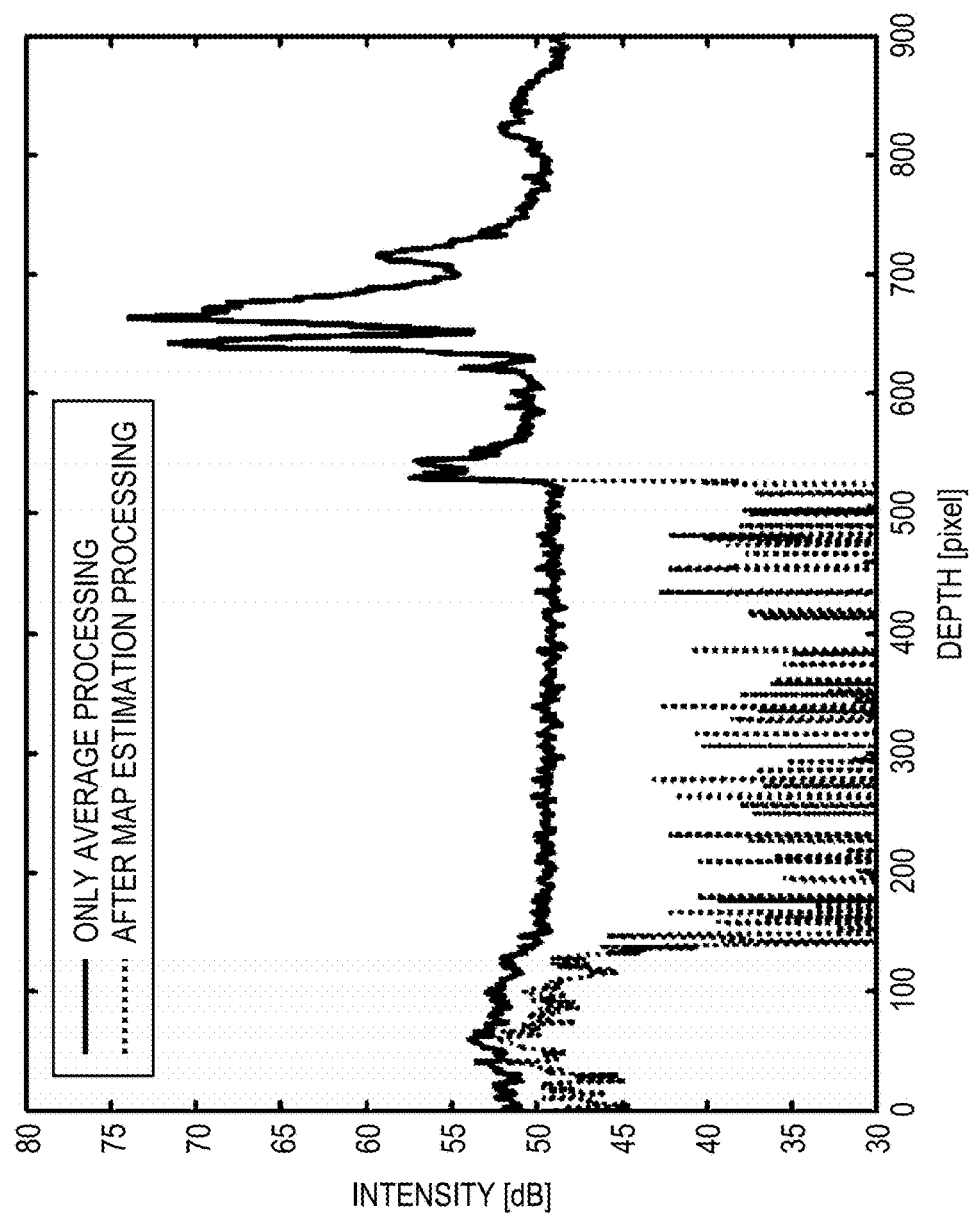
FIG. 9 illustrates an example of a profile of A scan data obtained by the tomographic image imaging process according to example 1.

Further, FIG. 9 illustrates an example of a profile of the signal intensity (luminance value) corresponding to A scan in the averaged tomographic image that is generated in step S505, and the high-contrast tomographic image that is generated in step S509. In FIG. 9, a profile concerning the signal intensity of the averaged tomographic image is illustrated by a solid line, and a profile concerning the signal intensity of the high-contrast image using MAP estimation processing is illustrated by a dotted line.

Referring to FIG. 9, in the averaged tomographic image, the signal intensity is high and contrast is low, in the vitreous body region in which the signal intensity is originally low. In contrast with this, it is understandable that in the high-contrast image using MAP estimation processing, high contrast is kept because the estimation value that is estimated as the true signal intensity is used in the vitreous body region in which the signal intensity is originally low.

In step S510, the display control unit 250 causes the display unit 300 to display the high-contrast tomographic image stored in the storage unit 240, and ends the imaging process.

In this way, the control unit 200 performs MAP estimation processing on only the vitreous body region in which the signal intensity is low, and performs average processing on other regions such as a retina in which the signal intensity is high. Thereby, the control unit 200 can carry out MAP estimation processing that requires a large amount of calculation limitedly to only the necessary region, and can generate a high-contrast image in a short time.

As described above, the control unit 200 according to the present example is an image processing apparatus that processes the tomographic image generated using a plurality of tomographic images acquired by performing optical coherence tomographic imaging a plurality of times using the measurement light that is controlled to scan substantially the same spot of the subject eye 140. The control unit 200 includes the acquiring unit 220 that acquires the information on a plurality of tomographic images. Further, the control unit 200 includes the image generation unit 210 including the tomographic image generation unit 213 that uses the information on a plurality of tomographic images, generates the representative values in the respective pixel positions of the tomographic image, and generates the tomographic image with the representative values in the respective pixel positions as the pixel values.

The image generation unit 210 includes the region determination unit 214 that determines the target region in which contrast reduces in a tomographic image using the information on a plurality of tomographic images. Further, the image generation unit 210 includes the calculation unit 215 that calculates the calculation values in pixel positions using information on a plurality of tomographic images corresponding to the pixel positions of the tomographic image, of the information on the plurality of tomographic images. Further, the image generation unit 210 includes the estimation unit 216 that estimates the estimation values by performing MAP estimation processing on the information on a plurality of tomographic images corresponding to pixel positions, of the information on the plurality of tomographic images, in the respective pixel positions of the target region. The tomographic image generation unit 213 of the image generation unit 210 generates a high-contrast tomographic image by setting the estimation values as the representative values in the target region and setting the calculation values as the representative values in the regions other than the target region in the tomographic image.

In regard to determination of the target region, specifically, the region determination unit 214 determines the layer boundaries of the fundus portion based on at least one tomographic image of the information on a plurality of tomographic images. Thereafter, the region determination unit 214 determines the target region from the determined layer boundaries and the structure of an eye.

In regard to MAP estimation processing, specifically, the estimation unit 216 uses a predetermined probability density function on the information on a plurality of tomographic images corresponding to the respective pixel positions of the target region, and calculates probability density functions of the information on the plurality of tomographic images corresponding to the pixel positions. Thereafter, the estimation unit 216 calculates the product of the probability density functions concerning the information on a plurality of tomographic signals corresponding to the same pixel position. Subsequently, the estimation unit 216 determines the information on the tomographic image in which the probability becomes maximum in the product of the probability density functions, and sets the value of the information on the determined tomographic image as the estimation value.

As described above, the control unit 200 according to the present example performs MAP estimation processing on only the target region in which the signal intensity is low, and performs average processing on the other regions, such as a retina, in which the signal intensity is high. Thereby, MAP estimation processing that requires a large amount of calculation is efficiently applied, and a tomographic image with greater contrast than an averaged image can be generated in a shorter amount of time than in the case of performing MAP estimation processing with respect to all the pixels.

In the present example, in the addition average processing, the region determination processing and the MAP estimation processing, the luminance value of the tomographic image is used as the signal intensity, but the signal intensity for use in these kinds of processing is not limited to the luminance value. The signals for use in these kinds of processing can be signals corresponding to the respective pixel positions, and, therefore, can be tomographic signals based on the signals after the interference signals acquired in the OCT optical system being subjected to Fourier conversion. The tomographic signals include, for example, a signal after the interference signal being subjected to Fourier conversion, a signal obtained by applying arbitrary signal processing for image generation to the signal after the Fourier conversion, and signals of a luminance value, and the like, based on these signals. In the present specification, a set of tomographic signals corresponding to one tomographic image is referred to as one set of tomographic signals, and sets of tomographic signals corresponding to a plurality of tomographic images are referred to as a plurality of sets of tomographic signals.

Further, in the present example, the example of imaging the fundus Er is illustrated, but an imaging target portion is not limited to the fundus Er, and may be an anterior eye portion. Further, in the present example, the configuration is described in which the region corresponding to the layer structure that is set in advance as the region in which the signal intensity is low is determined as the target region to which MAP estimation is applied. Setting of the layer structure and the tissue corresponding to the region that is determined as the target region is not limited, however, to the setting described above, but may be arbitrarily set in accordance with a desired configuration. For example, the layer structure and the tissue may be set using a GUI by an examiner, or may be set by a recommendation mode corresponding to a specific disease being selected.

In the present example, the region determination unit 214 determines the target region based on the averaged tomographic image, and the tomographic image generation unit 213 overwrites the pixel values to generate a tomographic image with high contrast, with the estimation values by MAP estimation as the representative values with respect to the target region. The configuration in which a high-contrast tomographic image is generated is not, however, limited to this configuration. For example, the target region is determined based on at least one tomographic image out of the N tomographic images that are acquired, and, with respect to the pixel values in the target region, only the MAP estimation processing is performed without performing average processing, and the estimation values may be set as the representative values.

Example 2

Hereafter, an OCT apparatus according to example 2 will be described with reference to FIGS. 10 and 11. The OCT apparatus according to the present example has a similar configuration to that of the OCT apparatus 1 according to example 1, so that the same reference signs are used with respect to the components, and an explanation thereof will be omitted. Hereafter, concerning the OCT apparatus according to the present example, a difference from the OCT apparatus 1 according to example 1 will be mainly described.

In the OCT apparatus 1 according to example 1, the target region for which MAP estimation is performed using the segmentation function is determined. In contrast with this, in the OCT apparatus according to the present example, a target region for which MAP estimation is performed is determined using a signal intensity for each pixel.

Further, in the OCT apparatus according to example 1, a high-contrast tomographic image is generated when the high-contrast mode is selected in advance. In contrast with this, in the OCT apparatus according to the present example, after the tomographic image generation unit 213 generates an averaged tomographic image, the display control unit 250 causes the display unit 300 to display the averaged tomographic image, and, thereafter, accepts an operation of whether or not to generate a high-contrast tomographic image.

Figure 10:
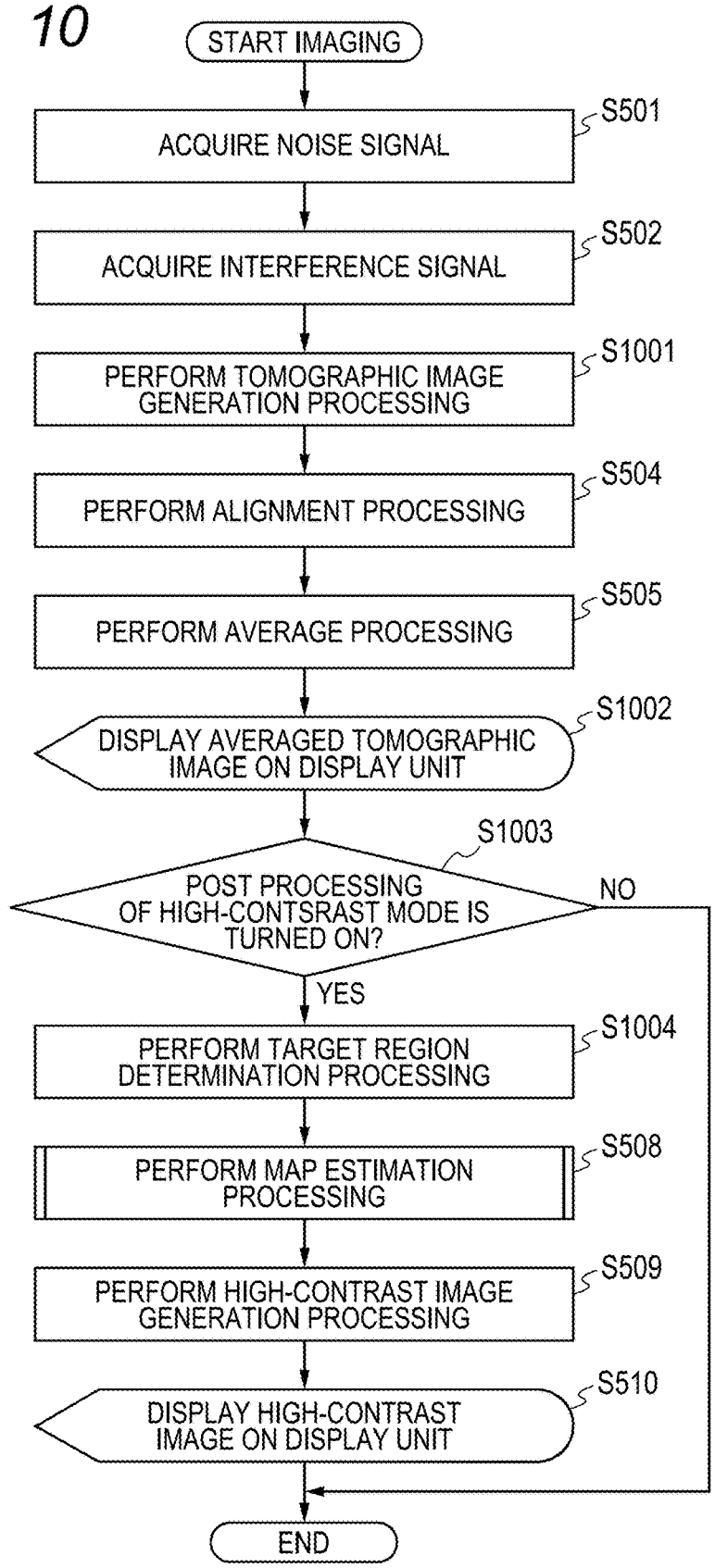
FIG. 10 illustrates a flowchart of a tomographic image imaging process according to example 2.
Figure 11:
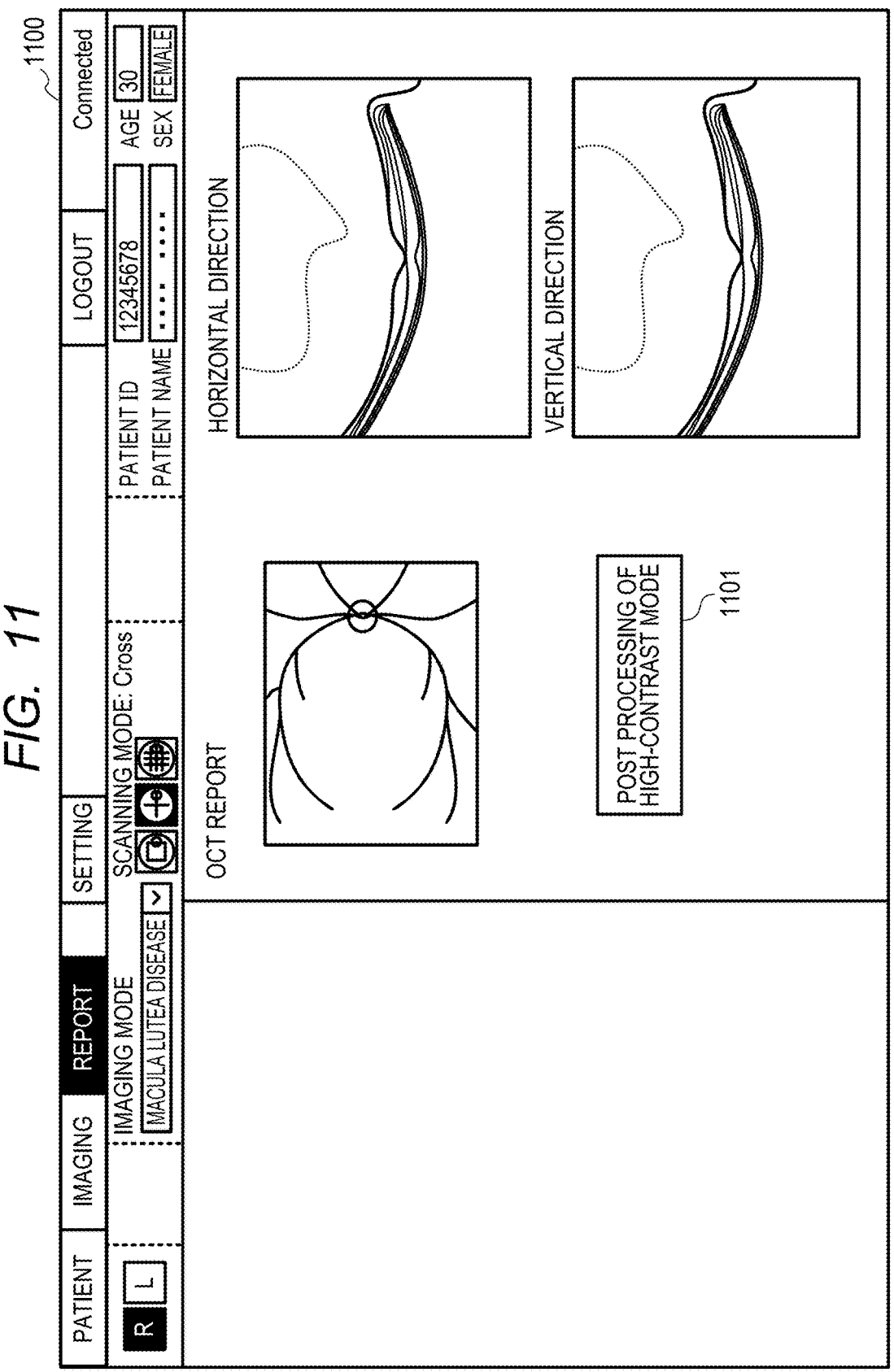
FIG. 11 illustrates an example of a display screen of a display unit according to example 2.

FIG. 10 illustrates a flowchart of an imaging process of a tomographic image according to the present example. The imaging process according to the present example is similar to the imaging process according to example 1 except for steps S1001 to S1004, so that explanation will be omitted concerning the similar processing. When the imaging process according to the present example is started, similar processing to the imaging process according to example 1 is performed in steps S501 and S502, and an interference signal is acquired in step S502.

When the interference signal is acquired, the tomographic image generation unit 213 generates N tomographic images in step S1001 as in step S503 of the imaging process according to example 1. Here, in step S1001, the storage unit 240 further stores the N tomographic images that are generated, for the purpose of post processing of the high-contrast mode. Thereafter, the same processing as in steps S504 and S505 of the imaging process according to example 1 is performed, and the tomographic image generation unit 213 generates an averaged tomographic image in step S505.

When the averaged tomographic image is generated, the display control unit 250 causes the display unit 300 to display the averaged tomographic image stored in the storage unit 240 in step S1002. FIG. 11 illustrates an example of a report screen 1100 displayed in the display unit 300 at this time. On the report screen 1100, a post processing button 1101 of the high-contrast mode is illustrated with the averaged tomographic image. When the post processing button 1101 of the high-contrast mode is pressed by the examiner with use of input equipment not illustrated, the post processing of the high-contrast mode is turned on.

Next, in step S1003, the tomographic image generation unit 213 determines whether or not the post processing button 1101 of the high-contrast mode is pressed, and the post processing of the high-contrast mode is turned on. When the tomographic image generation unit 213 determines that the post processing of the high-contrast mode is not turned on, the imaging process is ended.

In contrast with this, when the tomographic image generation unit 213 determines that the post processing of the high-contrast mode is turned on, the process proceeds to step S1004. In step S1004, the region determination unit 214 determines a target region using a histogram of the averaged tomographic image generated in step S505. In the present example, the pixel value of 10 percentile of the pixel values of all pixels included in the averaged tomographic image is set as a threshold value, and a region including pixels having pixel values equal to or less than the threshold value is determined as a target region. Thereby, the tomographic image generation unit 213 can determine the region including the pixels having low signal intensities as the target region.

In the present example, 10 percentile is adopted as the threshold value, but setting of the threshold value is not limited to 10 percentile. The threshold value may be arbitrarily set in accordance with a desired configuration. As the threshold value, the pixel value of an arbitrary percentile such as 20 percentile may be set, or a value that is a half of the value obtained by averaging the pixel values of all the pixels included in the averaged tomographic image may be set, for example.

When the target region is determined in step S1004, the process proceeds to step S508. The processing in step S508 and the following steps is the same as that in the imaging process according to example 1, and, therefore, an explanation thereof will be omitted.

In the OCT apparatus according to the present example, the region determination unit 214 determines the region of the pixel positions having calculation values less than the threshold value that is set using the calculation values calculated with respect to the respective pixel positions as the target region. In the OCT apparatus according to the present example, MAP estimation processing is performed to only the region in which the signal intensity is low, MAP estimation processing that requires a large amount of calculation is efficiently applied, and the tomographic image with greater contrast than the averaged image can be generated in a short time.

The region determination unit 214 may set the threshold value similarly to the present example using one tomographic image out of a plurality of tomographic images, and may determine a region having a tomographic signal value less than the set threshold value as the target region.

Further, in the OCT apparatus according to the present example, after display of the averaged tomographic image, the high-contrast mode can be selected by the examiner instructing the high-contrast mode from a GUI in accordance with necessity. Consequently, the examiner can generate a high-contrast tomographic image after confirming that the contrast is in a low state in the averaged tomographic image. Accordingly, occurrence of an unnecessary calculation time can be avoided in the case in which the averaged tomographic image is sufficient in accordance with a use purpose of the image and operability and convenience of the OCT apparatus can be increased. Concerning post processing of the high-contrast mode, application to the OCT apparatus 1 according to example 1 and the like can be also made.

Example 3

Hereafter, with reference to FIG. 12, an OCT apparatus according to example 3 will be described. The OCT apparatus according to the present example has a similar configuration to that of the OCT apparatus according to example 2, so that the same reference signs are used with respect to the components, and an explanation thereof will be omitted. Hereafter, concerning the OCT apparatus according to the present example, a difference from the OCT apparatus according to example 2 will be mainly described.

In the OCT apparatus according to example 2, the configuration is adopted, in which, for post processing of the high-contrast mode, the storage unit 240 stores all of the N tomographic images generated in step S1001. Usually, when generation of a tomographic image is performed, data is handled by floating point of 32 bit or 64 bit, and calculation with high precision is carried out. When a large number of tomographic images are always stored, however, if the tomographic images are stored in data having large bit numbers like these, a data storage device with a large capacity is required as the storage unit 240, causing an increase in cost.

Consequently, in the present example, pixel values in respective pixels of a tomographic image are subjected to gradation conversion, and the pixel values are stored as the data having low bit numbers, and processing of returning the gradation of the data is performed when MAP estimation is performed.

Figure 12:
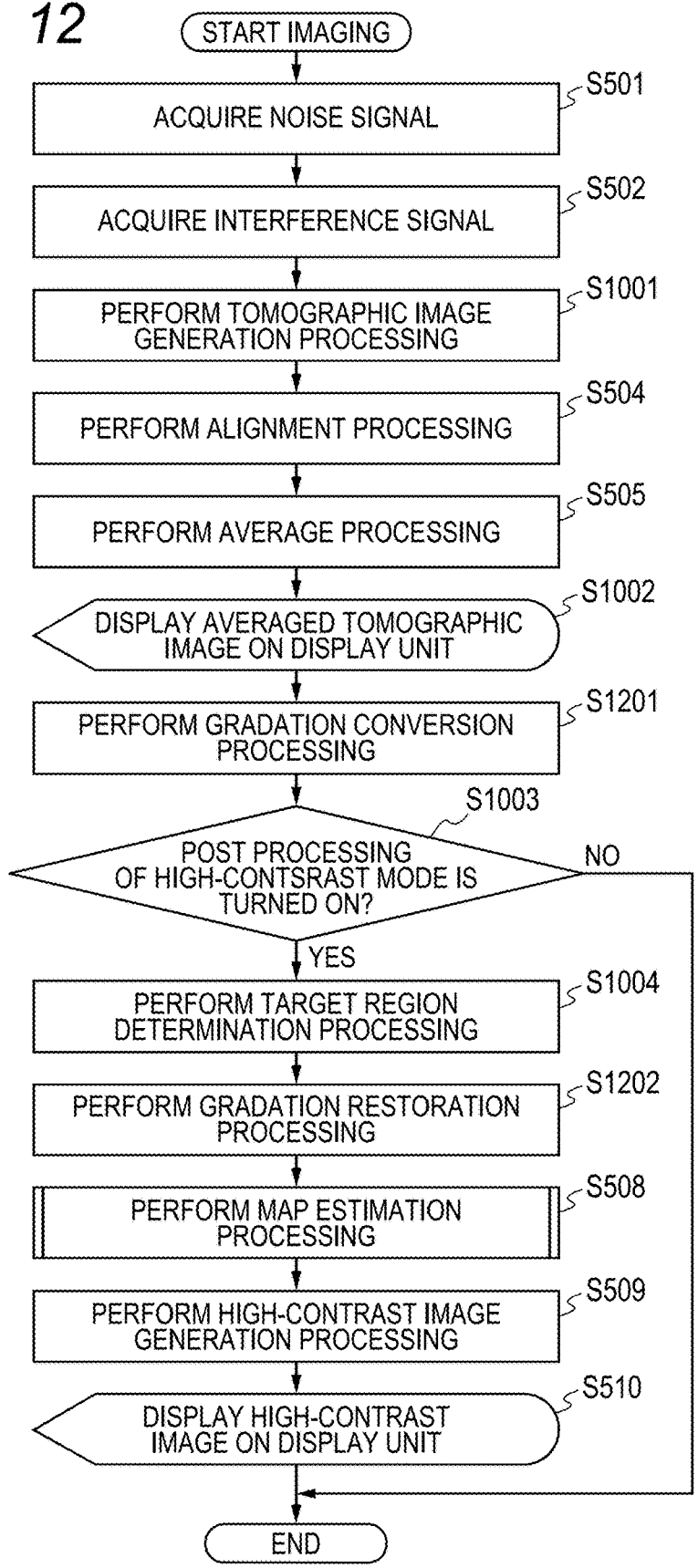
FIG. 12 illustrates a flowchart of a tomographic image imaging process according to example 3.

FIG. 12 illustrates a flowchart of an imaging process according to the present example. The imaging process according to the present example is similar to the imaging process according to example 2 except for steps S1201 and S1202, so that explanation will be omitted concerning the similar processing. When the imaging process according to the present example is started, the processing of the imaging process according to example 2 is performed in step S501 to step S1002. When the averaged tomographic image is displayed in the display unit 300 in step S1002, the process proceeds to step S1201.

In step S1201, the tomographic image generation unit 213 performs gradation conversion with respect to the N tomographic images stored in the storage unit 240. Specifically, the tomographic image generation unit 213 windows the pixel values in the tomographic image with the minimum value and the maximum value of the pixel values in the tomographic image as a window width, and performs linear gradation conversion to the pixel values included in the window width to convert the tomographic image into 8 bit data. The storage unit 240 stores the N tomographic images with the pixel values subjected to gradation conversion, instead of the N tomographic images before subjected to gradation conversion. Concerning the tomographic images after gradation conversion, in order to use expression 1 described above at the time of performing MAP estimation in step S508, the tomographic images after gradation conversion need to be returned to the gradation that is used at the time of generation of the tomographic images. Consequently, the storage unit 240 simultaneously stores conditions (the window width, gradation ratio, and the like) that are used when the pixel values are subjected to gradation conversion to 8 bit data with the tomographic image after gradation conversion. When the storage unit 240 stores the tomographic image after gradation conversion in step S1201, the process proceeds to step S1003.

When the tomographic image generation unit 213 determines that the post processing of the high-contrast mode is turned on in step S1003, the process proceeds to step S1004. When the region determination unit 214 determines the target region based on the averaged tomographic image in step S1004, as in the image process according to example 2, the process proceeds to step S1202.

In step S1202, the estimation unit 216 returns the gradations of the N tomographic images subjected to gradation conversion in accordance with the conditions at the time of gradation conversion that are stored. Thereafter, in step S508, the estimation unit 216 performs the MAP estimation processing according to example 2 using the N tomographic images the gradation of which is returned. The processing of step S508 and the following steps is the same as the imaging process according to example 1, and, therefore, an explanation thereof will be omitted.

As described above, when post processing is performed for the high-contrast mode, a plurality of tomographic images for use in MAP estimation need to be always stored. In this regard, in the present example, the storage unit 240 is configured to store a plurality of tomographic images subjected to gradation conversion to the information of 8 bit. By subjecting the data of the tomographic images that are stored to gradation conversion, a capacity of the data storage device, in which the images are stored is reduced, and a cost increase can be prevented.

Note that, in the present example, gradation conversion of the N tomographic images is performed after display of the averaged tomographic image, but timing for gradation conversion is not limited to this timing. For example, after the N tomographic images are generated, gradation conversion is performed in parallel with processing of averaging the averaged tomographic image of the N tomographic images, and the tomographic image after gradation conversion may be stored. In this case, after the averaged tomographic image is generated, the storage unit 240 erases data of the N tomographic images that are used in generation of the averaged tomographic image and are not subjected to gradation conversion.

Further, in the present example, the tomographic images with the pixel values concerning all the pixels of the N tomographic images being subjected to gradation conversion are stored, but the data after gradation conversion which is stored is not limited to this arrangement. The data after gradation conversion is stored to be used in MAP estimation processing, so that only the data of the target region for which the MAP estimation processing is performed may be stored. In this case, prior to the gradation conversion processing in step S1201, the target region setting processing in step S1004 is performed. Thereafter, the pixel values of the target region are subjected to gradation conversion to 8 bit data by gradation conversion processing, and are stored in the storage unit 240.

Further, when gradation conversion is performed for only the pixel values of the target region in which the signal intensity is low, the window width of windowing may be determined in accordance with the determination method of the target region. For example, the threshold value at the time of determining the target region may be set as a maximum value, and the maximum value and a minimum value of the pixel values of the pixels in the tomographic image may be set as the window width. Further, a histogram of the pixel values of the tomographic image is created, and a maximum value and a minimum value of lower 10% of the pixel values may be determined as the window width. In this case, the range of the pixel values at the time of determining the window width may be set at an arbitrary number such as lower 20%, 30%, or the like, in accordance with a desired configuration. In this case, at the time of gradation conversion, the gradation in the region in which the signal intensity is low can be made rich, and the image capacity that is stored can be further suppressed because the region of the data that is stored is limited. Further, at the time of gradation conversion, gradation conversion by gamma correction that makes gradation rich in the region in which the signal intensity is low may be performed instead of linear conversion.

Modification of Examples 1 to 3

Figure 13:
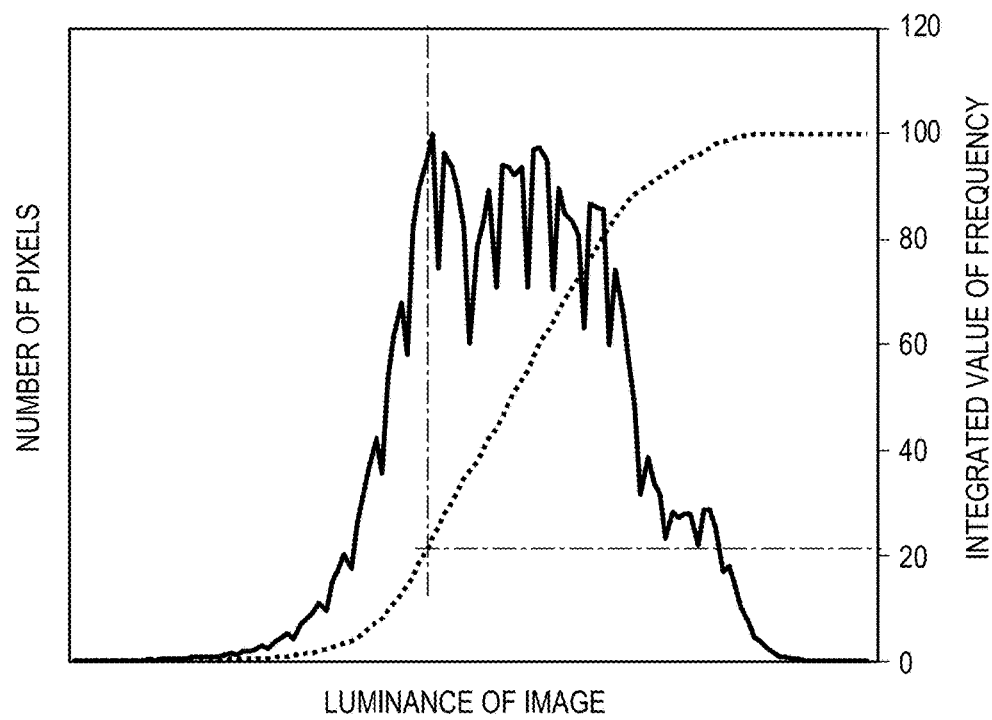
FIG. 13 is a diagram for describing region determination processing according to a modified example of examples 1 to 3.

In examples 1 to 3 described above, the region determination unit 214 determines the target region to which MAP estimation processing is performed, based on the threshold values obtained by segmentation processing and the histogram. In this regard, the region determination unit 214 may determine the target region based on a shape of the histogram of the pixel values of the tomographic image. FIG. 13 illustrates an example of the histogram of the pixel values of the tomographic image. In FIG. 13, a horizontal axis represents a luminance value that is a pixel value, and a vertical axis concerning a graph of a solid line represents the number of pixels having the luminance value, and a vertical axis concerning a graph of a dotted line represents an integrated value of a frequency.

When the region determination unit 214 determines the target region based on the shape of the histogram, a luminance value of percentile corresponding to an integrated value of frequency to a luminance value at which a first peak appears when the histogram is seen from a low luminance value can be set as the threshold value, in the histogram, for example. In the example illustrated in FIG. 13, the integrated value of frequency corresponding to the first peak illustrated by an alternate long and short dash line is approximately 21%, so that 21 percentile of the luminance values of the pixels of the averaged tomographic image is set as the threshold value, and a region of the pixels the luminance values of which are equal to or less than the threshold value is determined as a target region. Another arbitrary setting method of the threshold value based on the shape of the histogram for determining the region with a low signal intensity may be applied.

In the present modified example, the region in which the signal intensity is low can be also determined as the target region. Consequently, the MAP estimation processing is performed to only the region in which the signal intensity is low, the MAP estimation processing requiring a large amount of calculation is efficiently applied, and the tomographic image with greater contrast than the averaged image can be generated in a short time.

In examples 1 to 3, in the region in which the signal intensity is low, the signal intensity after addition average becomes greater than the true signal intensity, so that the configuration in which MAP estimation processing is applied to the region is adopted. In the region in which the signal intensity is low, however, the processing by which the signal intensity becomes greater than the true signal intensity is not limited to addition average. For example, the similar problems can occur in median value calculation processing, mode value calculation processing, maximum value calculation processing, and the like. Consequently, the disclosure can be also applied to an image processing method that reduces noise by performing the processing like this to a plurality of tomographic images.

Embodiment 2

In the MAP estimation processing described in the Chan et al. publication, the distribution of the signal intensity of OCT acquired with respect to the true signal intensity is assumed from the signal characteristics and noise characteristics, and the true signal intensity at which the occurrence probability of signals based on the distribution of the result of acquiring a large number of signals becomes maximum is estimated. Consequently, when the result of incorrect measurement is included in the signal acquisition result, due to the external factors, such as the intensity of the reflection signal from an eye changing because the eye moves during measurement, or a noise amount changing due to disturbance, it leads to fluctuation of the estimation result.

Here, an influence is very small when the signal intensity that is measured is large, with respect to the change of the signal intensity that occurs due to the external factor. When the signal intensity that is measured is small, however, a very small change of the signal intensity due to the external factor may cause large fluctuation of the estimation result. As a result, when the tomographic image of a fundus is imaged, for example, roughness sometimes becomes conspicuous on the image, particularly in a vitreous body, a sclera and a choroid membrane that are regions in which the signal intensities are low.

Therefore, embodiment 2 of the disclosure provides an optical coherence tomography apparatus that can generate an image having greater contrast and lower noise as compared with the average processing of the image that is conventionally used.

Before describing an example of the present embodiment, an outline of the present embodiment will be described. In the present embodiment, in the light of the problem described above that first occurs in the high-contrast tomographic image that is obtained by performing MAP estimation processing, processing of making roughness inconspicuous is performed. More specifically, a tomographic image with high contrast and less roughness is provided by generating a high-contrast image by performing MAP estimation processing on tomographic signals of OCT, and applying the processing of making roughness inconspicuous to the high-contrast image thereafter.

Example 4

Hereafter, with reference to FIGS. 14 to 18D, an optical coherence tomography apparatus (an OCT apparatus) according to example 4 of the present embodiment will be described. The OCT apparatus according to the present example has a similar configuration to the configuration of the OCT apparatus according to example 1 except for a control unit 1400, so that the same reference signs will be used for the components, and an explanation thereof will be omitted. Hereafter, concerning the OCT apparatus according to the present example, a difference from the OCT apparatus according to example 1 will be mainly described.

Configuration of Control Unit 1400

Figure 14:
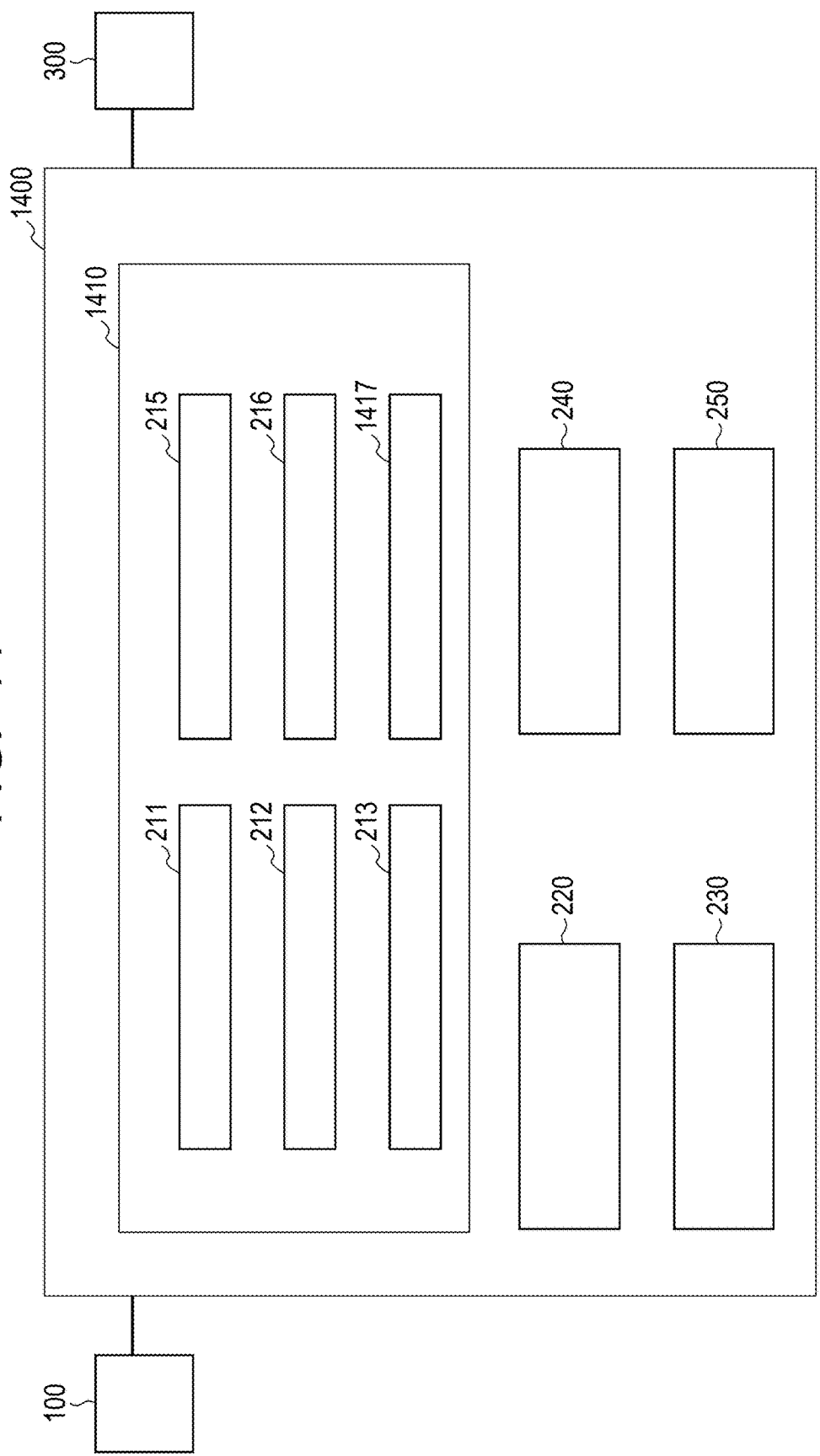
FIG. 14 illustrates a schematic configuration of a control unit according to example 4.

With reference to FIG. 14, a configuration of the control unit 1400 will be described. FIG. 14 is a block diagram illustrating a schematic configuration of the control unit 1400.

In the control unit 1400, an image generation unit 1410, the acquiring unit 220, the drive control unit 230, the storage unit 240 and the display control unit 250 are provided. The acquiring unit 220, the drive control unit 230, the storage unit 240 and the display control unit 250, which are provided in the control unit 1400, are the same as the respective components in example 1, and, therefore, an explanation thereof will be omitted.

In the image generation unit 1410, the anterior eye image generation unit 211, the fundus image generation unit 212, the tomographic image generation unit 213, the calculation unit 215, the estimation unit 216, and a filter unit 1417 are provided. The anterior eye image generation unit 211, the fundus image generation unit 212, the tomographic image generation unit 213, the calculation unit 215, and the estimation unit 216 that are provided in the image generation unit 1410 are the same as the respective components in example 1, and, therefore, an explanation thereof will be omitted.

The filter unit 1417 applies a noise removal filter to a high-contrast tomographic image based on the estimation value estimated by the estimation unit 216, and reduces noise in the high-contrast tomographic image. Here, the noise removal filter can be a filter that is used to reduce noise in the image. As the noise removal filter, a known filter, such as an expansion/contraction filter, a moving-average filter, a Gaussian filter, a weighting filter, a bilateral filter, and a median filter can be used, for example. In the present example, a moving-average filter is used. A filter size, a weighting direction, and the like, that are filter parameters of the noise removal filter may be set arbitrarily in accordance with a desired configuration.

The filter unit 1417 can be also configured by a module executed by a CPU and an MPU of the control unit 1400. Further, the filter unit 1417 may be configured by a circuit, or the like, that realizes a specific function such as ASIC.

Imaging Process of Tomographic Image

Figure 15:
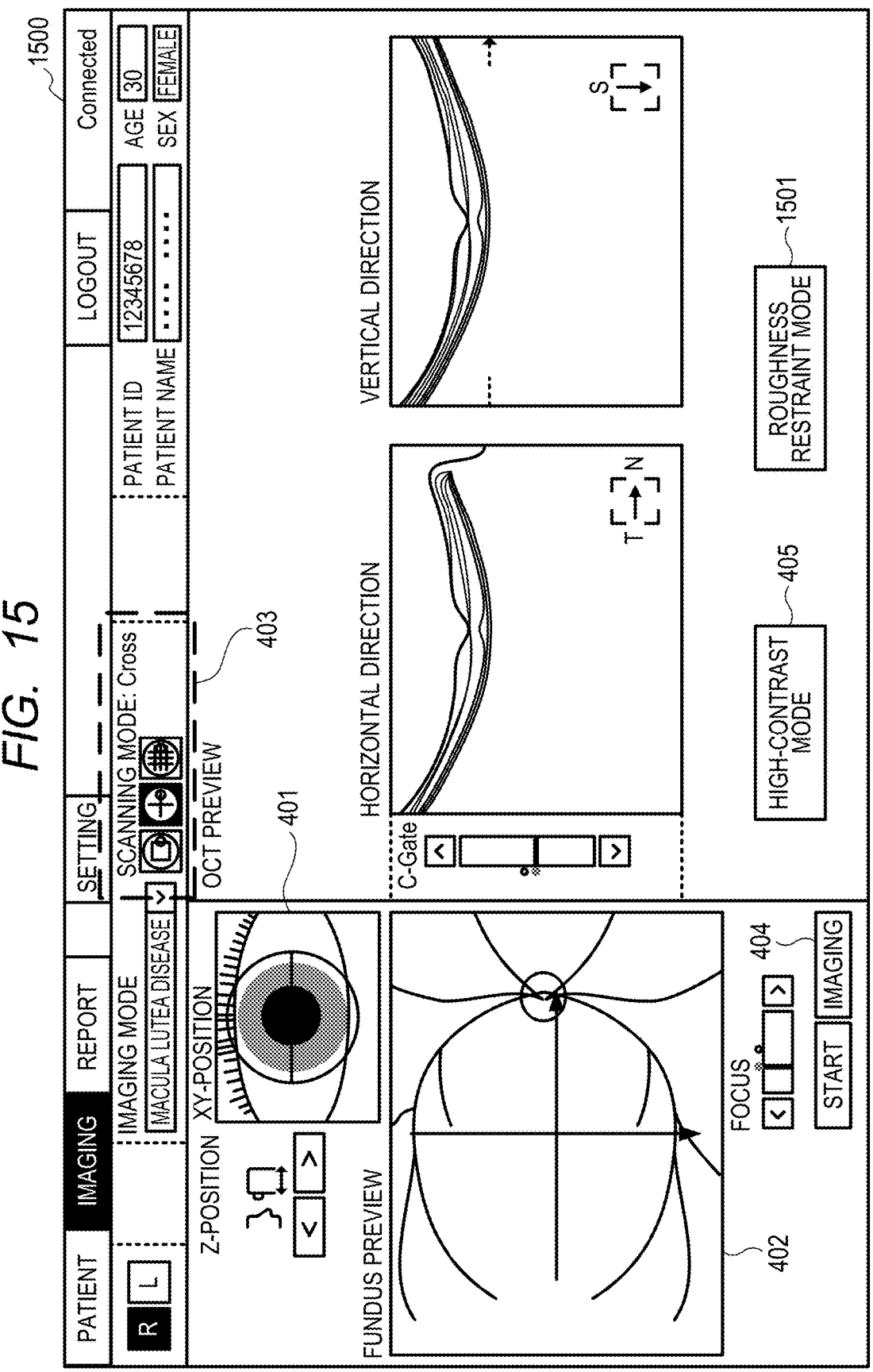
FIG. 15 illustrates an example of a display screen of a display unit according to example 4.

Hereafter, with reference to FIGS. 15 to 18D, an imaging process of a tomographic image according to the present example will be described. FIG. 15 illustrates an example of a preview screen 1500 of a GUI for control/image display according to the present example displayed in the display unit 300. A report screen of the GUI for control/image display that is displayed in the display unit 300 is similar to the report screen 406 according to example 1, and, therefore, an explanation thereof will be omitted.

The preview screen 1500 illustrated in FIG. 15 is a screen that is displayed to perform instruction to start imaging, alignment adjustment of the imaging optical system 100, adjustment of a position of a site to be imaged, and the like. In the present example, a function of generating a high-contrast tomographic image can be used by pressing the high-contrast mode button 405 on the preview screen 1500 illustrated in FIG. 15 using input equipment, which is not illustrated, and turning on the high-contrast mode. Similarly, by pressing a roughness restraint mode button 1501, and turning on a roughness restraint mode, a function of generating a tomographic image with high contrast and low noise can be used.

In the present example, after imaging preparation is made in the preview screen 1500 illustrated in FIG. 15, the fundus Er of a subject is imaged with use of the OCT apparatus 1. The procedures of imaging preparation and start of imaging are similar to the procedures thereof according to example 1, and, therefore, an explanation thereof will be omitted.

Figure 16:
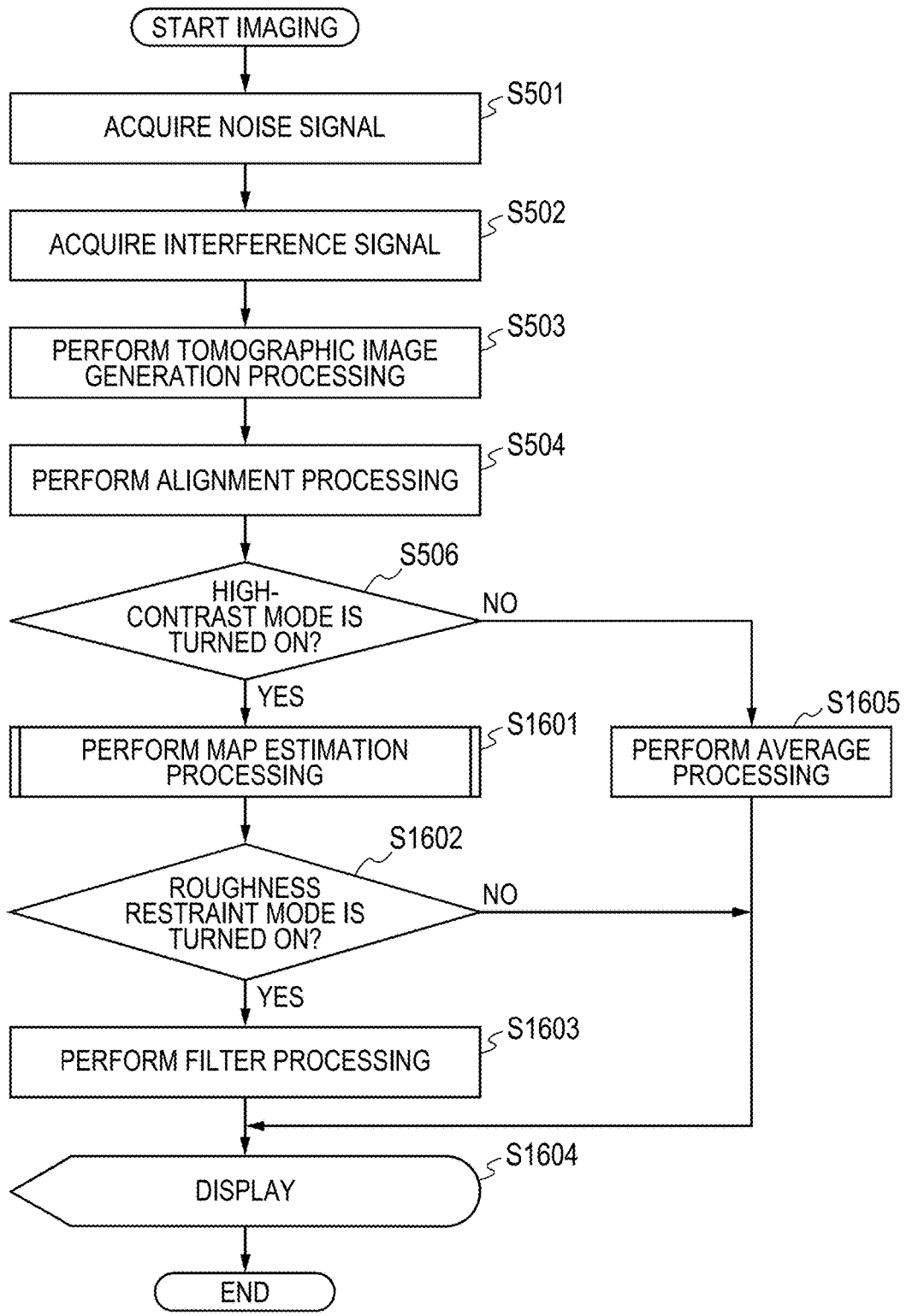
FIG. 16 illustrates a flowchart of a tomographic image imaging process according to example 4.

FIG. 16 illustrates a flowchart of the imaging process of the tomographic image according to the present example. Processing of noise signal acquisition to alignment, and determination of ON/OFF of the high-contrast mode according to the present example are similar to the same processing according to example 1, and, therefore, an explanation thereof will be omitted with use of the same reference signs.

When alignment of the tomographic image is ended in step S504, the process proceeds to step S506. In step S506, the tomographic image generation unit 213 determines whether or not the high-contrast mode is turned on. When the tomographic image generation unit 213 determines that the high-contrast mode is not turned on in step S506, the process proceeds to step S1605.

In step S1605, the calculation unit 215 calculates the calculation values of N pixel values for each pixel, with respect to N tomographic images that are aligned, and the tomographic image generation unit 213 generates a tomographic image averaged (an averaged tomographic image) using the calculated calculation values as representative values of the respective pixels. The storage unit 240 stores the generated averaged tomographic image. In the present example, the calculation unit 215 calculates the calculation values by adding and averaging luminance values of the pixel positions in the N tomographic images, corresponding to the respective pixel positions of the averaged tomographic image which is generated. Subsequently, the tomographic image generation unit 213 generates the averaged tomographic image using the calculation values that are calculated as the luminance values in the respective pixel positions. As described above, the calculation value is not limited to what is obtained by addition average (arithmetic mean value), but may be a median value, a mode value, a maximum value, or the like.

Thereafter, in step S1604, the display control unit 250 causes the display unit 300 to display the averaged tomographic image stored in the storage unit 240 in step S1605 to end the imaging process.

When the tomographic image generation unit 213 determines that the high-contrast mode is turned on in step S506, the process proceeds to step S1601.

Figure 17:
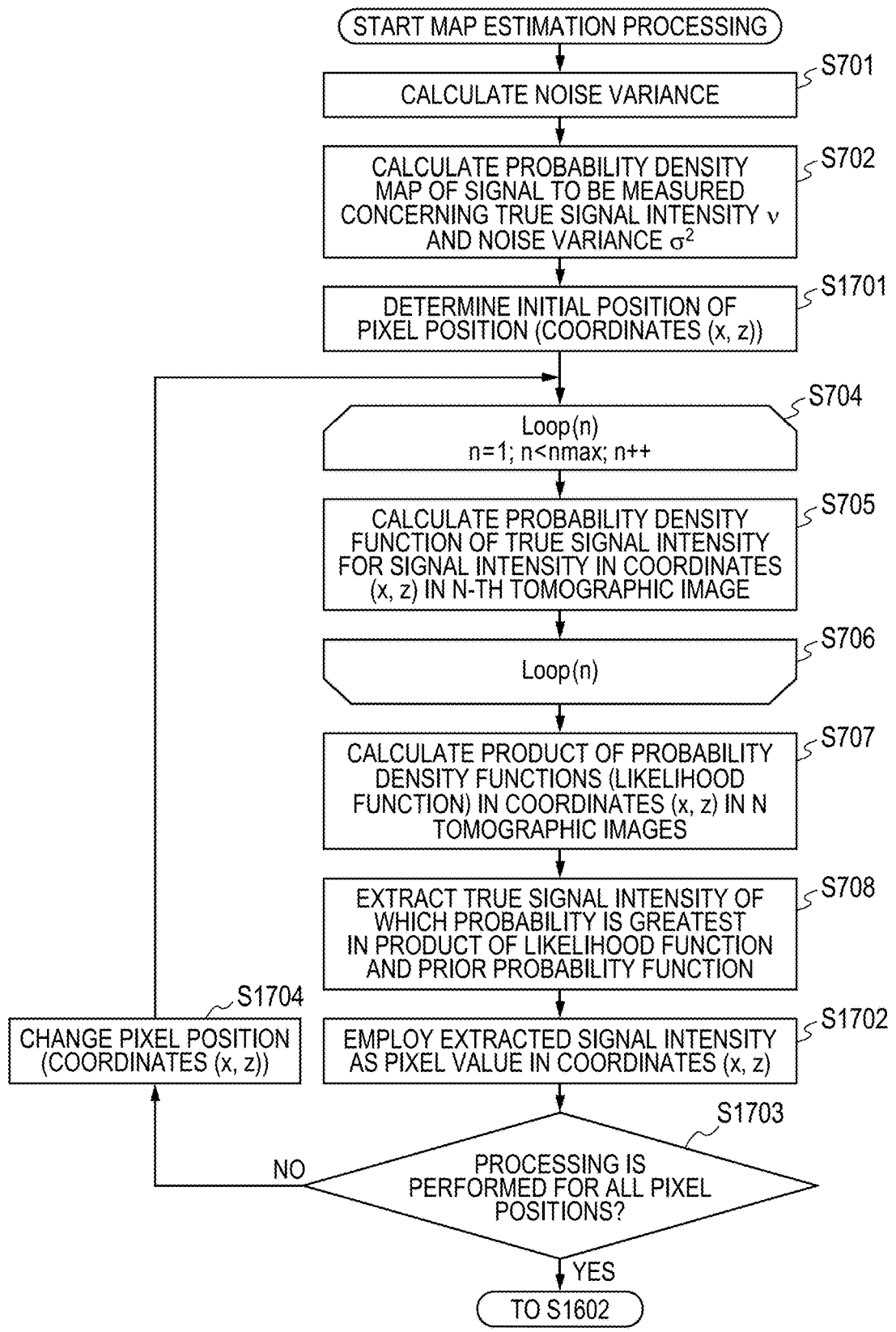
FIG. 17 illustrates a flowchart of MAP estimation processing according to example 4.

In step S1601, the estimation unit 216 performs MAP estimation processing with respect to the N tomographic images that are aligned, estimates estimation values in the respective pixel positions, and the tomographic image generation unit 213 generates a high-contrast tomographic image using the estimation values that are estimated. Hereafter, MAP estimation processing according to the present example will be described with reference to FIG. 17. FIG. 17 illustrates a flowchart of the MAP estimation processing according to the present example. In the MAP estimation processing according to the present example, calculation of noise variance, a probability density map, a probability density function and a product of the probability density functions, and processing relating to extraction of a true signal intensity are similar to those in the MAP estimation processing according to example 1, and, therefore, an explanation thereof will be omitted with use of the same reference signs.

When the probability density map is calculated in step S702, the process proceeds to step S1701. In step S1701, the estimation unit 216 sets an initial position of a pixel position (coordinates (x, z)) at the time of starting the MAP estimation processing. Here, the coordinates (x, z) represent coordinates in a tomographic image with high contrast (high-contrast tomographic image) to be generated, x represents a position in the B scan direction in the tomographic image, and z represents a position in a depth direction in the tomographic image. The respective coordinates in the high-contrast tomographic image to be generated correspond to respective coordinates in the averaged tomographic image and the N tomographic images that are aligned. In the present example, the initial value of the pixel position is set at coordinates (1, 1). Note that the initial value is not limited to this, but may be coordinates of an arbitrary pixel position in the tomographic image.

Next, in step S704 to step S706, the estimation unit 216 determines a parameter (true signal intensity v) at which the probability becomes maximum in the posterior probability function, as in the MAP estimation processing according to example 1. When the true signal intensity v is determined, the process proceeds to step S1702.

In step S1702, the tomographic image generation unit 213 determines the estimation value (the determined true signal intensity v) estimated by the MAP estimation processing by the estimation unit 216 in the pixel position corresponding to the coordinates (x, z) as the representative value, and adopts the estimation value as the pixel value.

Thereafter, in step S1703, the estimation unit 216 determines whether or not the estimation unit 216 estimates the estimation values with respect to all the pixel positions. When the estimation unit 216 determines that the estimation unit 216 does not estimate the estimation values with respect to all the pixel positions, the process proceeds to step S1704. In step S1704, the estimation unit 216 moves the pixel position (coordinates (x, z)) for which the estimation unit 216 estimates the estimation value, and, thereafter, returns the process to step S704.

When the tomographic image generation unit 213 determines that the tomographic image generation unit 213 determines the pixel values based on the estimation values with respect to all the pixel positions in step S1703, the process proceeds to step S1602. The tomographic image generation unit 213 can generate a high-contrast tomographic image having the pixel values based on the estimation values by the MAP estimation processing by determining the pixel values based on the estimation values with respect to all the pixel positions. The storage unit 240 stores the generated high-contrast tomographic image.

In step S1602, the tomographic image generation unit 213 determines whether or not the roughness restraint mode is turned on. When the tomographic image generation unit 213 determines that the roughness restraint mode is not turned on in step S1602, the process proceeds to step S1604. In step S1604, the display control unit 250 causes the display unit 300 to display the high-contrast tomographic image stored in the storage unit 240, and ends the imaging process.

When the tomographic image generation unit 213 determines that the roughness restraint mode is turned on in step S1602, the process proceeds to step S1603.

In step S1603, the filter unit 1417 applies the moving-average filter that is a noise removal filter to the high-contrast tomographic image stored in the storage unit 240, and reduces noise in the high-contrast tomographic image.

Figure 18A:
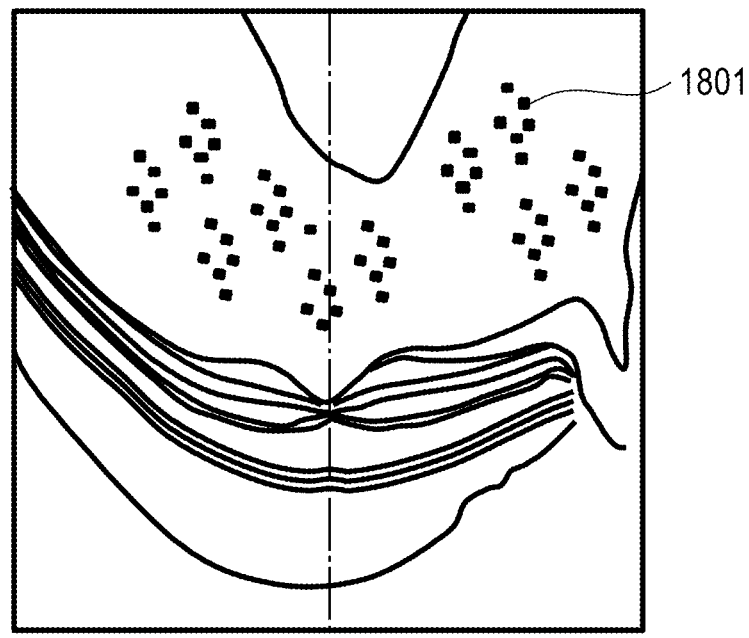
FIG. 18A is a view for describing noise reduction according to example 4.

FIG. 18A illustrates an example of the high-contrast tomographic image that which is generated by the aforementioned MAP estimation processing. Further, FIG. 18C illustrates a profile of one line of the high-contrast tomographic image, which corresponds to an alternate long and short dash line in FIG. 18A. In the high-contrast tomographic image illustrated in FIG. 18A, it is found that noise 1801 in which contrast appears strongly occurs to the region of a vitreous body. In particular, when the profile of one line of the high-contrast tomographic image corresponding to an A scan image is seen, noise occurs with strong contrast, as illustrated in FIG. 18C.

In order to restrain the noise, the filter unit 1417 performs filter processing using a moving-average filter of 3×3 pixels to the high-contrast tomographic image. Specifically, the filter unit 1417 carries out filter processing by convoluting the high-contrast tomographic image and the moving-average filter of 3×3. A tomographic image in which noise in the high-contrast tomographic image is reduced can be generated by the processing.

Figure 18B:
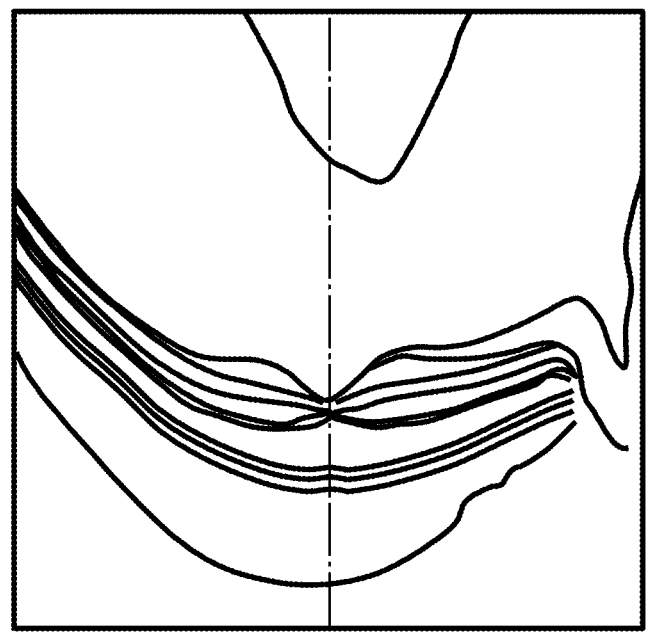
FIG. 18B is a view for describing noise reduction according to example 4.
Figure 18C:
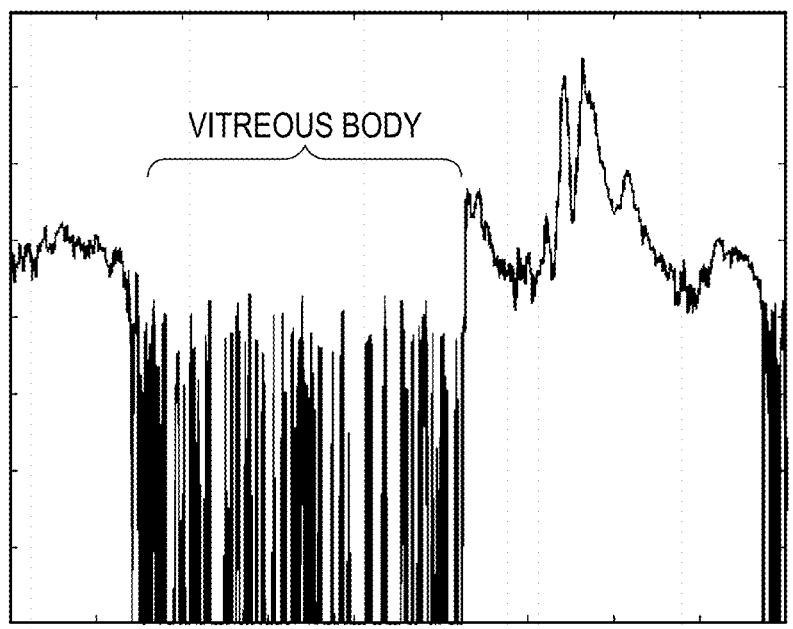
FIG. 18C is a view for describing noise reduction according to example 4.
Figure 18D:
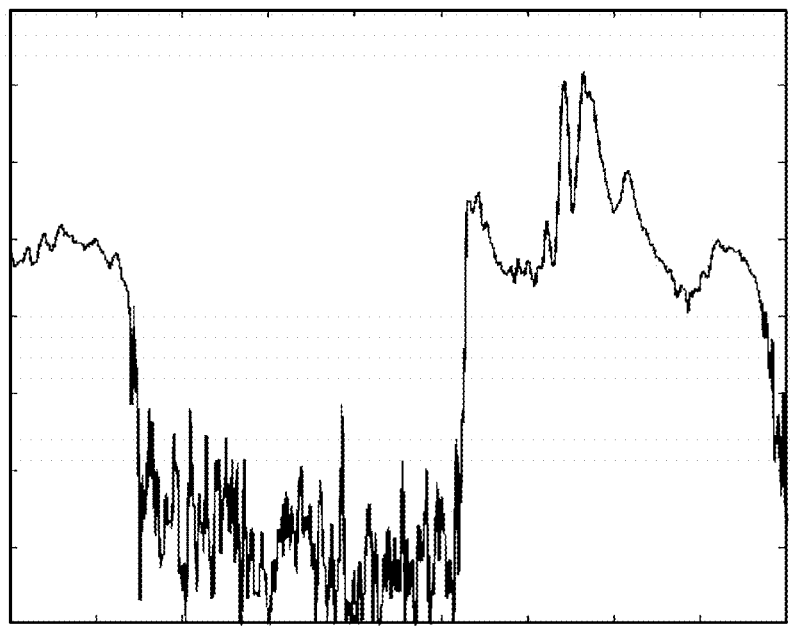
FIG. 18D is a view for describing noise reduction according to example 4.

FIG. 18B illustrates an example of a tomographic image with high contrast and low noise that is generated. Further, FIG. 18D illustrates a profile of one line of the high-contrast tomographic image, corresponding to an alternate long and short dash line in FIG. 18B. In FIG. 18B, the noise 1801 that occurs in the high-contrast tomographic image illustrated in FIG. 18A is reduced. In particular, when the profile of the one line of the high-contrast tomographic image corresponding to the A scan image is seen, it is found that noise is reduced as illustrated in FIG. 18D.

When the filter unit 1417 generates a tomographic image with high contrast and low noise, the storage unit 240 stores the tomographic image with high contrast and low noise that is generated, and the process proceeds to step S1604.

In step S1604, the display control unit 250 causes the display unit 300 to display the tomographic image with high contrast and low noise that which is stored in the storage unit 240, and ends the imaging process.

In this way, the control unit 1400 applies the noise removal filter to the high-contrast tomographic image that is generated by performing the MAP estimation processing. Thereby, the control unit 1400 can generate the tomographic image with high contrast and low noise.

As described above, the image generation unit 1410 of the control unit 1400 according to the present example includes the filter unit 1417 that applies the noise removal filter to the high-contrast tomographic image that is generated using the estimated estimation values as the representative values. The control unit 1400 according to the present example applies the noise removal filter to the high-contrast tomographic image that is generated based on the estimation values obtained by the MAP estimation processing. Thereby, the tomographic image with greater contrast and lower noise than the averaged tomographic image can be generated.

In the present example, the luminance values of the tomographic image are used as the signal intensities in the addition average processing and MAP estimation processing, but the signal intensities for use in these kinds of processing are not limited to the luminance values. The signals for use in these kinds of processing can be signals corresponding to the respective pixel positions, and, therefore, can be tomographic signals based on signals after the interference signals acquired in the OCT optical system are subjected to Fourier conversion. The tomographic signals include, for example, signals after the interference signals being subjected to Fourier conversion, signals obtained by applying arbitrary signal processing for image generation to the signals after the Fourier conversion, and signals of luminance values, and the like, based on these signals.

In the present example, an example of imaging the fundus Er is shown, but the imaging target portion is not limited to the fundus Er, and may be an anterior eye portion.

Example 5

While filter processing is performed to all the pixels of the high-contrast tomographic image in example 4, filter processing is performed to only a specific region in the present example. In the filter processing of example 4, the noise removal filter is also applied to a retina. In general, the noise removal filter, such as a moving-average filter, tends to reduce spatial resolution. Consequently, a high resolution tomographic image for use in the purpose of observing a subject in detail sometimes cannot be generated.

Meanwhile, the region in which the signal intensity is low and roughness occurs at the time of fundus observation is broadly divided into three kinds of regions that are a vitreous body region, a choroid membrane region, and a sclera region. It is known that a very small structure does not exist anatomically, particularly in the regions of the vitreous body and sclera out of these regions, so that, even if reduction in the above described spatial resolution occurs, detailed observation can be performed. Consequently, detailed observation can be performed even if the noise removal filter is applied to these regions.

Thus, in the present example, at the time of generating a high-contrast tomographic image, filter processing is applied to only these regions in which noise easily occurs and the signal intensities are low. More specifically, a fundus tomographic image in the tomographic image is separated into anatomical layers, and the noise removal filter is applied to only the regions that are known as the regions in which the signal intensities are low. Thereby, a high-contrast tomographic image from which roughness (noise) in the regions in which the signal intensities are low is reduced can be obtained.

Figure 20:
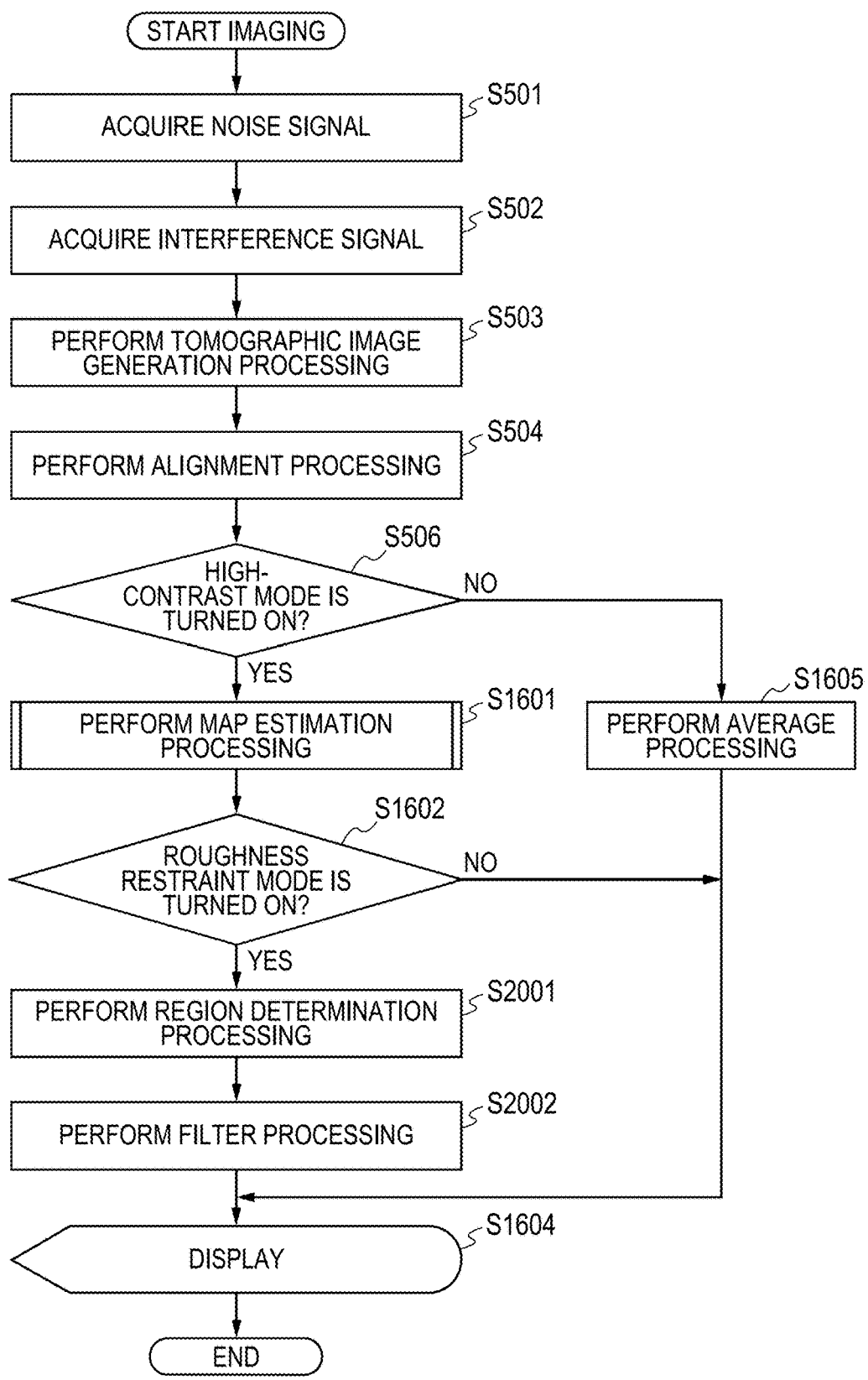
FIG. 20 illustrates a flowchart of a tomographic image imaging process according to example 5.
Figure 21:
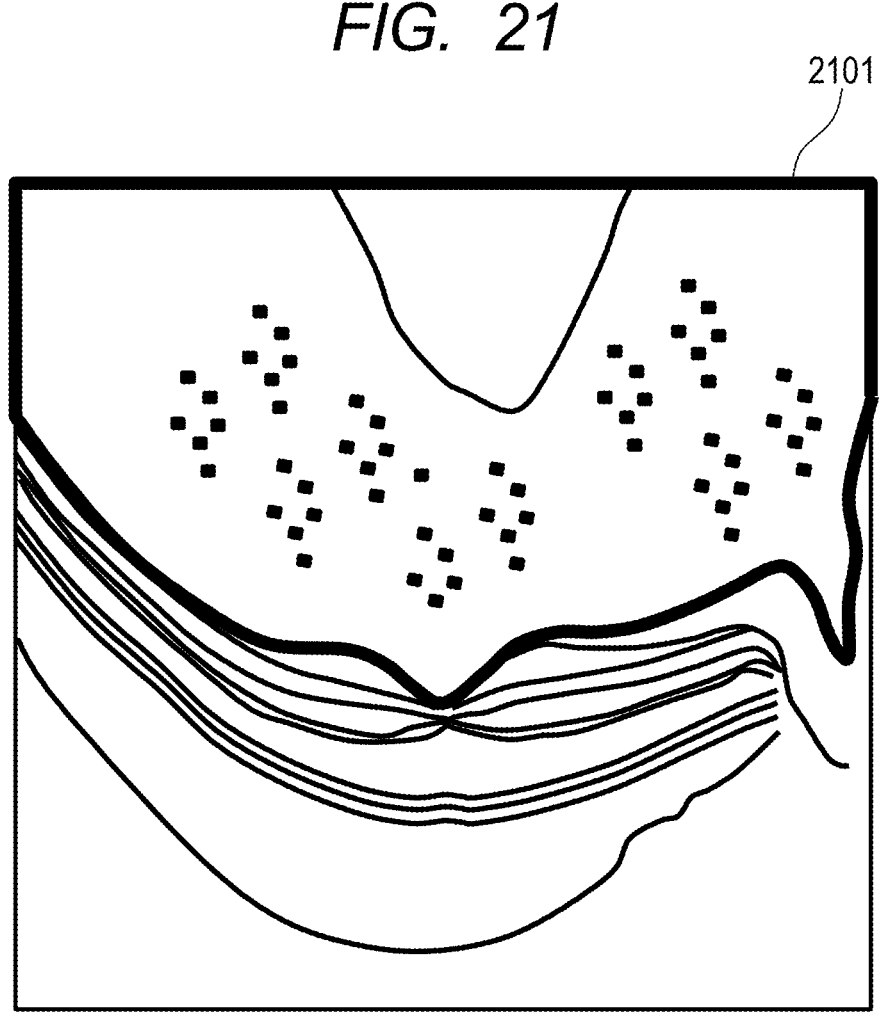
FIG. 21 is a view for describing region determination processing according to example 5.

Hereafter, with reference to FIGS. 19 to 21, an OCT apparatus according to example 5 will be described. In the OCT apparatus according to the present example, the noise removal filter processing is applied to only the vitreous body that is the region in which the signal intensity obtained when the tomographic signal of the fundus is acquired is low, and noise of the high-contrast tomographic image is reduced. Concerning components of the OCT apparatus according to the present example, for the components similar to those in the OCT apparatus according to example 4, the same reference signs will be used and explanation thereof will be omitted. Hereafter, concerning the OCT apparatus according to the present example, a difference from the OCT apparatus according to example 4 will be mainly described.

FIG. 19 illustrates a schematic configuration of a control unit 1900 (an image processing apparatus) according to the present example. In an image generation unit 1910 of the control unit 1900, a region determination unit 1918 is provided in addition to the anterior eye image generation unit 211 to the filter unit 1417.

The region determination unit 1918 determines a target region with a low signal intensity, to which the noise removal filter should be applied, based on the tomographic image generated by the tomographic image generation unit 213. The region determination unit 1918 may determine the target region based on the signals after Fourier conversion, or the like, that are acquired by the acquiring unit 220.

Next, an imaging process according to the present example will be described with reference to FIG. 20. FIG. 20 illustrates a flowchart of the imaging process of a tomographic image according to the present example. The imaging process according to the present example is similar to the imaging process according to example 4, except for the point that the target region to which the filter is applied is determined and the filter is applied to only the determined target region, and, therefore, an explanation thereof will be omitted except for the point.

When the tomographic image generation unit 213 determines that the roughness restraint mode is turned on in step S1602, the process proceeds to step S2001.

In step S2001, the region determination unit 1918 performs segmentation processing on the high-contrast tomographic image that is generated based on the estimation values, and determines the vitreous body region that is the region in which the signal intensity is low as the target region. Specific processing is similar to the processing by the region determination unit 214 according to example 1, and, therefore, an explanation thereof will be omitted.

In the present example, the region determination unit 1918 extracts an internal limiting membrane (ILM) by segmentation processing. The region determination unit 1918 determines that an opposite side (a pupil side) to a retina, of an ILM boundary is a vitreous body, and determines a region at the pupil side from the ILM boundary (a region 2101 illustrated in FIG. 21) as the vitreous body region that is known as the region in which the signal intensity is low. Thereby, the region determination unit 1918 determines the vitreous body region as the target region to which the noise removal filter is applied.

The region determination unit 1918 may perform segmentation processing on at least one of N tomographic images that are aligned, determine the region in which the signal intensity is low, and determine the region as the target region. Further, the segmentation processing may be performed using an arbitrary known method other than the above described method. Further, in the present example, the vitreous body region is determined as the target region, but an arbitrary region, such as a sclera region that is known, as the region in which the signal intensity is low may be determined as the target region, for example. In this case, the region determination unit 1918 determines a layer of a sclera, or the like, by segmentation processing, and can determine the layer as the target region. Further, the target region is not limited to one of these regions, but may be both the vitreous body region and the sclera region, for example.

When the target region is determined, the filter unit 1417 applies the noise removal filter to the target region in step S2002. More specifically, the filter unit 1417 performs convolution to only the target region of the high-contrast tomographic image that is generated based on the estimation values using a Gaussian filter of 5×5 pixels and (3=0.5, and carries out filter processing. Thereby, the tomographic image with high contrast and low noise to which the noise removal filter is applied to only the target region in which the signal intensity is low can be generated. The storage unit 240 stores the generated tomographic image. Thereafter, in step S1604, the display control unit 250 displays the generated tomographic image with high contrast and low noise on the display unit 300. The noise removal filter that is applied is not limited to the Gaussian filter, but may be the aforementioned arbitrary filters, such as a moving-average filter and a weighting filter. Further, filter parameters of the noise removal filter, such as the filter size, may be arbitrarily set.

As described above, the image generation unit 1910 according to the present example includes the region determination unit 1918 that determines the target region in a tomographic image using the information on a plurality of tomographic images. More specifically, the region determination unit 1918 determines the anatomical layer (layer boundary) of a fundus based on the high-contrast tomographic image that is generated using the estimation values as the representative values. Thereafter, the region determination unit 1918 determines the target region from the determined layer and the eye structure. The filter unit 1417 applies the noise removal filter to only the target region that is determined by the region determination unit 1918.

Thereby, in the OCT apparatus according to the present example, a fundus tomographic image with high contrast and noise in the target region being restrained can be obtained without involving reduction in a spatial resolution of the retina structure. Further, since the regions of the vitreous body and the sclera in which the signal intensities are low are the regions that do not have very small structures, so that, even if the noise removal filter is applied, observation can be performed in detail.

In the present example, the region determination unit 1918 determines the anatomical layer of the fundus based on the high-contrast tomographic image that is generated using the estimation values as the representative values. The region determination unit 1918 may, however, determine the anatomical layer of a fundus based on the information on at least one tomographic image of the information on a plurality of tomographic images.

In the present example, the configuration is described, in which the region corresponding to the layer structure that is set in advance as the region in which the signal intensity is low is determined as the target region to which the noise removal filter is applied. Setting of the layer structure and tissue corresponding to the region that is determined as the target region is not limited, however, to this setting, and the layer structure and the tissue may be arbitrarily set in accordance with a desired configuration. For example, the layer structure and the tissue may be set by an examiner using a GUI, or may be set by a recommendation mode corresponding to a specific disease being selected.

Modified Example of Example 5

At the time of fundus observation, in the region, such as a retina in which the signal intensity is sufficiently high, no difference occurs to the results of the average processing and MAP estimation processing. Consequently, average processing may be performed to the retina region without performing MAP estimation processing, and MAP estimation processing and filter processing of the noise removal filter may be performed to only the target region in which the signal intensity is low. Thereby, the amount of calculation is restrained by limiting the region to which MAP estimation processing is performed, the calculation time is shortened, and roughness in the high-contrast tomographic image can be reduced.

Here, a modified example of example 5 will be described with reference to FIG. 22. In example 5, only the region in which the signal intensity is low is determined and filter processing is performed, but concerning MAP estimation processing, the processing is applied to the entire image. In the present modified example, MAP estimation processing is also carried out to the same region as the region to which filter processing is performed.

Figure 22:
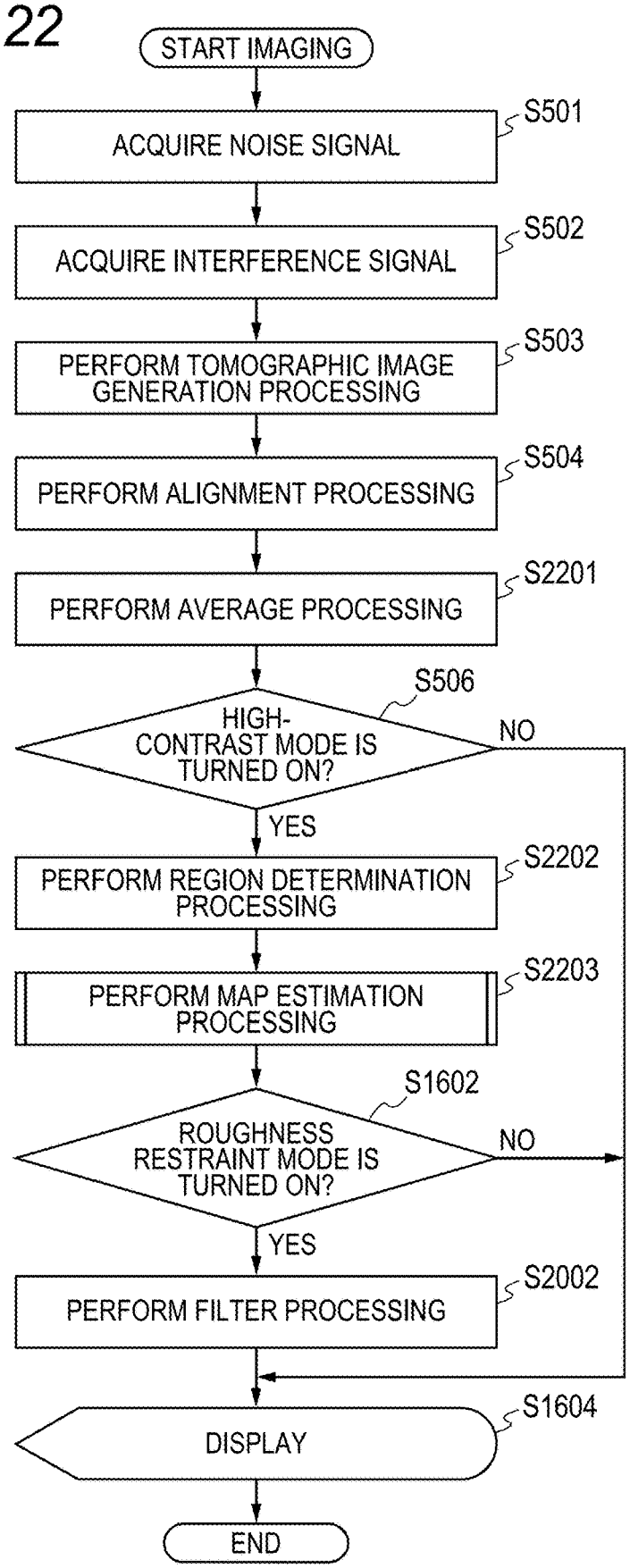
FIG. 22 illustrates a flowchart of a tomographic image imaging process according to a modified example of example 5.

FIG. 22 illustrates a flowchart of an imaging process of a tomographic image according to the modified example of example 5. Hereafter, the same processing as in the tomographic imaging process according to example 5 will be omitted, and a difference will be mainly described.

In the present modified example, after alignment processing is performed in step S504, the process proceeds to step S2201. In step S2201, the calculation unit 215 calculates calculation values, and the tomographic image generation unit 213 generates an averaged tomographic image using the calculated calculation values as in step S1605 of the processing according to example 5. The storage unit 240 stores the averaged tomographic image that is generated.

Thereafter, the process proceeds to step S506. When the tomographic image generation unit 213 determines that the high-contrast mode is not turned on in step S506, the process proceeds to step S1604, and the display control unit 250 causes the display unit 300 to display the averaged tomographic image. When the tomographic image generation unit 213 determines that the high-contrast mode is turned on, the process proceeds to step S2202.

In step S2202, the region determination unit 1918 performs region determination processing as in step S2001 in example 5. Here, in the present example, the region determination unit 1918 performs region determination processing on the averaged tomographic image that is generated in step S2201, and determines a target region to which MAP estimation processing and filter processing are applied.

When the target region is determined, the estimation unit 216 performs MAP estimation processing with respect to all pixels in the target region, in step S2203. Here, the MAP estimation processing in the present example is similar to the MAP estimation processing illustrated in FIG. 17, but since the target to which the processing is performed is the pixels in the target region, the estimation unit 216 determines the pixel position in the target region as the initial position in step S1701. The initial position may be an arbitrary position if only it is the position in the target region. For example, the estimation unit 216 determines coordinates, in which the values of x and z are the smallest of the target region, as the initial position. Further, in step S1702, the tomographic image generation unit 213 overwrites the pixel value with the signal intensity extracted in step S708 as the representative value, in the pixel position of the averaged tomographic image corresponding to the coordinates (x, z). Subsequently, in step S1703, the estimation unit 216 determines whether or not the estimation unit 216 performs processing with respect to all the pixel positions in the target region, and, when there is an unprocessed pixel position, the estimation unit 216 moves the pixel position to the unprocessed pixel position in step S1704.

As described above, in the present modified example, the tomographic image generation unit 213 generates the tomographic image with the estimation values set as the representative values in the target region of the tomographic image, and with the calculation values set as the representative values in the regions other than the target region. Thereby, the MAP estimation processing is also performed to only the target region, so that the number of pixels to which the MAP estimation processing is performed decreases, and the calculation time can be shortened. The calculation value can be made any one of an arithmetic mean value, a median value, a mode value, and a maximum value, as described above.

Further, in the present modified example, the region determination unit 1918 determines the target region based on the averaged tomographic image, and the tomographic image generation unit 213 overwrites the pixel values with the estimation values by MAP estimation as the representative values for the target region, and generates a high-contrast tomographic image. The configuration in which a high-contrast tomographic image is generated is not, however, limited to this configuration. For example, the target region may be determined based on at least one tomographic image of the N tomographic images that are aligned. Further, as for the pixel values in the target region, only MAP estimation processing is performed without performing average processing, and the estimation values may be set as the representative values. The region determination unit 1918 may determine the target region to which MAP estimation is performed using the signal intensity of each pixel as in example 2.

Example 6

In the OCT apparatus according to example 5, the region determination unit 1918 determines the region to which filter processing is performed using the layer boundary extraction processing. In contrast with this, in an OCT apparatus according to example 6, a region in which the signal intensity is low after MAP estimation processing is extracted as a target region, and filter processing is performed to the extracted target region.

Hereafter, with reference to FIGS. 23A to 23D, the OCT apparatus according to the present example will be described. Concerning components of the OCT apparatus according to the present example for describing region determination processing according to the present example, the components of the OCT apparatus are similar to the components of the OCT apparatus according to example 5, so that an explanation thereof will be simplified using the same reference sign. Hereafter, concerning the OCT apparatus according to the present example, a difference from the OCT apparatus according to example 5 will be mainly described.

Figure 23A:
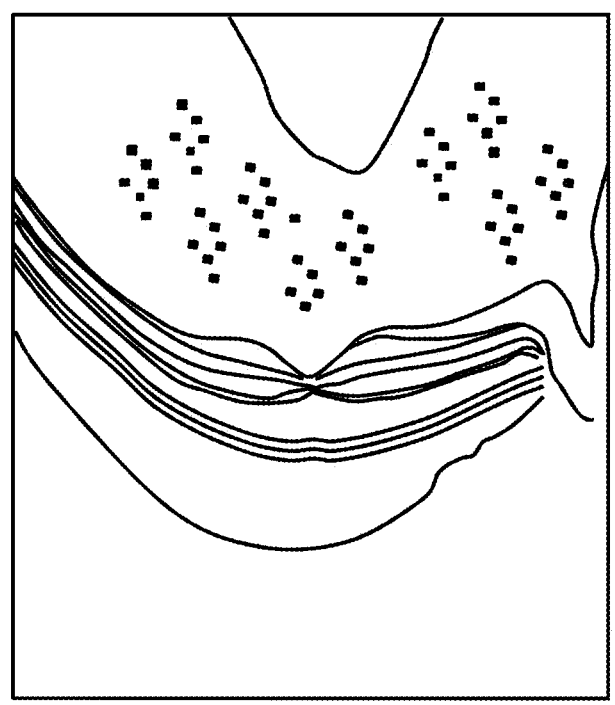
FIG. 23A is a view for describing region determination processing according to example 6.
Figure 23B:
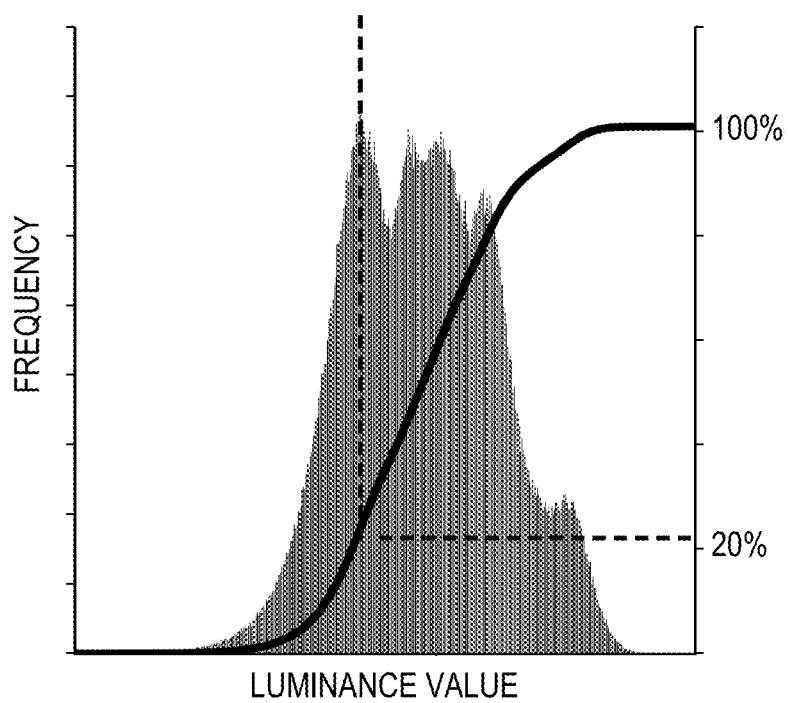
FIG. 23B is a view for describing the region determination processing according to example 6.
Figure 23C:
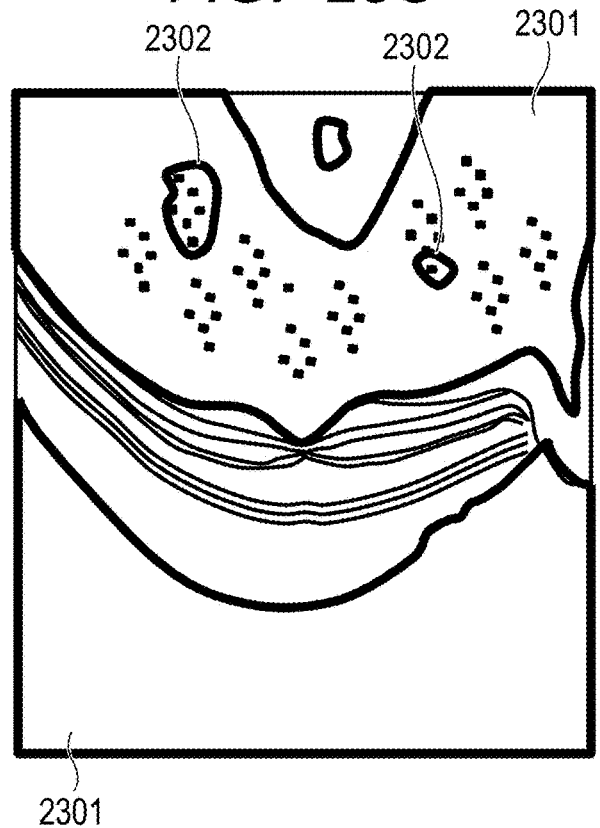
FIG. 23C is a view for describing the region determination processing according to example 6.
Figure 23D:
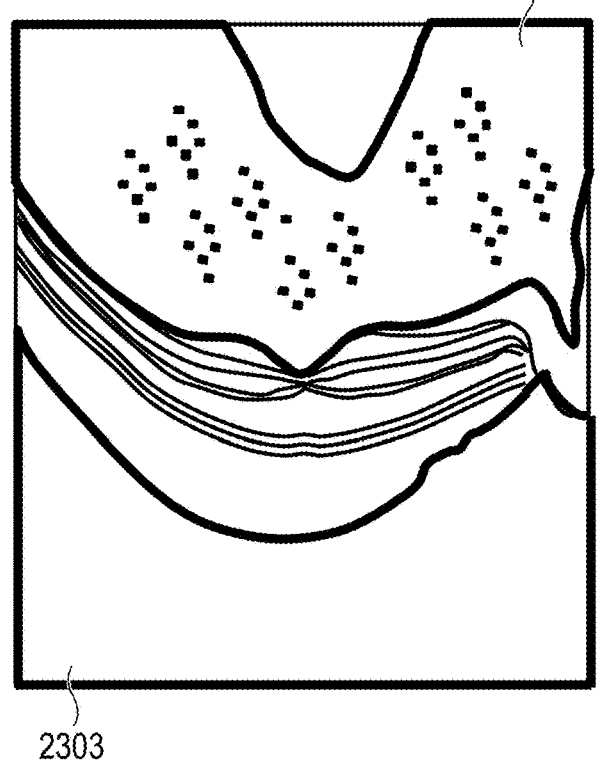
FIG. 23D is a view for describing the region determination processing according to example 6.

FIG. 23A illustrates an example of a high-contrast tomographic image generated by MAP estimation processing. FIG. 23B illustrates a histogram of the high-contrast tomographic image illustrated in FIG. 23A. FIGS. 23C and 23D illustrate examples of the target region determined by the region determination unit 1918. In FIG. 23B, a horizontal axis represents a luminance value, a vertical axis of the histogram represents the number (frequency) of pixels having luminance values, and a vertical axis concerning a graph of a solid line represents an integrated value of the frequency.

The region determination unit 1918 according to the present example creates the histogram (FIG. 23B) with respect to the high-contrast tomographic image that is generated based on estimation values illustrated in FIG. 23A in step S2001. Thereafter, the region determination unit 1918 determines a region with a lower signal intensity (luminance value) than 20 percentile of all of signal intensities in the histogram as a target region 2301 as illustrated in FIG. 23C. More specifically, the pixel value (luminance value) of the pixels corresponding to 20 percentile of the total pixel value is set as a threshold value, and a region of pixels having lower luminance values than the threshold value is determined as the target region 2301. The threshold value is not limited to 20 percentile, but can be set at an arbitrary value, such as 10 percentile and 30 percentile, for example, in accordance with a desired configuration.

At this time, the target region sometimes does not include a very small region 2302 in which noise desired to be removed, like salt-and-pepper noise, occurs as illustrated in FIG. 23C. Consequently, the region determination unit 1918 can apply a known technique that is used at the time of generating a mask in a binary image, such as expansion/contraction processing of the binary image and filling processing in the region to the determined target region 2301. Thereby, as illustrated in FIG. 23D, the region determination unit 1918 can set a region with a low signal intensity to which a noise removal filter should be applied, as a target region 2303.

Thereafter, the filter unit 1417 performs filter processing of a high-contrast tomographic image using a moving-average filter of 3×3, to the set target region in step S2002. The kind of the noise removal filter and filter parameters may be arbitrary as in example 5.

As described above, in the OCT apparatus according to the present example, the region determination unit 1918 determines the region of the pixel positions having lower pixel values than the threshold value that is set using the estimation values as the target region. Thereby, a fundus tomographic image with high-contrast and noise in a vitreous body being restrained can be obtained without involving reduction in a spatial resolution of the retina structure as in example 5.

In the present example, the region determination unit 1918 creates the histogram to the high-contrast tomographic image generated based on the estimation values, and sets the threshold value. A method of setting the threshold value is not, however, limited to this method. For example, a histogram is created for at least one tomographic image of the N tomographic images Hereafter are aligned, and a threshold value may be set from the histogram. Further, the region determination processing according to the present example may be applied to the region determination processing in the modified example of example 5.

Embodiment 3

Enhancement of contrast of a tomographic image by the MAP estimation processing described in the Chan et al. publication is a statistical estimation technique, so that, as the number of pixels (the number of tomographic images) that are used increases, true values with greater reliability can be estimated.

During imaging of a tomographic image of a fundus, however, a subject must obviously keep their eyes open. Consequently, at a time of imaging a large number of tomographic images, a very heavy burden is put on the subject. Further, it takes a long time to image a large number of tomographic images, and, therefore, a time burden is put on the subject. In addition, when the imaging time becomes long, the possibility of failing in imaging becomes high, and more burdens on the subject arise, such as the need to perform imaging again.

Consequently, in embodiment 3 of the disclosure, an optical coherence tomography apparatus that generates a high-contrast tomographic image using less tomographic information as compared with the conventional apparatus is provided.

Before describing an example of the present embodiment, the present embodiment will be schematically described. In the Chan et al. publication, signal intensities of the pixels at the same spots of a large number of tomographic images are used as samples, and a true value (signal intensity) is estimated from the probability density distribution of them. In contrast with this, in the present embodiment, in addition to the pixels of the same spots in a plurality of tomographic images, signal intensities of the pixels around the pixel positions are also handled as samples, and the true value is estimated by increasing the number of samples. MAP estimation processing like this is referred to, hereafter, as area MAP estimation processing. The area MAP estimation processing according to the present embodiment can decrease the number of tomographic images (the number of pieces of tomographic information) required to obtain a high-contrast tomographic image, because the number of samples increases by performing MAP estimation processing on the pixels including the surrounding pixels.

Example 7

Hereafter, with reference to FIGS. 24 to 27D, an optical coherence tomographic imaging apparatus (OCT apparatus) according to example 7 of the present embodiment will be described. The OCT apparatus according to the present example has a similar configuration to the OCT apparatus according to example 1 except for a control unit 2400, so that the same reference signs will be used with respect to the components, and an explanation thereof will be omitted. Hereafter, concerning the OCT apparatus according to the present example, a difference from the OCT apparatus of example 1 will be mainly described.

Configuration of Control Unit 2400

A configuration of the control unit 2400 (image processing device) will be described with reference to FIG. 24. FIG. 24 is a block diagram illustrating a schematic configuration of the control unit 2400. In the control unit 2400, an image generation unit 2410, the acquiring unit 220, the drive control unit 230, the storage unit 240 and the display control unit 250 are provided. The acquiring unit 220, the drive control unit 230, the storage unit 240 and the display control unit 250, which are provided in the control unit 2400, are similar to the respective components in example 1, and, therefore, an explanation thereof will be omitted.

In the image generation unit 2410, the anterior eye image generation unit 211, the fundus image generation unit 212, the tomographic image generation unit 213, the calculation unit 215, and an estimation unit 2416 are provided. The anterior eye image generation unit 211, the fundus image generation unit 212, the tomographic image generation unit 213 and the calculation unit 215, which are provided in the image generation unit 2410, are similar to the respective components in example 1, and, therefore, explanation thereof will be omitted.

The estimation unit 2416 performs area MAP estimation processing that will be described later, to a plurality of tomographic images that are generated by the tomographic image generation unit 213, and estimates estimation values of true values of interference signals. The estimation unit 2416 may estimate the estimation values in the respective pixel positions, based on signals after Fourier conversion acquired by the acquiring unit 220, or the like.

The estimation unit 2416 can be also configured by a module that is executed by a CPU and an MPU of the control unit 2400. Further, the estimation unit 2416 may be configured by a circuit, or the like, that realizes a specific function such as ASIC.

Imaging Process of Tomographic Image

Hereafter, an imaging process of a tomographic image according to the present example will be described with reference to FIGS. 25 to 27D. A preview screen of a GUI for control/image display, and a report screen of the GUI for control/image display according to the present example are similar to the preview screen 400 and the report screen 406 according to example 1, and, therefore, an explanation thereof will be omitted. Further, procedures of imaging preparation and start of imaging are similar to the procedures according to example 1, and, therefore, an explanation thereof will be omitted.

Figure 25:
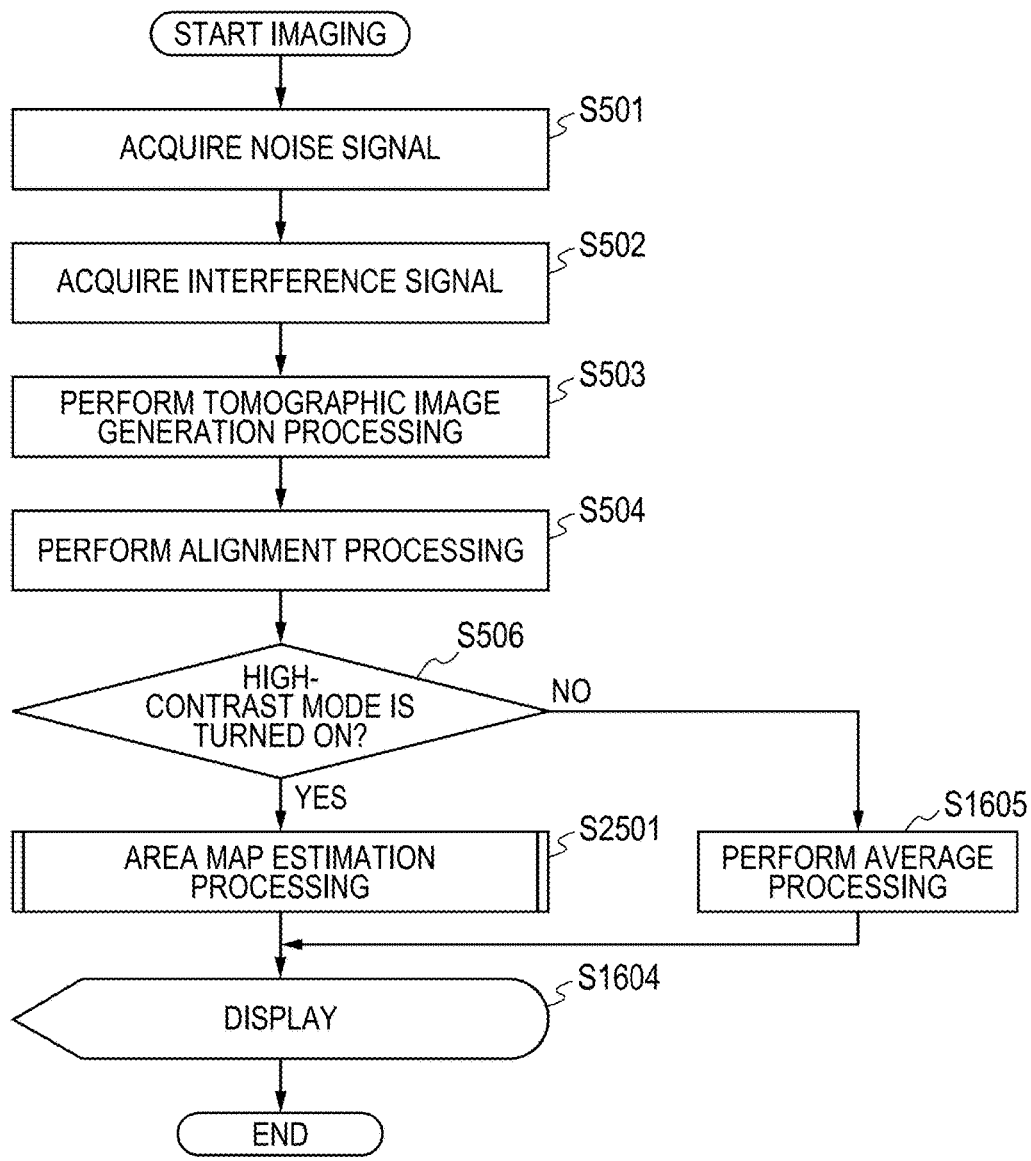
FIG. 25 illustrates a flowchart of a tomographic image imaging process according to example 7.

FIG. 25 illustrates a flowchart of the imaging process of a tomographic image according to the present example. Noise signal acquiring to alignment processing, and ON/OFF determination of a high-contrast mode according to the present example are similar to the same processing according to example 1, and, therefore, an explanation thereof will be simplified using the same reference signs. Further, average processing and processing of display according to the present example are similar to the same processing according to example 4, and, therefore, an explanation thereof will be simplified using the same reference signs.

In the present example, the number of times of imaging for acquiring the interference signals in step S502 is set as N=10. The number of times of imaging is not, however, limited to this number. The number of times of imaging, which is N, may be an arbitrary number of 2 or more so that a desired number of tomographic images for performing the area MAP estimation processing of a tomographic image and addition average processing are obtained. In the area MAP estimation processing, however, the number of pieces of tomographic information (tomographic images) for use in estimation of estimation values can be made smaller as compared with the conventional MAP estimation processing, so that N can be decreased to be a smaller number than the number of times of imaging which is required in the conventional MAP estimation processing.

In step S506, when the tomographic image generation unit 213 determines that the high-contrast mode is not turned on, that is, the high-contrast mode is turned off, the process proceeds to step S1605. In step S1605, the calculation unit 215 generates a tomographic image that is averaged (an averaged tomographic image), as in example 4, and, in step S1604, the display control unit 250 causes the display unit 300 to display the averaged tomographic image to end the imaging process.

When the tomographic image generation unit 213 determines that the high-contrast mode is turned on in step S506, the process proceeds to step S2501.

In step S2501, the estimation unit 2416 performs area MAP estimation processing with respect to the N tomographic images that are aligned, estimates estimation values in the respective pixel positions, and the tomographic image generation unit 213 generates a high-contrast tomographic image using the estimation values that are estimated. Here, the MAP estimation processing itself in the area MAP estimation processing is the same as the one described in the Chan et al. publication, but differs in the point that the signal intensities of the surrounding pixels as well as the target pixel are used in the estimation processing.

Figure 26:
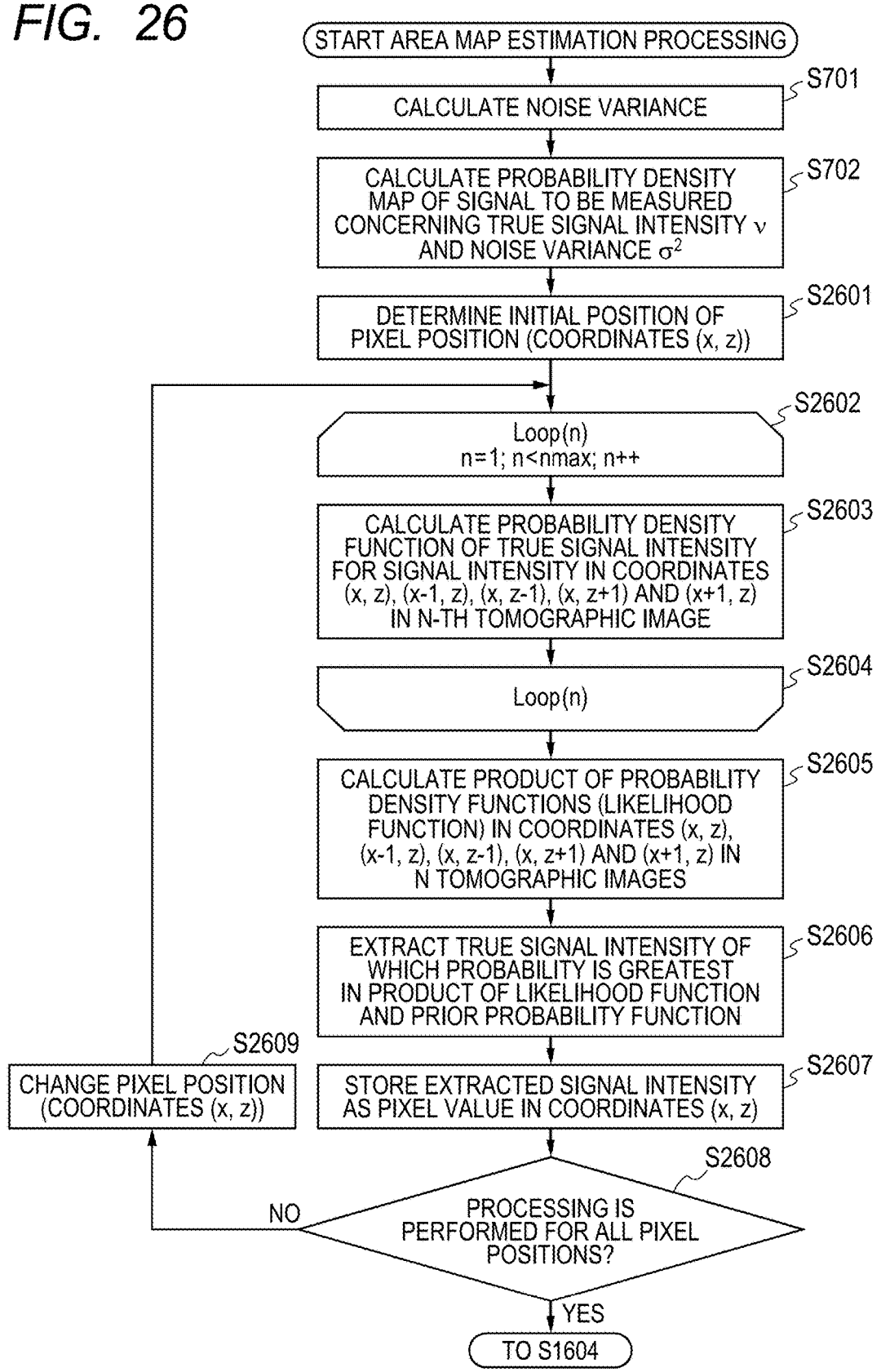
FIG. 26 illustrates a flowchart of area MAP estimation processing according to example 7.

Hereafter, the area MAP estimation processing according to the present example will be described with reference to FIG. 26. FIG. 26 illustrates a flowchart of the area MAP estimation processing according to the present example. In the area MAP estimation processing according to the present example, processing relating to calculation of noise variance and a probability density map is similar to that in the MAP estimation processing according to example 1, so that the same reference signs are used, and explanation thereof will be omitted.

When the area MAP estimation processing is started, and noise variance and the probability density map are calculated in steps S701 and S702, the process proceeds to step S2601. In step S2601, the estimation unit 2416 sets an initial position of a pixel position (coordinates (x, z)) at the time of starting the area MAP estimation processing. In the present example, the initial value of the pixel position is set at the coordinates (1, 1). The initial value is not limited to this value, and may be coordinates of an arbitrary pixel position in the tomographic image.

Further, hereafter, pixels around the target pixel (x, z) (surrounding pixels) for use in the area MAP estimation processing according to the present example will be described as upper, lower, left, and right pixels of the target pixel, that is, as pixels at coordinates (x−1, z), (x, z−1), (x, z+1), and (x+1, z). At this time, at an edge portion of the tomographic image, the surrounding pixels are sometimes out of the image. The case like this can be handled by decreasing the number of pixels that are used in the area MAP estimation processing by the number of pixels that which are out of the image. Further, the pixels on the edge portion of the tomographic image are not used in final image display, and various kinds of boundary processing may be properly applied to these pixels such as performing no area MAP estimation processing on these pixels.

The surrounding pixels of the target pixel for use in the area MAP estimation processing are not limited to the upper, lower, left, and right pixels of the target pixel. The surrounding pixels of the target pixel for use in the area MAP estimation processing can be pixels located around the target pixel. The surrounding pixels may be 8 pixels around the target pixel in 3×3 pixels around the target pixel, or may be 24 pixels around the target pixel in 5×5 pixels around the target pixel, for example. Further, the surrounding pixels may be pixels diagonally adjacent to the target pixel. In the present specification, the surrounding pixels of the target pixel for use in the area MAP estimation processing are simply referred to as the surrounding pixels, and pixel positions of the surrounding pixels are referred to as the pixel positions around the target pixel.

Next, in step S2602 to step S2604, the estimation unit 2416 extracts a probability density with the true signal intensity v as a parameter from the probability density map with respect to each of signal intensities an in the coordinates (x, z) of the target pixels of the first to Nth tomographic images. Further, the estimation unit 2416 similarly extracts the probability density from the probability density map with respect to each of the signal intensities an in the coordinates (x−1, z), (x, z−1), (x, z+1), and (x+1, z) of the surrounding pixels of the first to Nth tomographic images. Thereafter, the estimation unit 2416 calculates a probability density function with the true signal intensity v as the parameter from each of the extracted probability densities. In the drawing, nmax corresponds to N.

In the present example, the estimation unit 2416 extracts probability densities along the direction of the broken arrow of the probability density map illustrated in FIG. 8 with respect to the signal intensities $a_n$ in the coordinates (x, z), (x−1, z), (x, z−1), (x, z+1), and (x+1, z) of the nth tomographic image to be the processing target. When there is a tomographic image for which stop of processing is determined at the time of alignment, the estimation unit 2416 extracts probability densities with respect to the number of tomographic images from which the number of tomographic images for which stop of processing is determined are excluded. When the estimation unit 2416 extracts the probability densities of the true signal intensities v to the signal intensities an in these coordinates of the N tomographic images, and calculates the probability density functions with the true signal intensities v as parameters respectively, the process proceeds to step S2605.

In step S2605, the estimation unit 2416 calculates product of the probability density functions of the true signal intensities v concerning the measured signal intensities of N×5 (corresponding to the target pixels and the surrounding pixels) with the signal intensities $a_1$ to $a_N$ in these coordinates, and sets the calculated product as a likelihood function. The product of the probability density functions is similar to the product of the probability density functions in example 1, and the like, and, therefore, an explanation thereof will be omitted. In the area MAP estimation processing, however, the product of the probability density functions concerning the target pixel is also calculated by multiplication in the probability density functions of the true signal intensities v concerning the surrounding pixels in the same way as in the probability density function of the true signal intensity v concerning the target pixel.

In step S2606, the estimation unit 2416 determines the true signal intensity v at which the probability becomes maximum in the posterior probability function (representative probability density function) that which is the product of the calculated likelihood function and the prior probability. Here, when the prior probability is set as 1 by considering a uniform prior probability that a signal is always acquired as the prior probability, the likelihood function directly becomes the posterior probability function. The estimation unit 2416 determines a parameter (true signal intensity v) at which the probability becomes maximum in the posterior probability function.

More briefly, in the present example, the estimation unit 2416 extracts the probability density for each true signal intensity v with respect to the measured signal intensities $a_1$ to $a_N$ in the target pixel and the surrounding pixels, in steps S2602 to S2604. Thereafter, the estimation unit 2416 calculates the product of the probability density functions obtained by multiplying the probability densities for each true signal intensity v that is extracted with respect to each of the signal intensities in step S2605. Subsequently, the estimation unit 2416 determines the true signal intensity v at which the probability becomes maximum in the calculated product of the probability density functions. In this way, the determined true signal intensity v becomes the estimation value estimated by the estimation unit 2416.

In step S2607, the tomographic image generation unit 213 determines the estimation value (the determined true signal intensity v) estimated by the area MAP estimation processing by the estimation unit 2416 as the representative value in the pixel position corresponding to the coordinates (x, z), and adopts the estimation value as the pixel value.

Thereafter, in step S2608, the estimation unit 2416 determines whether or not the estimation unit 2416 has estimated the estimation values with respect to all the pixel positions. When the estimation unit 2416 determines that the estimation unit 2416 has not estimated the estimation values with respect to all the pixel positions, the process proceeds to step S2609. In step S2609, the estimation unit 2416 moves the pixel position (coordinates (x, z)) the estimation value of which is estimated, and, thereafter, returns the process to step S2602.

In step S2608, when the tomographic image generation unit 213 determines that the tomographic image generation unit 213 has determined the pixel values based on the estimation values with respect to all the pixel positions, the process proceeds to step S1604. The tomographic image generation unit 213 can generate a high-contrast tomographic image having pixel values based on the estimation values by the area MAP estimation processing by determining the pixel values based on the estimation values with respect to all the pixel positions. The storage unit 240 stores the generated high-contrast tomographic image.

In step S1604, the display control unit 250 causes the display unit 300 to display the high-contrast tomographic image stored in the storage unit 240, and ends the imaging process.

In this way, the control unit 2400 can generate a high-contrast tomographic image while decreasing the number of tomographic images that are imaged by performing the area MAP estimation processing.

Further, noise reduction in the high-contrast tomographic image can be also performed by performing the area MAP estimation processing. Here, the noise reduction is described with reference to FIGS. 27A to 27D.

In the ordinary MAP estimation processing, the distribution of the signal intensities of OCT that are acquired with respect to the true signal intensity is assumed from the signal characteristics and noise characteristics, and the true signal intensity at which the appearance probability of the signal based on the distribution of a result of acquiring a large number of signals becomes maximum is estimated. Consequently, for example, when a result that is not correctly measured is included in the signal acquisition result, due to the external factors, such as the intensity of a reflection signal from an eye changing because the eye moves during measurement, or the noise amount changing due to disturbance, it leads to fluctuation in the measurement result.

Here, when the signal intensity which is measured is large with respect to the change of the signal intensity that occurs due to an external factor, an influence is very small. When the signal intensity that which is measured is small, however, a very small change in the signal intensity due to an external factor sometimes causes a large fluctuation in the estimation result. As a result, when the tomographic image of a fundus is imaged, for example, roughness stands out on images particularly in a vitreous body and a sclera that are the regions in which the signal intensities are low.

In contrast with this, in the area MAP estimation processing, not only the signal intensity of the target pixel but also the signal intensity of the surrounding pixels are used in the estimation processing, so that the estimation value can be smoothed similarly to the case in which the filter, such as a moving-average filter, is applied. Consequently, noise in the vitreous body region, and the like, can be also reduced by performing the area MAP estimation processing.

Figure 27A:
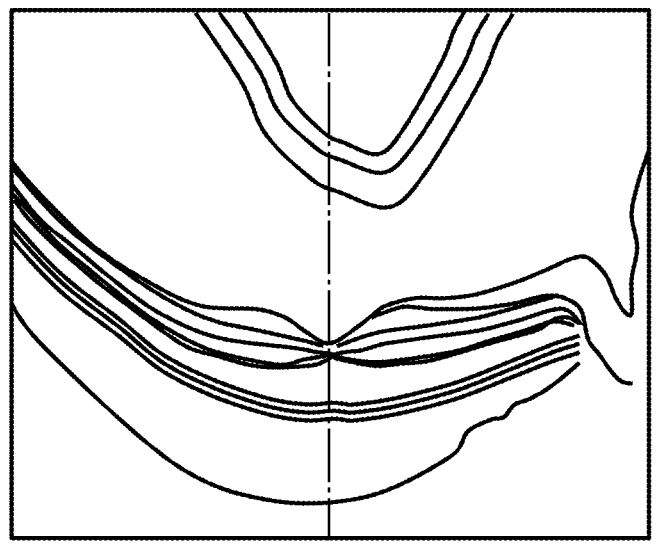
FIG. 27A is a view for describing noise reduction.

FIG. 27A illustrates an example of a high-contrast tomographic image that is generated by ordinary MAP estimation processing using N tomographic images. Further, FIG. 27C illustrates a profile of one line of the high-contrast tomographic image corresponding to an alternate long and short dash line in FIG. 27A. In particular, when the profile of one line of the high-contrast tomographic image corresponding to an A scan image is seen, it is found that noise appears with high contrast as illustrated in FIG. 27C.

Figure 27B:
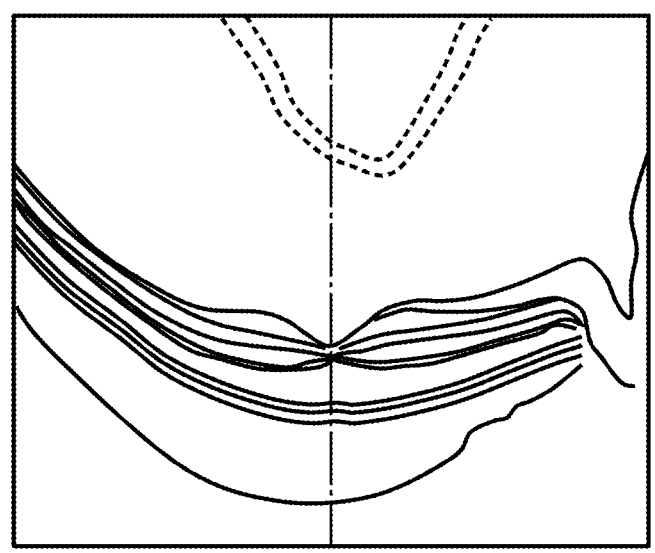
FIG. 27B is a view for describing noise reduction.
Figure 27C:
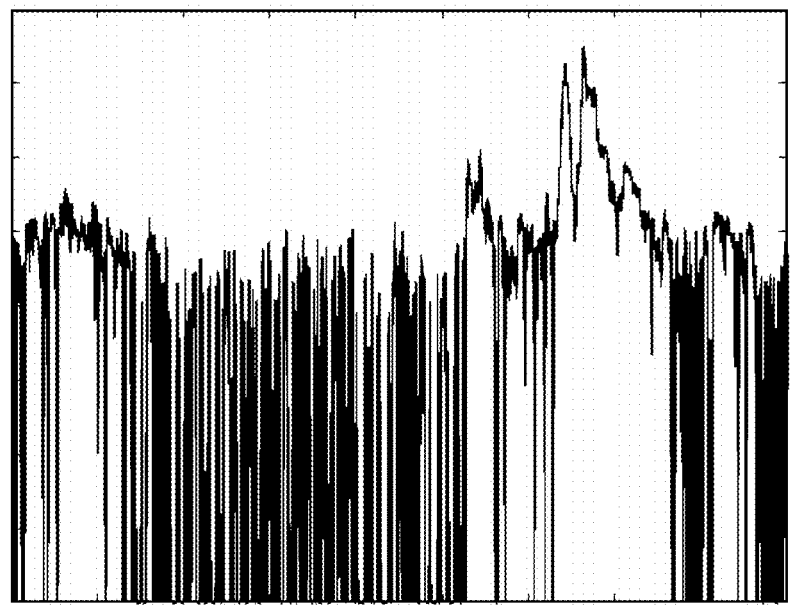
FIG. 27C is a view for describing noise reduction.
Figure 27D:
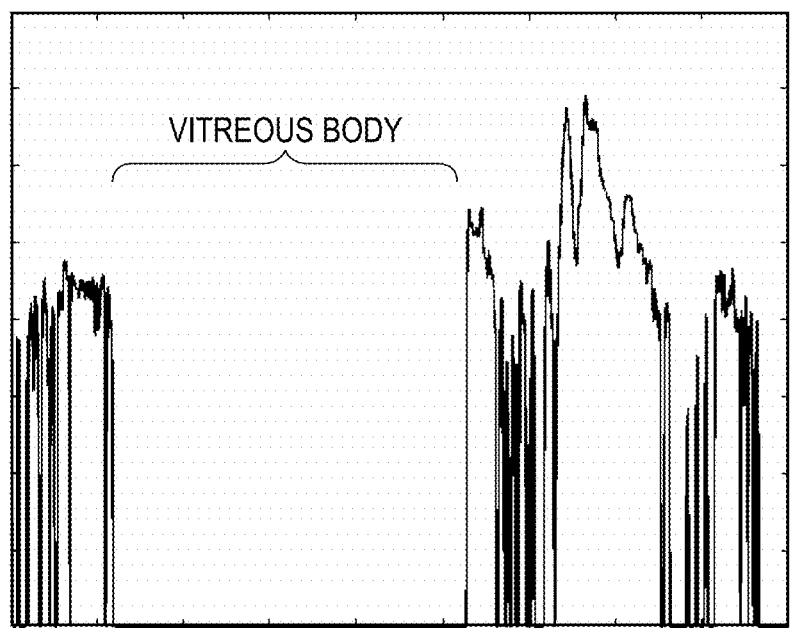
FIG. 27D is a view for describing noise reduction.

In contrast with this, FIG. 27B illustrates an example of the high-contrast tomographic image that is generated by area MAP estimation processing using N tomographic images. Further, FIG. 27D illustrates a profile of one line of the high-contrast tomographic image, that corresponds to an alternate long and short dash line in FIG. 27B. In particular, when the profile of the one line of the high-contrast tomographic image corresponding to the A scan image is seen, it is found that noise is reduced as illustrated in FIG. 27D. In this way, by performing the area MAP estimation processing, noise in the vitreous body region, or the like, can be also reduced.

As described above, the control unit 2400 according to the present example includes the image generation unit 2410. The image generation unit 2410 includes the estimation unit 2416 that estimates the estimation value in a pixel position by performing the area MAP estimation processing using the information on a plurality of tomographic images corresponding to the pixel position of the tomographic image, of the information on the plurality of tomographic images. The estimation unit 2416 performs the area MAP estimation processing using the information on the plurality of tomographic images corresponding to the pixel position, the estimation value of which is estimated and the surrounding pixel positions of the pixel position, of the information on the plurality of tomographic images, and estimates the estimation value.

Concerning the area MAP estimation processing, specifically, with respect to the information on a plurality of tomographic images corresponding to the same pixel position and the surrounding pixel positions of the pixel position, the estimation unit 2416 calculates the probability density functions of the information on the plurality of tomographic images corresponding to these pixel positions using the predetermined probability density function. Thereafter, the estimation unit 2416 calculates the product of the probability density functions using the probability density functions of the information on the plurality of tomographic images that are calculated. Subsequently, the estimation unit 2416 determines the information on the tomographic image in which the probability becomes maximum in the product of the probability density functions, and determines the value of the information on the tomographic image that is determined as the estimation value.

As described above, the control unit 2400 according to the present example obtains the estimation values by the area MAP estimation processing, and generates the tomographic image using the estimation values as the representative values. In the area MAP estimation processing, as the signal intensities for use in estimation of the estimation value, the signal intensities in the pixel positions around the target pixel are used in addition to the signal intensity of the target pixel. Consequently, as compared with the conventional apparatus, a substantially equivalent high-contrast tomographic image can be generated using less tomographic information. Consequently, the time required for imaging can be also shortened, and a burden on the subject can be also decreased. Further, in the area MAP estimation processing, not only the signal intensity of the target pixel, but also the signal intensities of the surrounding pixels are used in estimation processing, so that noise in a vitreous body region, and the like, also can be reduced.

In the present example, the luminance value of the tomographic image is used as the signal intensity in the addition average processing and the area MAP estimation processing, but the signal intensity for use in these kinds of processing is not limited to the luminance value. The signals for use in these kinds of processing can be signals corresponding to the respective pixel positions, and, therefore, can be tomographic signals based on the signals obtained after the interference signals acquired in the OCT optical system are subjected to Fourier conversion. The tomographic signals include, for example, a signal obtained after the interference signal is subjected to Fourier conversion, a signal obtained by applying arbitrary signal processing for image generation to the signal after the Fourier conversion, and signals of a luminance value, and the like, based on these signals.

Further, in the present example, the example of imaging the fundus Er is shown, but the imaging target portion is not limited to the fundus Er, and may be an anterior eye portion.

Modified Example of Example 7

In example 7, in the area MAP estimation processing, the signal intensity of the target pixel and the signal intensities of all pixels of the surrounding pixels are considered to have equivalent values and are used in estimation of the estimation value. In contrast with this, in a modified example of example 7, the signal intensities of the target pixel and the surrounding pixels are considered to be different in contribution degree to calculation of the estimation value in accordance with the pixel positions (coordinates) of the pixels, and weighting corresponding to the coordinates is performed with respect to the probability density function for use in estimation of the estimation value.

Specifically, in step S2605, the estimation unit 2416 assumes to acquire the signal intensity an of the coordinates corresponding to each of the target pixel and the surrounding pixels by a weighting coefficient W corresponding to a desired contribution degree, and uses W probability density functions corresponding to the signal intensity an in calculation of the product of the probability density functions. That is, when the weighting coefficient W to some coordinates is 2, it is considered that the signal intensity $a_n$ of the coordinates is acquired twice, and the probability density function corresponding to the signal intensity $a_n$ is used twice at the time of calculation of the product of the probability density functions. Likewise, the probability density function obtained by multiplying the probabilities of the respective true signal intensities $v_1$ to $v_{max}$ included in the probability density function corresponding to the signal intensity $a_n$ in some coordinates by the weighting coefficient W corresponding to the coordinates may be used in calculation of the product of the probability density functions. The weighting coefficient W can be arbitrarily set in accordance with a desired configuration. For example, the weighting coefficient W may be set to be greater with respect to the surrounding pixels in a lateral direction or an oblique direction of the target region in accordance with the scan direction of the measurement light. In the present modified example, the weighting coefficient W is set to be greater with respect to the surrounding pixels closer to the target region.

FIGS. 28A to 28C illustrate examples of the weighting coefficient W in the present modified example. FIG. 28A illustrates an example of the weighting coefficient W at the time of the upper, lower, left, and right pixels of the target pixel being used as the surrounding pixels similarly to example 7. Here, for example, the probability density function of the signal intensity an in the target pixel is set as $P_t$, and the probability density functions of the signal intensities an in the surrounding pixels are set as $P_{p1}$ to $P_{p4}$. In this case, the estimation unit 2416 uses the probability density function Pt concerning the target pixel twice in calculation of the product of the probability density functions described above, and uses the probability density functions $P_{p1}$ to $P_{p4}$ concerning the surrounding pixels only once. Further, the estimation unit 2416 may use the probability density function in which probabilities of the respective true signal intensities $v_1$ to $v_{max}$ included in the probability density function Pt are respectively squared, in calculation of the product of the probability density functions, and use the probability density functions $P_{p1}$ to $P_{p4}$ directly (as the probability density functions in which the respective probabilities are multiplied by one). In each of the pixels, N probability density functions are calculated, so that the weighting coefficient W is applied to each of the N probability density functions calculated with respect to each of the pixels. Thereby, the contribution degree of the probability density function of the target pixel can be made greater than the surrounding pixels in calculation of the product of the probability density functions, and the true signal intensity v of the target pixel that is more accurate can be estimated.

FIG. 28B illustrates an example of the weighting coefficient W at a time of 8 pixels around the target pixel being used as the surrounding pixels. Likewise, FIG. 28C illustrates an example of the weighting coefficient W at a time of 24 pixels around the target pixel being used as the surrounding pixels. In these examples, the surrounding pixels closer to the target pixel can increase the contribution degree to calculation of the product of the probability density functions, and the true signal intensity v of the target pixel that is more accurate can be estimated as compared with example 7 corresponding to the case in which the target pixel and the surrounding pixels are multiplied by an equal weighting coefficient. The weighting coefficient may be set arbitrarily in accordance with the desired configuration, for example, in accordance with the Gaussian distribution or other distributions as described above. The method for assigning weights is not limited to the above described method, but may be any method in which the weights according to the pixel positions are reflected in comparison of the probabilities of the respective true signal intensities $v_1$ to $v_{max}$ in the product of the probability density functions, for obtaining the maximum probability in the posterior probability.

As described above, in the OCT apparatus according to the present modified example, the estimation unit 2416 assigns weights to the probability density functions of the information on a plurality of tomographic images corresponding to the pixel position the estimation value of which is obtained and the surrounding pixel positions of the pixel position, and calculates the product of the probability density functions to which weighting is performed. More specifically, the estimation unit 2416 performs weighting so that weight becomes heavier in the probability density function of the information on a plurality of tomographic images corresponding to the pixel positions closer to the pixel position in which the product of the probability density functions is obtained. Thereby, the true signal intensity v of the target pixel which is more accurate can be estimated.

Example 8

In the OCT apparatus according to example 7, a high-contrast tomographic image is obtained using less tomographic information using surrounding pixels. Since one representative value is determined by estimating the estimation values from the product of the probability density functions that also include the probability density functions of the surrounding pixels, however, the resolution of the tomographic image that is generated is reduced as compared with the case of using the probability density functions of only the target pixel. Therefore, in an OCT apparatus according to example 8, a tomographic image is generated using area MAP estimation processing that also uses surrounding pixels in a region in which a fine (very small) structure that does not essentially require high resolution, and using the conventional MAP estimation processing that uses only the target pixel in the other regions.

At a time of obtaining a tomographic image of a fundus, a tomographic structure of retina tissue is usually observed, and a vitreous body existing in an eye ball is sometimes observed at the same time. This is because various things are conceivable such as an adverse effect being given to a retina by the retina being pulled by the vitreous body. A vitreous body is made of a transparent substance to pass information of light entering an eye. Consequently, it is well-known that at the time of observing a vitreous body in the OCT using light, the vitreous body can be observed with only a very week signal intensity because the substance is transparent. Further, it is also known that in the vitreous body, a fine structure does not exist as compared with a retina.

Further, lesions are often observed in a retina and a choroid membrane usually, and these membranes are observed with high signal intensities as compared with a vitreous body, in the OCT. Consequently, by performing area MAP estimation processing in only the regions of a vitreous body, and the like, in which signal intensities are lower than a retina, contrast of the vitreous body, and the like, can be enhanced without deteriorating the resolution of a lesion that appears in the retina, or the like.

Figure 30:
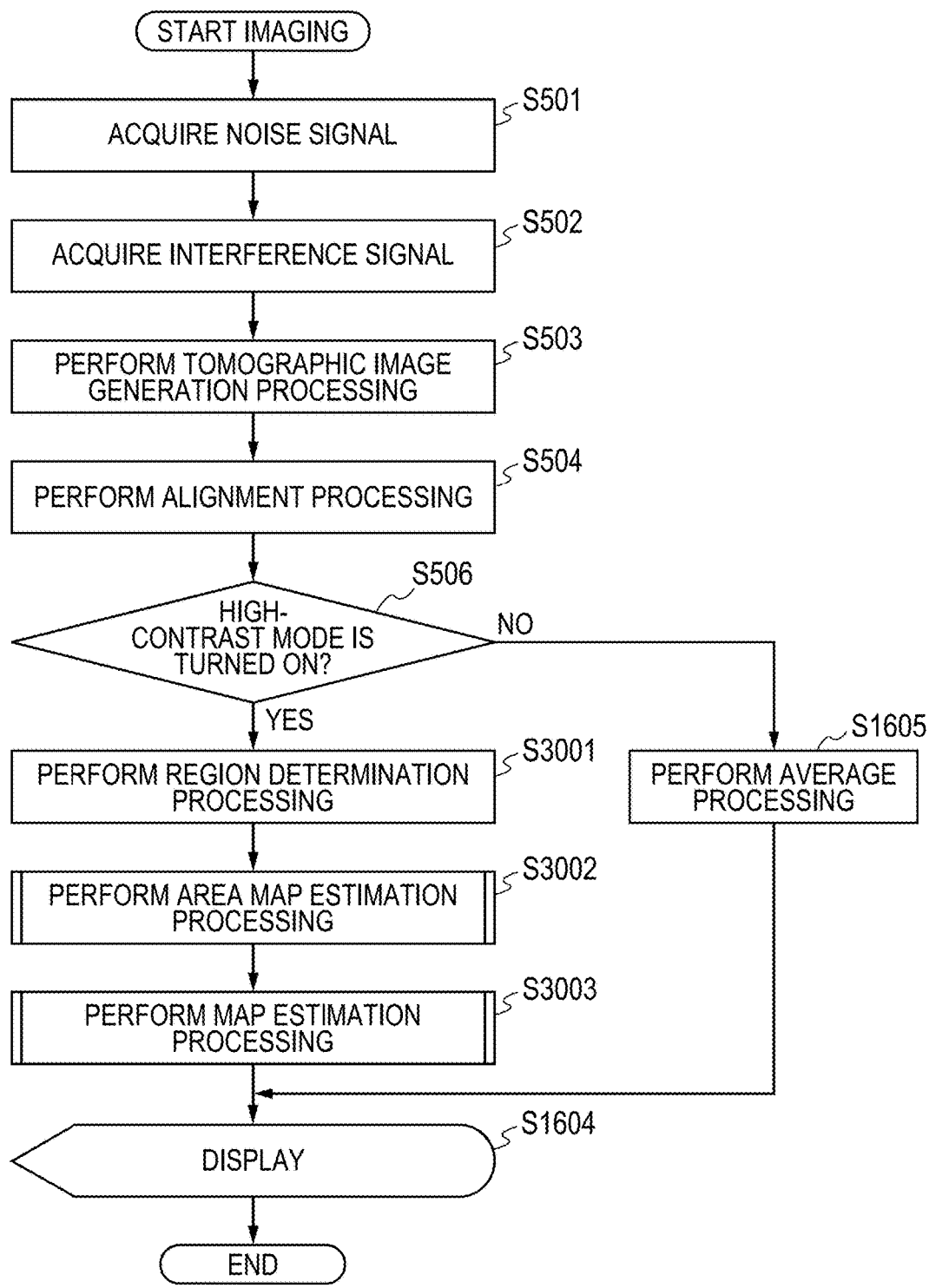
FIG. 30 illustrates a flowchart of a tomographic image imaging process according to example 8.
Figure 31:
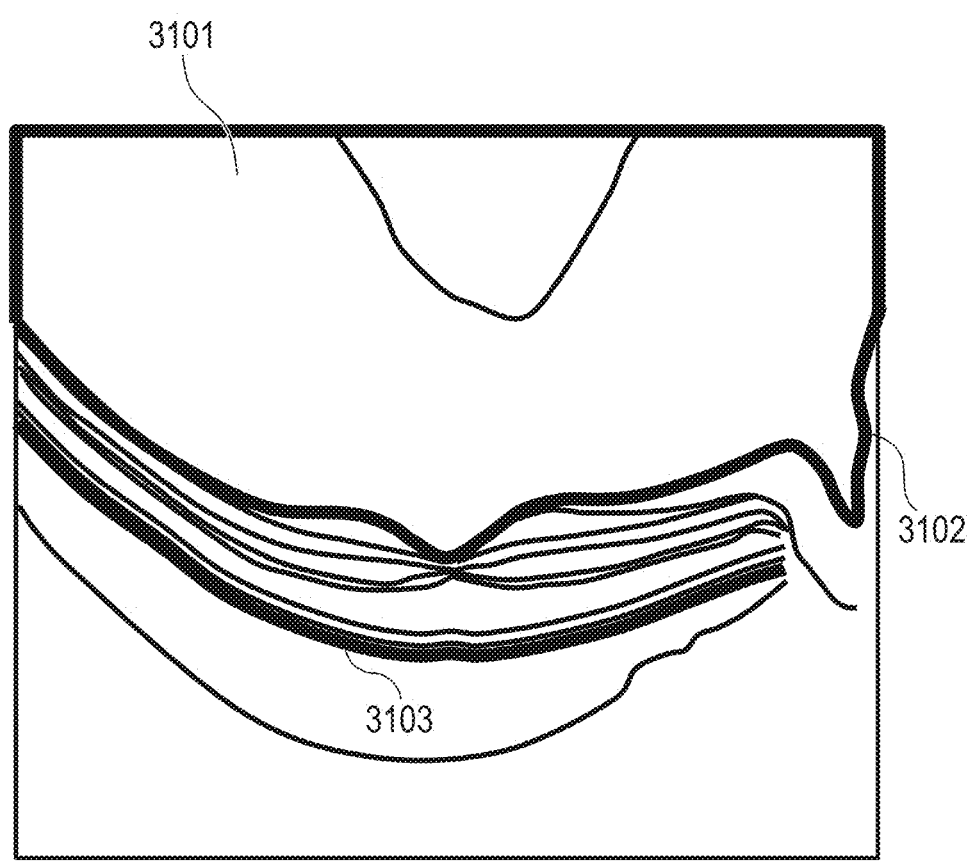
FIG. 31 is a view for describing region determination processing according to example 8.

Hereafter, the OCT apparatus according to example 8 will be described with reference to FIGS. 29 to 31. In the OCT apparatus according to the present example, a vitreous body region is determined as a target region. Consequently, the OCT apparatus according to the present example applies area MAP estimation processing to only the region of a vitreous body in which fine structure does not exist and the signal intensity is low, and performs the conventional MAP estimation processing on a retina. Concerning components of the OCT apparatus according to the present example, for the components similar to those in the OCT apparatus according to example 7, the same reference signs will be used and an explanation thereof will be omitted. Hereafter, concerning the OCT apparatus according to the present example, a difference from the OCT apparatus 1 according to example 7 will be mainly described.

FIG. 29 illustrates a schematic configuration of a control unit 2900 according to the present example. In an image generation unit 2910 of the control unit 2900, an estimation unit 2916, and a region determination unit 2917 are provided in addition to the anterior eye image generation unit 211 to the calculation unit 215.

The estimation unit 2916 performs ordinary MAP estimation processing or the area MAP estimation processing on a plurality of tomographic images generated by the tomographic image generation unit 213, and estimates estimation values of true values of interference signals. Note that the estimation unit 2916 may estimate the estimation values in the respective pixel positions based on the signals after Fourier conversion that are acquired by the acquiring unit 220, or the like.

The region determination unit 2917 determines a target region with low signal intensities to which the area MAP estimation processing should be applied, based on the tomographic image generated by the tomographic image generation unit 213. The region determination unit 2917 may determine the target region based on the signals after Fourier conversion that are acquired by the acquiring unit 220, or the like.

The estimation unit 2916 and the region determination unit 2917 can be also configured by modules that are executed by a CPU and an MPU of the control unit 2900. Further, the estimation unit 2916 and the region determination unit 2917 may be configured by circuits, or the like, that realize specific functions, such as ASIC.

Next, an imaging process according to the present example will be described with reference to FIG. 30. FIG. 30 illustrates a flowchart of the imaging process of a tomographic image according to the present example. The imaging process according to the present example is the same as the imaging process according to example 7 except for the point that the target region to which the area MAP estimation processing is applied is determined, and the area MAP estimation processing is applied to the determined target region, whereas ordinary MAP estimation processing is applied to the other regions. Consequently, an explanation will be omitted except for the difference.

When the tomographic image generation unit 213 determines that the high-contrast mode is turned on in step S506, the process proceeds to step S3001.

In step S3001, the region determination unit 2917 performs segmentation processing on at least one of N tomographic images that which are aligned, and determines a vitreous body region that is a region in which signal intensity is low as a target region. Specific processing is similar to the processing by the region determination unit 214 according to example 1, and, therefore, an explanation thereof will be omitted.

In the present example, the region determination unit 2917 extracts an internal limiting membrane (ILM: Internal Limiting Membrane) by the segmentation processing. FIG. 31 illustrates respective regions at a time of determining the vitreous body region by the segmentation processing. The region determination unit 2917 determines that an opposite side (a pupil side) to a retinal pigment epithelial (RPE) boundary line 3103 with an ILM boundary 3102 as a boundary is a vitreous body region 3101, and determines a region at the pupil side from the ILM boundary 3102 as the vitreous body region 3101. Thereby, the region determination unit 2917 determines the vitreous body region as the target region to which the area MAP estimation processing is applied.

The segmentation processing may be performed using an arbitrary known method other than the above described method. Further, in the present example, the vitreous body region is determined as the target region, but an arbitrary region, such as a sclera region that is known as the region in which the signal intensity is low, may be determined as the target region, for example. In this case, the region determination unit 2917 determines the layer of a sclera, or the like, by segmentation processing, and determines the layer as the target region. Further, the target region may be a plurality of regions, such as a vitreous body region and a sclera region.

After the target region is determined, the estimation unit 2916 applies the area MAP estimation processing to the target region in step S3002. Here, the area MAP estimation processing in the present example is similar to the area MAP estimation processing illustrated in FIG. 26, but the target to which the processing is applied is pixels in the target region, and, therefore, the estimation unit 2916 determines the initial position to be the pixel position in the target region in step S2601. The initial position may be an arbitrary position as long as it is the position in the target region. For example, the estimation unit 2916 determines the coordinates at which the values of x and z are the smallest in the target region as the initial position.

Further, in step S2607, the tomographic image generation unit 213 determines the estimation value estimated by the area MAP estimation processing by the estimation unit 2916 as a representative value in the pixel position corresponding to the coordinates (x, z), and adopts the estimation value as the pixel value. Subsequently, in step S2608, the estimation unit 2916 determines whether or not the estimation unit 2916 performs processing with respect to all pixel positions in the target region, and, when there is an unprocessed pixel position, the estimation unit 2916 moves the pixel position to the unprocessed pixel position in step S2609. In an edge portion of the target region, surrounding pixels are sometimes out of the target region. In this case, if the pixels that are out of the target region are pixels in the image, the signal intensities of the pixels can be also used in estimation. Meanwhile, the regions other than the target region are regions in which the signal intensities are high, so that if the signal intensities of the pixels in the regions are used in the area MAP estimation processing on the target region in which the signal intensity is low, the estimation value sometimes becomes a value away from the true signal intensity v. Consequently, the number of pixels for use in the area MAP estimation processing may be decreased by the number of pixels that are out of the target region.

Next, in step S3003, the estimation unit 2916 applies ordinary MAP estimation processing to the regions other than the target region. Here, the ordinary MAP estimation processing is similar to the MAP estimation processing according to example 4 illustrated in FIG. 17, and, therefore, an explanation thereof will be omitted.

The estimation unit 2916 applies the ordinary MAP estimation processing to the regions other than the target region. Consequently, in this case, the estimation unit 2916 determines the initial position to be the pixel position in the regions other than the target region in step S1701 of the ordinary MAP estimation processing illustrated in FIG. 17. The initial position may be an arbitrary position as long as it is the position in the regions other than the target region. For example, the estimation unit 2916 sets the coordinates at which the values of x and z are the smallest in the regions other than the target region as the initial position. In step S1702, the estimation unit 2916 determines the estimation value estimated by the ordinary MAP estimation processing by the estimation unit 2916 as the representative value, in the pixel position corresponding to the coordinates (x, z), and adopts the estimation value as the pixel value. Subsequently, in step S1703, the estimation unit 2916 determines whether or not the estimation unit 2916 performs processing with respect to all of the pixel positions in the regions other than the target region, and, when there is an unprocessed pixel position, the estimation unit 2916 moves the pixel position to the unprocessed pixel position in step S1704.

As described above, the image generation unit 2910 according to the present example includes the region determination unit 2917 that determines the target region and uses the information on a plurality of tomographic images corresponding to the pixel position for which the estimation value is estimated and the pixel positions around the pixel position, for estimation of the estimation value. More specifically, the region determination unit 2917 determines an anatomical layer (layer boundary) of a fundus based on at least one tomographic image out of a plurality of tomographic images. Thereafter, the region determination unit 2917 determines the target region from the determined layer and the structure of an eye. Subsequently, the tomographic image generation unit 213 performs the area MAP estimation processing in the target region, and performs the ordinary MAP estimation processing in the regions other than the target region. More specifically, in the target region, the estimation unit 2916 performs the area MAP estimation processing using the information on the tomographic image corresponding to the pixel position for which the estimation value is estimated and the pixel positions around the pixel position, and estimates the estimation value. In the regions other than the target region, the estimation unit 2916 performs the ordinary MAP estimation processing using the information on the tomographic image corresponding to only the pixel position for which the estimation value is estimated, and estimates the estimation value.

Thereby, in the regions of a retina, and the like, which are the regions other than the target region, an image having high resolution is generated by the conventional MAP estimation processing. Consequently, a high-contrast tomographic image keeping a sufficient resolution can be generated.

The region determination unit 2917 determines the vitreous body region as the target region. As compared with the vitreous body in which the signal intensity is low, the signal intensity obtained in the retina is high, and, therefore, influence of noise is relatively small. Consequently, in the retina region, the number of samples that is required is not so large as in the vitreous body region, so that the tomographic image of a retina with high quality and high contrast is obtained by performing the ordinary MAP estimation processing. The similar effect can be also provided by determining the sclera region as the target region.

Further, the signal for use in the ordinary MAP estimation processing can be a signal corresponding to each of the pixel positions, and, therefore, can be a tomographic signal based on the signal obtained after the interference signal acquired in the OCT optical system is subjected to Fourier conversion.

Further, as in example 1, the image generation unit 2910 may determine the pixel value using the calculation value (an addition average value, a median value, a mode value, or a maximum value) relating to an averaged tomographic image in the regions other than the target region as the representative value. Further, the region determination unit 2917 may determine the target region using the signal intensity of each pixel as in example 2.

In embodiments 1 to 3 described above, the configuration in which the MAP estimation processing is performed as the processing of estimating the true signal intensities is adopted, but the estimation processing is not limited to this. The processing that is performed in the estimation processing can be processing of estimating the true signal intensity by applying statistical processing to a plurality of tomographic signals, in particular, processing of estimating the true value of the tomographic signal in the pixel position using a distribution of a predetermined model. When estimation processing including surrounding pixels is performed, the processing may be the processing of estimating the true value of the tomographic signal in the pixel position for which the estimation value is estimated, using a distribution of a predetermined model to a plurality of tomographic signals corresponding to the pixel position for which the estimation value is estimated and the pixel positions around the pixel position.

Further, in embodiments 1 to 3, the acquiring unit 220 acquires the interference signal acquired in the imaging optical system 100 and the tomographic signal generated in the tomographic image generation unit 213. The configuration in which the acquiring unit 220 acquires these signals is not, however, limited to this configuration. For example, the acquiring unit 220 may acquire these signals from a server or an imaging apparatus that is connected to the control unit 200 via a local area network (LAN), a wide area network (WAN), the Internet, or the like.

Further, in embodiments 1 to 3, the configuration of a Michelson interferometer is used as the interference optical system of the OCT apparatus, but the configuration of the interference optical system is not limited to this configuration. For example, the interference optical system of the OCT apparatus may have a configuration of a Mach-Zehnder interferometer. Further, the configuration of the imaging optical system 100 is not limited to the above described configuration, and a part of the configuration included in the imaging optical system 100 may be formed as a separate configuration from the imaging optical system 100.

Further, in the imaging optical system 100, a fiber optical system using an optical coupler is used as a dividing unit, but a spatial optical system using a collimator and a beam splitter may be used. Further, as the optical member that divides light into each wavelength, a dichroic mirror is used, but the optical member is not limited to the dichroic mirror. For example, the light may be divided into each wavelength using a mirror that is configured by a prism, or the like, on which a perforated mirror or a hollow mirror is deposited.

In embodiments 1 to 3, a spectral domain OCT (SD-OCT) apparatus using SLD as the light source is described as the OCT apparatus, but the configuration of the OCT apparatus according to the disclosure is not limited to this. For example, the disclosure also can be applied to other arbitrary kinds of OCT apparatuses, such as a wavelength sweep type OCT (SS-OCT) apparatus using a wavelength sweep light source that can sweep the wavelength of exit light.

Further, in embodiments 1 to 3, a subject eye is described as a subject. The subject is not, however, limited to a subject eye, but may be skin, an organ, or the like, for example. At this time, the disclosure also can be applied to medical equipment, such as an endoscope, other than the ophthalmologic apparatus. In this case, the segmentation processing can be performed in accordance with the structure of the subject.

As described above, according to embodiments 1 to 3, the image processing apparatus, the optical coherence tomography apparatus, the image processing method and the computer-readable storage medium that can improve the problem relating to generation of a high-contrast tomographic image using statistical processing are provided.

OTHER EMBODIMENTS

Embodiments of the present invention can also be realized by a computer of a system or an apparatus that reads out and executes computer executable instructions (e.g., one or more programs) recorded on a storage medium (that may also be referred to more fully as a 'non-transitory computer-readable storage medium') to perform the functions of one or more of the above-described embodiments and/or that includes one or more circuits (e.g., an application specific integrated circuit (ASIC)) for performing the functions of one or more of the above-described embodiments, and by a method performed by the computer of the system or the apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus that processes a tomographic image generated using a plurality of sets of tomographic signals acquired by an image sensor, the image sensor being included in an optical coherence tomography (OCT) optical system for performing optical coherence tomographic imaging a plurality of times using a measurement light controlled to scan substantially a same spot of a subject, the image processing apparatus comprising:
(A) a memory that stores instructions; and
(B) at least one processor that executes the instructions stored in the memory:
 (a) to acquire the plurality of sets of tomographic signals acquired by the image sensor; and
 (b) to generate a representative value in each pixel position of the tomographic image, using the plurality of sets of tomographic signals, and to generate the tomographic image with the representative value in each pixel position as a pixel value by determining a target region in which contrast is reduced in the tomographic image, using at least one set of tomographic signals out of the plurality of sets of tomographic signals, and estimating an estimation value, in each pixel position of the target region, by performing statistical processing on a plurality of tomographic signals corresponding to the pixel position, out of the plurality of sets of tomographic signals, wherein the tomographic image is generated with the estimation value as the representative value in the target region.

2. The image processing apparatus according to claim 1, wherein the at least one processor, in estimating the estimation value, estimates a true value of the tomographic signals in the pixel position using a distribution of a predetermined model, with respect to the plurality of tomographic signals corresponding to each pixel position in the target region, as the estimation value.

3. The image processing apparatus according to claim 1, wherein the at least one processor, in estimating the estimation value in the pixel position, performs Maximum a posteriori (MAP) estimation processing on the plurality of tomographic signals corresponding to each pixel position in the target region.

4. The image processing apparatus according to claim 3, wherein the at least one processor, in estimating the estimation value, (i) uses a predetermined probability density function on the plurality of tomographic signals corresponding to each pixel position in the target region to calculate probability density functions of the plurality of tomographic signals corresponding to the pixel position, (ii) calculates a product of the probability density functions concerning the plurality of tomographic signals corresponding to the same pixel position, (iii) determines a value of the tomographic signal in which a probability becomes maximum in the product of the probability density functions, and (iv) sets the determined value of the tomographic signal as the estimation value.

5. The image processing apparatus according to claim 1, wherein the at least one processor, in generating the tomographic image, calculates a calculation value in a pixel position by using a plurality of tomographic signals corresponding to the pixel position of the tomographic image, out of the plurality of sets of tomographic signals, wherein the calculation value is any one of an arithmetic mean value, a median value, a mode value and a maximum value, and the at least one processor generates the tomographic image with the calculation value as the representative value in a region other than the target region in the tomographic image.

6. The image processing apparatus according to claim 5, wherein the at least one processor determines a region of a pixel position having the calculation value that is less than a threshold value that is set by using the calculation value calculated with respect to each pixel position, as the target region.

7. The image processing apparatus according to claim 1, wherein the subject is an eye, and the at least one processor determines the target region based on at least one set of tomographic signals, out of the plurality of sets of tomographic signals, and a structure of the eye.

8. The image processing apparatus according to claim 7, wherein the at least one processor determines a layer boundary of a fundus portion in the tomographic image by using at least one set of tomographic signals, out of the plurality of sets of tomographic signals, and determines the target region based on the layer boundary and the structure of the eye.

9. The image processing apparatus according to claim 1, wherein the at least one processor determines a region having a value of a tomographic signal that is less than a threshold value that is set by using one set of tomographic signals, out of the plurality of sets of tomographic signals, as the target region.

10. The image processing apparatus according to claim 1, wherein the memory further stores the plurality of sets of tomographic signals that are subjected to gradation conversion to 8-bit information.

11. The image processing apparatus according to claim 1, wherein the subject is a moving eye, and the at least one processor further executes the instructions (c) to control a scanner of the OCT optical system to perform the optical coherence tomographic imaging of substantially the same spot of the subject a plurality of times.

12. The image processing apparatus according to claim 1, wherein the at least one processor, in generating the tomographic image, generates the tomographic image using (i) the estimation value in a vitreous body region, and (ii) a value acquired by processing that is different from the estimating, in a retina region.

13. An image processing apparatus that processes a tomographic image generated using tomographic signals acquired by an image sensor, the image sensor being included in an optical coherence tomography (OCT) optical system for performing optical coherence tomographic imaging of a subject, the image processing apparatus comprising:
(A) a memory that stores instructions; and
(B) at least one processor that executes the instructions stored in the memory:
 (a) to acquire the tomographic signals acquired by the image sensor; and
 (b) to generate the tomographic image using the tomographic signals by determining a target region in which contrast is reduced in the tomographic image, using the tomographic signals, and estimating an estimation value by performing statistical processing on tomographic signals of the target region, out of the tomographic signals, wherein the tomographic image is generated with the estimation value as a pixel value in the target region.

14. An optical coherence tomography apparatus comprising:
an imaging optical system that performs optical coherence tomography imaging of a subject; and
the image processing apparatus according to claim 13.

15. The image processing apparatus according to claim 13, wherein the subject is a moving eye, and the at least one processor further executes the instructions (c) to control a scanner of the OCT optical system to perform the optical coherence tomographic imaging of substantially the same spot of the subject a plurality of times.

16. The image processing apparatus according to claim 13, wherein the at least one processor, in generating the tomographic image, generates the tomographic image using (i) the estimation value in a vitreous body region, and (ii) a value acquired by processing that is different from the estimating, in a retina region.

17. An image processing apparatus that processes a tomographic image generated using tomographic signals acquired by an image sensor, the image sensor being included in an optical coherence tomography (OCT) optical system for performing optical coherence tomographic imaging of a subject, the image processing apparatus comprising:
(A) a memory that stores instructions; and
(B) at least one processor that executes the instructions stored in the memory:
 (a) to acquire the tomographic signals acquired by the image sensor; and
 (b) to generate the tomographic image using the tomographic signals, by estimating an estimation value by performing statistical processing on tomographic signals corresponding to a pixel position of the tomographic image out of the tomographic signals, and applying a noise removal filter to a tomographic image generated by using the estimation value as a pixel value.

18. The image processing apparatus according to claim 17, wherein the subject is a moving eye, and the at least one processor further executes the instructions (c) to control a scanner of the OCT optical system to perform the optical coherence tomographic imaging of substantially the same spot of the subject a plurality of times.

19. The image processing apparatus according to claim 17, wherein the at least one processor, in generating the tomographic image, generates the tomographic image using (i) the estimation value in a vitreous body region, and (ii) a value acquired by processing that is different from the estimating, in a retina region.

20. An image processing apparatus that processes a tomographic image generated using tomographic signals acquired by an image sensor, the image sensor being included in an optical coherence tomography (OCT) optical system for performing optical coherence tomographic imaging of a subject, the image processing apparatus comprising:
(A) a memory that stores instructions; and
(B) at least one processor that executes the instructions stored in the memory:
 (a) to acquire the tomographic signals acquired by the image sensor; and
 (b) to generate the tomographic image using the tomographic signals, by estimating an estimation value by performing statistical processing on tomographic signals corresponding to a pixel position of the tomographic image out of the tomographic signals, wherein the estimation value is estimated by performing statistical processing on the tomographic signals corresponding to a pixel position, the estimation value of which is estimated, and pixel positions around the pixel position, out of the tomographic signals, wherein the tomographic image is generated with the estimation value as a pixel value.

21. The image processing apparatus according to claim 20, wherein the subject is a moving eye, and the at least one processor further executes the instructions (c) to control a scanner of the OCT optical system to perform the optical coherence tomographic imaging of substantially the same spot of the subject a plurality of times.

22. The image processing apparatus according to claim 20, wherein the at least one processor, in generating the tomographic image, generates the tomographic image using (i) the estimation value in a vitreous body region, and (ii) a value acquired by processing that is different from the estimating, in a retina region.

23. An image processing method that processes a tomographic image generated using tomographic signals acquired by an image sensor, the image sensor being included in an optical coherence tomography (OCT) optical system for performing optical coherence tomographic imaging of a subject, the image processing method comprising:
   (a) acquiring the tomographic signals acquired by the image sensor; and
   (b) generating the tomographic image using the tomographic signals, by (i) determining a target region in which contrast is reduced in the tomographic image, using the tomographic signals, (ii) estimating an estimation value by performing statistical processing on tomographic signals of the target region, out of the tomographic signals, and (iii) generating the tomographic image with the estimation value as a pixel value in the target region.

24. A non-transitory computer-readable storage medium storing a program that causes a processor to execute respective steps of the image processing method according to claim 23.

25. An image processing method that processes a tomographic image generated by using tomographic signals acquired by an image sensor, the image sensor being included in an optical coherence tomography (OCT) optical system for performing optical coherence tomographic imaging on a subject, the image processing method comprising:
   (a) acquiring the tomographic signals acquired by the image sensor; and
   (b) generating the tomographic image using the tomographic signals, by (i) estimating an estimation value by performing statistical processing on tomographic signals corresponding to a pixel position of the tomographic image, out of the tomographic signals, and (ii) applying a noise removal filter to a tomographic image generated by using the estimation value as a pixel value.

26. A non-transitory computer-readable storage medium storing a program that causes a processor to execute respective steps of the image processing method according to claim 25.

27. An image processing method that processes a tomographic image generated using tomographic signals acquired by an image sensor, the image sensor being included in an optical coherence tomography (OCT) optical system for performing optical coherence tomographic imaging on a subject, the image processing method comprising:
   (a) acquiring the tomographic signals acquired by the image sensor; and
   (b) generating the tomographic image using the tomographic signals, by (i) estimating an estimation value by performing statistical processing on tomographic signals corresponding to a pixel position of the tomographic image out of the tomographic signals, the estimating of the estimation value including performing statistical processing on tomographic signals corresponding to a pixel position, the estimation value of which is estimated, and pixel positions around the pixel position, out of the tomographic signals, and (ii) generating the tomographic image with the estimation value as a pixel value.

28. A non-transitory computer-readable storage medium storing a program that causes a processor to execute respective steps of the image processing method according to claim 27.

* * * * *